US009312495B2

(12) United States Patent
Pflumm et al.

(10) Patent No.: US 9,312,495 B2
(45) Date of Patent: Apr. 12, 2016

(54) MATERIALS FOR ORGANIC ELECTROLUMINESCENT DEVICES

(75) Inventors: Christof Pflumm, Darmstadt (DE); Amir Hossain Parham, Frankfurt am Main (DE); Constanze Brocke, Gross-Gerau (DE); Elvira Montenegro, Weinheim (DE); Frank Voges, Bad Duerkheim (DE); Holger Heil, Frankfurt am Main (DE); Arne Buesing, Frankfurt am Main (DE)

(73) Assignee: Merck Patent GmbH, Darmstadt (DE)

( * ) Notice: Subject to any disclaimer, the term of this patent is extended or adjusted under 35 U.S.C. 154(b) by 77 days.

(21) Appl. No.: 13/823,401

(22) PCT Filed: Aug. 16, 2011

(86) PCT No.: PCT/EP2011/004106
§ 371 (c)(1),
(2), (4) Date: Apr. 9, 2013

(87) PCT Pub. No.: WO2012/034627
PCT Pub. Date: Mar. 22, 2012

(65) Prior Publication Data
US 2013/0207046 A1 Aug. 15, 2013

(30) Foreign Application Priority Data

Sep. 15, 2010 (DE) .......................... 10 2010 045 405

(51) Int. Cl.
| | |
|---|---|
| *H01L 51/00* | (2006.01) |
| *C07C 211/61* | (2006.01) |
| *C07D 219/02* | (2006.01) |
| *C07D 241/46* | (2006.01) |
| *C07D 265/38* | (2006.01) |
| *C07D 279/36* | (2006.01) |
| *C09K 11/06* | (2006.01) |
| *H05B 33/14* | (2006.01) |
| *H01L 51/50* | (2006.01) |

(52) U.S. Cl.
CPC ............ *H01L 51/006* (2013.01); *C07C 211/61* (2013.01); *C07D 219/02* (2013.01); *C07D 241/46* (2013.01); *C07D 265/38* (2013.01); *C07D 279/36* (2013.01); *C09K 11/06* (2013.01); *H01L 51/0058* (2013.01); *H05B 33/14* (2013.01); *C07C 2103/18* (2013.01); *C07C 2103/96* (2013.01); *C07C 2103/97* (2013.01); *C09K 2211/1011* (2013.01); *C09K 2211/1014* (2013.01); *C09K 2211/1029* (2013.01); *C09K 2211/1033* (2013.01); *C09K 2211/1037* (2013.01); *H01L 51/0008* (2013.01); *H01L 51/5012* (2013.01); *H01L 51/5016* (2013.01); *H01L 51/5056* (2013.01); *Y02E 10/549* (2013.01)

(58) Field of Classification Search
CPC .. C07C 209/10; C07C 211/54; C07C 211/61; H01L 51/00; H01L 51/006
USPC ...................... 252/500, 301.16; 564/308, 427
See application file for complete search history.

(56) References Cited

U.S. PATENT DOCUMENTS

| | | | |
|---|---|---|---|
| 8,361,638 B2 * | 1/2013 | Stoessel et al. ............... 428/690 |
| 9,102,797 B2 * | 8/2015 | Schulte .................. C08G 61/12 |
| 2005/0054854 A1 | 3/2005 | Stossel et al. |
| 2007/0215857 A1 * | 9/2007 | Saito ............................. 257/14 |
| 2008/0038587 A1 | 2/2008 | Wen et al. |
| 2008/0206598 A1 * | 8/2008 | Ohsawa et al. ............... 428/690 |
| 2009/0167161 A1 | 7/2009 | Yabunouchi et al. |
| 2009/0167166 A1 * | 7/2009 | Bach et al. ..................... 313/504 |
| 2010/0019657 A1 | 1/2010 | Eum et al. |
| 2010/0301744 A1 * | 12/2010 | Osaka et al. .................. 313/504 |
| 2011/0147728 A1 | 6/2011 | Kawakami et al. |
| 2011/0147792 A1 * | 6/2011 | Kawata et al. ................ 257/103 |
| 2011/0210316 A1 * | 9/2011 | Kadoma et al. ................ 257/40 |
| 2011/0215714 A1 * | 9/2011 | Seo et al. ....................... 313/504 |
| 2011/0248246 A1 * | 10/2011 | Ogita et al. ..................... 257/40 |
| 2012/0025697 A1 * | 2/2012 | Kadoma et al. ............... 313/504 |
| 2012/0228552 A1 * | 9/2012 | Parham et al. ............ 252/301.16 |
| 2013/0015403 A1 * | 1/2013 | Becker et al. ............ 252/301.16 |
| 2014/0088305 A1 * | 3/2014 | Parham et al. ................ 544/180 |
| 2014/0138661 A1 * | 5/2014 | Ludemann et al. ............. 257/40 |
| 2014/0203216 A1 * | 7/2014 | Parham et al. ................ 252/500 |
| 2015/0065730 A1 * | 3/2015 | Montenegro .......... C07C 211/54 548/440 |
| 2015/0115239 A1 * | 4/2015 | Pflumm ................ H01L 51/006 257/40 |
| 2015/0236261 A1 * | 8/2015 | Stoessel ................ H01L 51/006 257/40 |

FOREIGN PATENT DOCUMENTS

| | | |
|---|---|---|
| CN | 101273008 A | 9/2008 |
| JP | 2004-269696 A | 9/2004 |
| JP | 2009-215281 A | 9/2009 |
| KR | 2010-0006072 A | 1/2010 |
| WO | WO-03/037844 A1 | 5/2003 |
| WO | WO-2007043354 A1 | 4/2007 |
| WO | WO-2009/084268 A1 | 7/2009 |

(Continued)

OTHER PUBLICATIONS

International Search Report for PCT/EP2011/004106 mailed Feb. 22, 2012.

(Continued)

*Primary Examiner* — Douglas McGinty
(74) *Attorney, Agent, or Firm* — Drinker Biddle & Reath LLP

(57) ABSTRACT

The present invention relates to compounds of the formula (1) which are suitable for use in electronic devices, in particular organic electroluminescent devices, and to electronic devices which comprise these compounds.

21 Claims, No Drawings

(56) References Cited

FOREIGN PATENT DOCUMENTS

| WO | WO-2010/015306 A1 | 2/2010 |
| WO | WO-2010/050778 A1 | 5/2010 |
| WO | WO 2013/120577 A1 * | 8/2013 |

OTHER PUBLICATIONS

Natera et al., "A Novel Electrochromic Polymer Synthesized through Electropolymerization of a New Donor-Acceptor Bipolar System", Macromolecules, vol. 40, pp. 4456-4463 (2007).

Chen et al., "Versatile, Benzimidazole/Amine-Based Ambipolar Compounds for Electroluminescent Applications: Single-Layer, Blue, Flourescent OLEDs, Hosts for Single-Layer, Phosphorescent OLEDs", Adv. Funct. Mater., vol. 19, pp. 2661-2670 (2009).

Natera et al., "Synthesis and Properties of a Novel Cross-Linked Electroactive Polymer Formed from a Bipolar Starburst Monomer", Macromolecules, vol. 42, pp. 626-635 (2009).

* cited by examiner

MATERIALS FOR ORGANIC ELECTROLUMINESCENT DEVICES

CROSS-REFERENCE TO RELATED APPLICATIONS

This application is a national stage application (under 35 U.S.C. §371) of PCT/EP2011/004106, filed Aug. 16 2011, which claims benefit of German application 10 2010 045 405.2, filed Sep. 15, 2010 which are both incorporated by reference.

The present invention relates to materials for use in electronic devices, in particular in organic electroluminescent devices, and to electronic devices comprising these materials.

The structure of organic electroluminescent devices (OLEDs) in which organic semiconductors are employed as functional materials is described, for example, in U.S. Pat. No. 4,539,507, U.S. Pat. No. 5,151,629, EP 0676461 and WO 98/27136. The emitting materials employed here are increasingly organo-metallic complexes which exhibit phosphorescence instead of fluorescence (M. A. Baldo et al., *Appl. Phys. Lett.* 1999, 75, 4-6).

In accordance with the prior art, the hole-transport materials used in the hole-transport layer or in the hole-injection layer are, in particular, triarylamine derivatives which either contain at least two triarylamino groups or at least one triarylamino group and at least one carbazole group. These compounds are frequently derived from diarylamino-substituted triphenylamines (TPA type), from diarylamino-substituted biphenyl derivatives (TAD type) or combinations of these base compounds. Furthermore, for example, use is made of spirobifluorene derivatives which are substituted by two or four diarylamino groups (for example in accordance with EP 676461 or U.S. Pat. No. 7,714,145). In the case of these compounds, there is furthermore a need for improvement both in the case of fluorescent and in the case of phosphorescent OLEDs, in particular with respect to efficiency, lifetime and operating voltage on use in an organic electroluminescent device and with respect to the thermal stability during sublimation.

The object of the present invention is to provide compounds which are suitable for use in a fluorescent or phosphorescent OLED, in particular a phosphorescent OLED, for example as hole-transport material in a hole-transport or exciton-blocking layer or as matrix material in an emitting layer.

Surprisingly, it has been found that certain compounds described below in greater detail achieve this object and result in significant improvements in the organic electroluminescent device, in particular with respect to the lifetime, the efficiency and the operating voltage. This applies to phosphorescent and fluorescent electroluminescent devices, especially on use of the compounds according to the invention as hole-transport material or as matrix material. The materials generally have high thermal stability and can therefore be sublimed without decomposition and without a residue. The present invention therefore relates to these materials and to electronic devices which comprise compounds of this type. In particular, it is a surprising result that very good results are obtained with an aromatic monoamine, since hole-transport materials containing at least two nitrogen atoms are generally employed in organic electroluminescent devices.

The present invention therefore relates to a compound of the following formula (1):

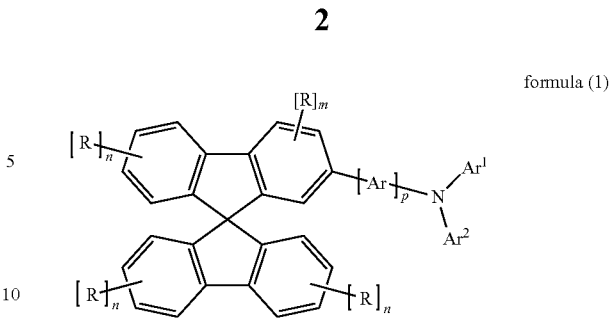

formula (1)

where the following applies to the symbols and indices used:

Ar is, identically or differently on each occurrence, an aromatic ring system selected from the group consisting of benzene, naphthalene, phenanthrene, fluorene, spirobifluorene, dibenzofuran and dibenzothiophene, each of which may be substituted by one or more radicals $R^1$; Ar may also be connected to $Ar^1$ and/or to $Ar^2$ here by a group E;

$Ar^1$, $Ar^2$ are, identically or differently on each occurrence, an aromatic or heteroaromatic ring system having 6 to 60 C atoms selected from the group consisting of benzene, naphthalene, phenanthrene, fluorene, dibenzofuran, dibenzothiophene, each of which may also be substituted by one or more radicals $R^1$, or unsubstituted spirobifluorene or a combination of two, three, four or five of these groups, which may in each case be identical or different; $Ar^1$ and $Ar^2$ here may be connected to one another and/or $Ar^1$ may be connected to Ar and/or $Ar^2$ may be connected to Ar by a group E;

E is, identically or differently on each occurrence, selected from the group consisting of $C(R^1)_2$, O, S and $NR^1$;

R, $R^1$ are on each occurrence, identically or differently, selected from the group consisting of H, D, F, Cl, Br, I, CN, $Si(R^2)_3$, a straight-chain alkyl, alkoxy or thioalkyl group having 1 to 40 C atoms or a branched or cyclic alkyl, alkoxy or thioalkyl group having 3 to 40 C atoms, each of which may be substituted by one or more radicals $R^2$, where in each case one or more non-adjacent $CH_2$ groups may be replaced by $Si(R^2)_2$, $C=NR^2$, $P(=O)(R^2)$, SO, $SO_2$, $NR^2$, O, S or $CONR^2$ and where one or more H atoms may be replaced by D, F, Cl, Br or I, an aromatic or heteroaromatic ring system having 6 to 60 C atoms selected from the group consisting of benzene, naphthalene, phenanthrene, fluorene, spirobifluorene, dibenzofuran and dibenzothiophene, which may in each case be substituted by one or more radicals $R^2$, or a combination of two, three, four or five of these groups, which may in each case be identical or different, an aryloxy group having 5 to 60 aromatic ring atoms, which may be substituted by one or more radicals $R^2$, or an aralkyl group having 5 to 60 aromatic ring atoms, which may in each case be substituted by one or more radicals $R^2$, where two or more adjacent substituents R or two or more adjacent substituents $R^1$ may optionally form a mono- or polycyclic, aliphatic ring system, which may be substituted by one or more radicals $R^2$;

$R^2$ is on each occurrence, identically or differently, selected from the group consisting of H, D, F, Cl, Br, I, $Si(R^3)_3$, a straight-chain alkyl, alkoxy or thioalkyl group having 1 to 40 C atoms or a branched or cyclic alkyl, alkoxy or thioalkyl group having 3 to 40 C atoms, each of which may be substituted by one or more radicals $R^3$, where one or more non-adjacent $CH_2$ groups may be replaced by $Si(R^3)_2$, $C=NR^3$, $P(=O)(R^3)$, SO, $SO_2$, $NR^3$, O, S or $CONR^3$ and where one or more H atoms may be replaced by D, F, Cl, Br or I, an aromatic ring system having 6 to 60 C atoms selected from the group consisting of benzene, naphthalene, phenanthrene, fluorene, spirobifluorene or a combination of two, three, four or five of these groups, which may in each case be identical or different, which may in each case be substituted by one or more radicals $R^3$, an aryloxy group having 5 to 60 aromatic ring atoms, which may be substituted by one or more radicals $R^3$, or an aralkyl group having 5 to 60 aromatic ring atoms, which may be substituted by one or more radicals $R^3$, where two or more adjacent substituents $R^2$ may optionally form a mono- or polycyclic, aliphatic ring system, which may be substituted by one or more radicals $R^3$;

$R^3$ is selected from the group consisting of H, D, F, an aliphatic hydrocarbon radical having 1 to 20 C atoms, an aromatic ring system having 6 to 30 C atoms, in which one or more H atoms may be replaced by D or F, where two or more adjacent substituents $R^3$ may form a mono- or polycyclic, aliphatic ring system with one another;

m is 0, 1, 2 or 3;

n is on each occurrence, identically or differently, 0, 1, 2, 3 or 4;

p is 0, 1 or 2;

the following compounds are excluded from the invention:

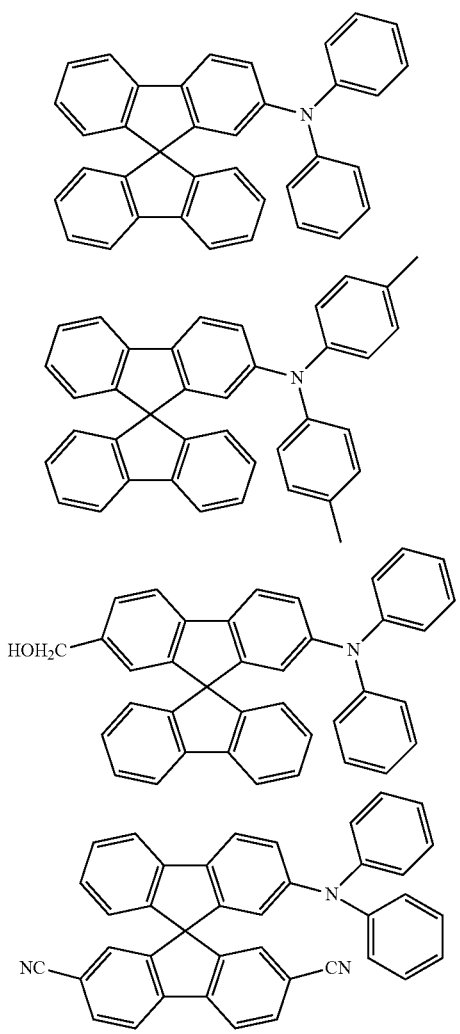

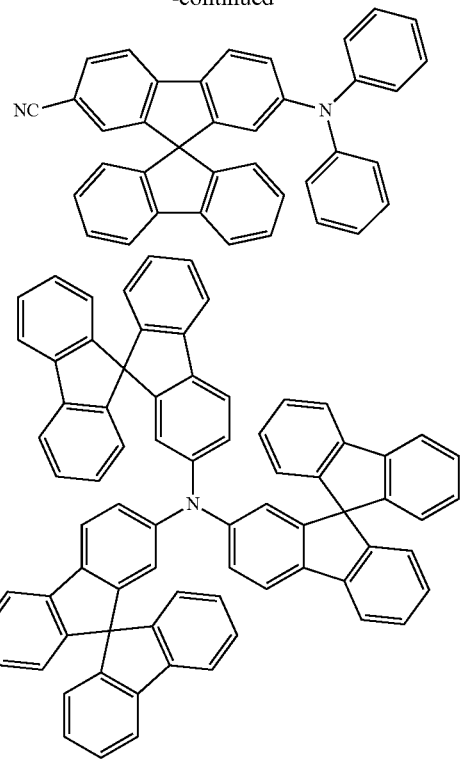

As is evident from the definitions given above, the compound of the formula (1) contains no heteroaromatic substituents R on the spirobifluorene. Furthermore, apart from the arylamino group shown in the formula (1) and optionally the group E, it contains no further amino groups and no carbazole groups.

An aryl group in the sense of this invention is taken to mean either a simple aromatic ring, i.e. benzene, or a condensed (anellated) aryl group, for example naphthalene or phenanthrene. By contrast, aromatic groups linked to one another by a single bond, such as, for example, biphenyl or fluorene, are not referred to as an aryl group, but instead as an aromatic ring system.

An aromatic ring system in the sense of this invention contains 6 to 60 C atoms in the ring system, where the aromatic ring system is built up from benzene, naphthalene, phenanthrene, fluorene and spirobifluorene or combinations of these groups. An aromatic ring system in the sense of this invention is, in particular, also intended to be taken to mean a system in which, in addition, a plurality of aryl groups is linked to one another directly or via a carbon atom. Thus, for example, systems such as biphenyl, terphenyl, quaterphenyl, fluorene, 9,9'-spirobifluorene, 9,9-diarylfluorene, etc., in particular, are also intended to be taken to be aromatic ring systems in the sense of this invention. The aromatic ring system here by definition contains no amino groups. Triarylamino groups are thus not covered by the definition of an aromatic ring system.

For the purposes of the present invention, an aliphatic hydrocarbon radical or an alkyl group or an alkenyl or alkynyl group, which may typically contain 1 to 40 or also 1 to 20 C atoms and in which, in addition, individual H atoms or $CH_2$ groups may be substituted by the above-mentioned groups, is preferably taken to mean the radicals methyl, ethyl, n-propyl, i-propyl, n-butyl, i-butyl, s-butyl, t-butyl, 2-methylbutyl, n-pentyl, s-pentyl, neopentyl, cyclopentyl, n-hexyl, neohexyl, cyclohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl, heptynyl or octynyl. An alkoxy group having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy or 2,2,2-trifluoroethoxy. A thioalkyl group having 1 to 40 C atoms is taken to mean, in particular, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynyl-thio, heptynylthio or octynylthio. In general, alkyl, alkoxy or thioalkyl groups in accordance with the present invention can be straight-chain, branched or cyclic, where one or more non-adjacent $CH_2$ groups may be replaced by the above-mentioned groups; furthermore, one or more H atoms may also be replaced by D, F, Cl, Br, I, CN or $NO_2$, preferably F, Cl or CN, further preferably F or CN, particularly preferably CN.

In a preferred embodiment of the invention, the compound of the formula (1) is selected from the compounds of the following formula (2):

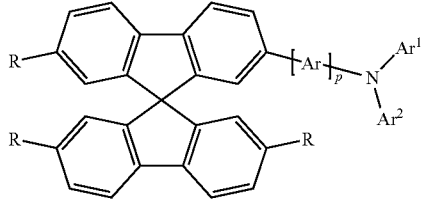

formula (2)

where the symbols and indices used have the meanings given above.

In a particularly preferred embodiment of the invention, the compound of the formula (1) is selected from the compounds of the following formulae (3a) and (3b):

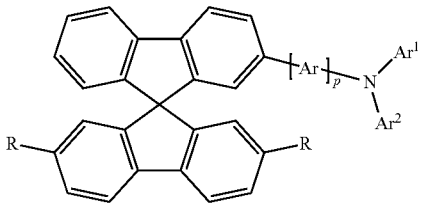

formula (3a)

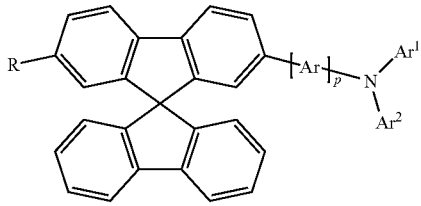

formula (3b)

where the symbols and indices used have the meanings given above, and the radicals R on the spirobifluorene preferably stand for H.

In a very particularly preferred embodiment of the invention, the index p=0, and the compound of the formula (1) is selected from the compounds of the following formulae (4a) and (4b):

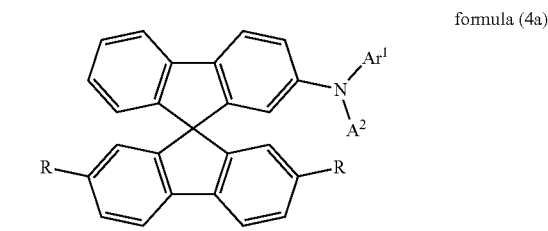

formula (4a)

formula (4b)

where the symbols used have the meanings given above.

The two radicals R in compounds of the formula (4a) or (4b) particularly preferably stand for H. The compound of the formula (1) is therefore particularly preferably selected from the compounds of the following formula (4c):

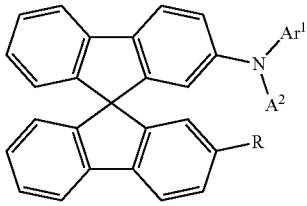

formula (4c)

where the symbols used have the meanings given above.

In a preferred embodiment of the invention, the groups $Ar^1$ and $Ar^2$ are selected, identically or differently on each occurrence, from the groups of the following formulae (5) to (28):

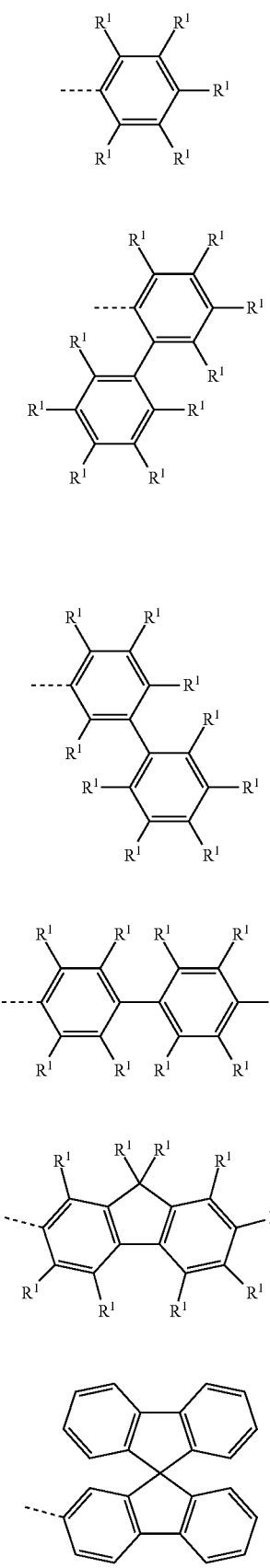
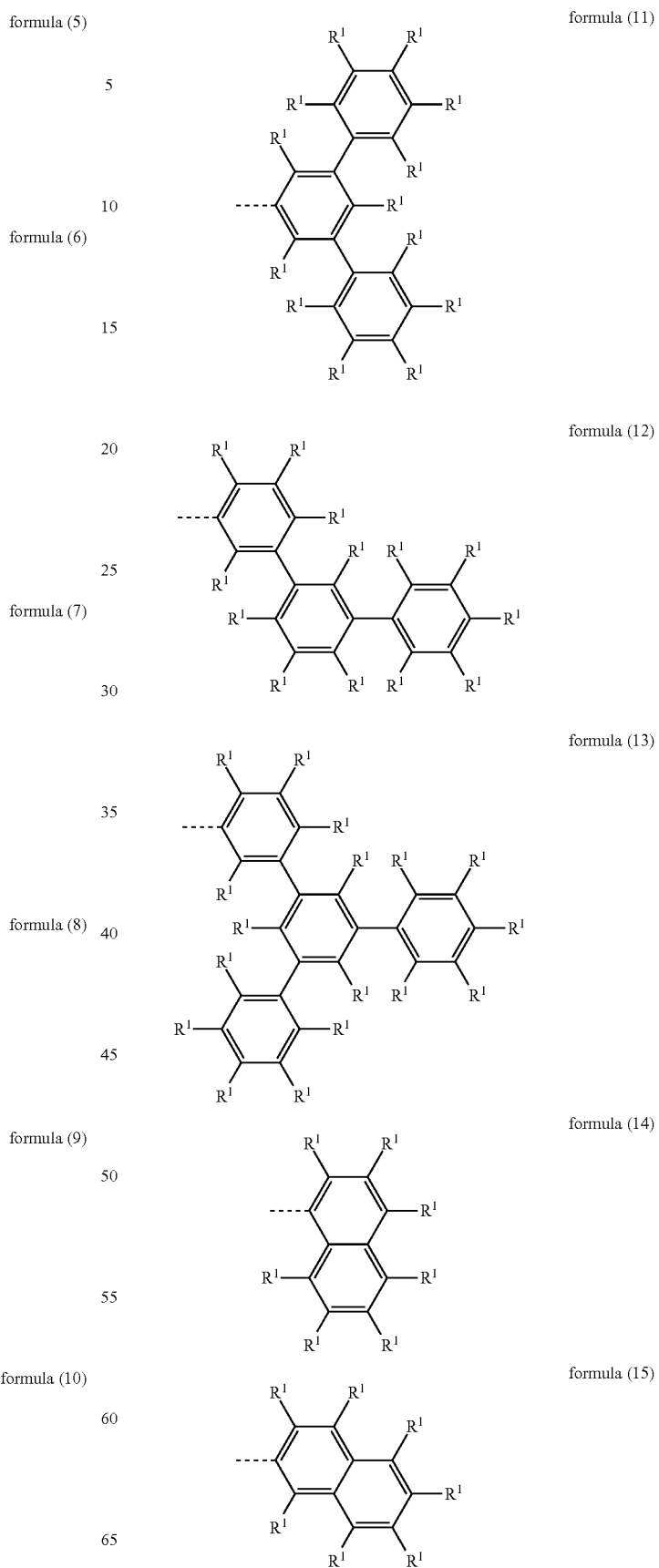

-continued

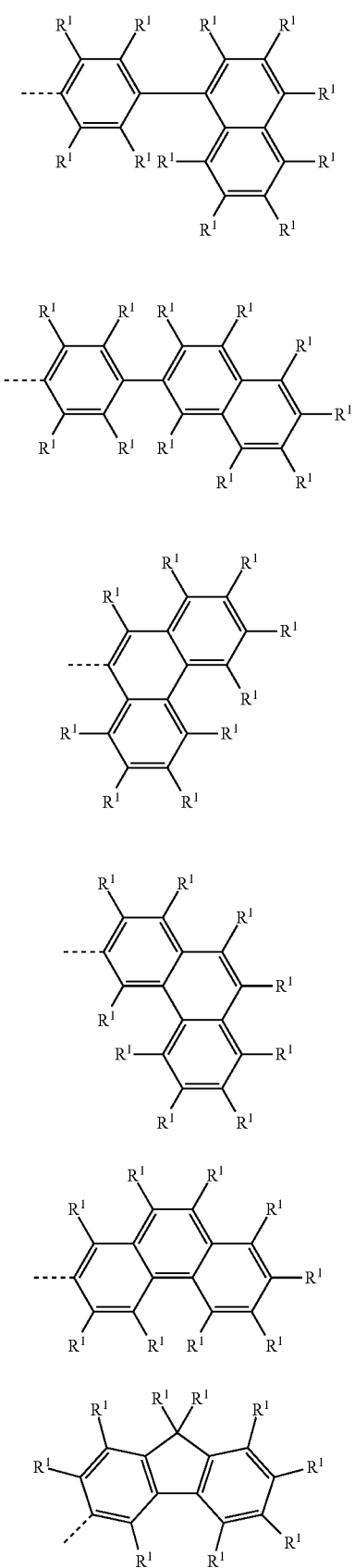

formula (16)

formula (17)

formula (18)

formula (19)

formula (20)

formula (21)

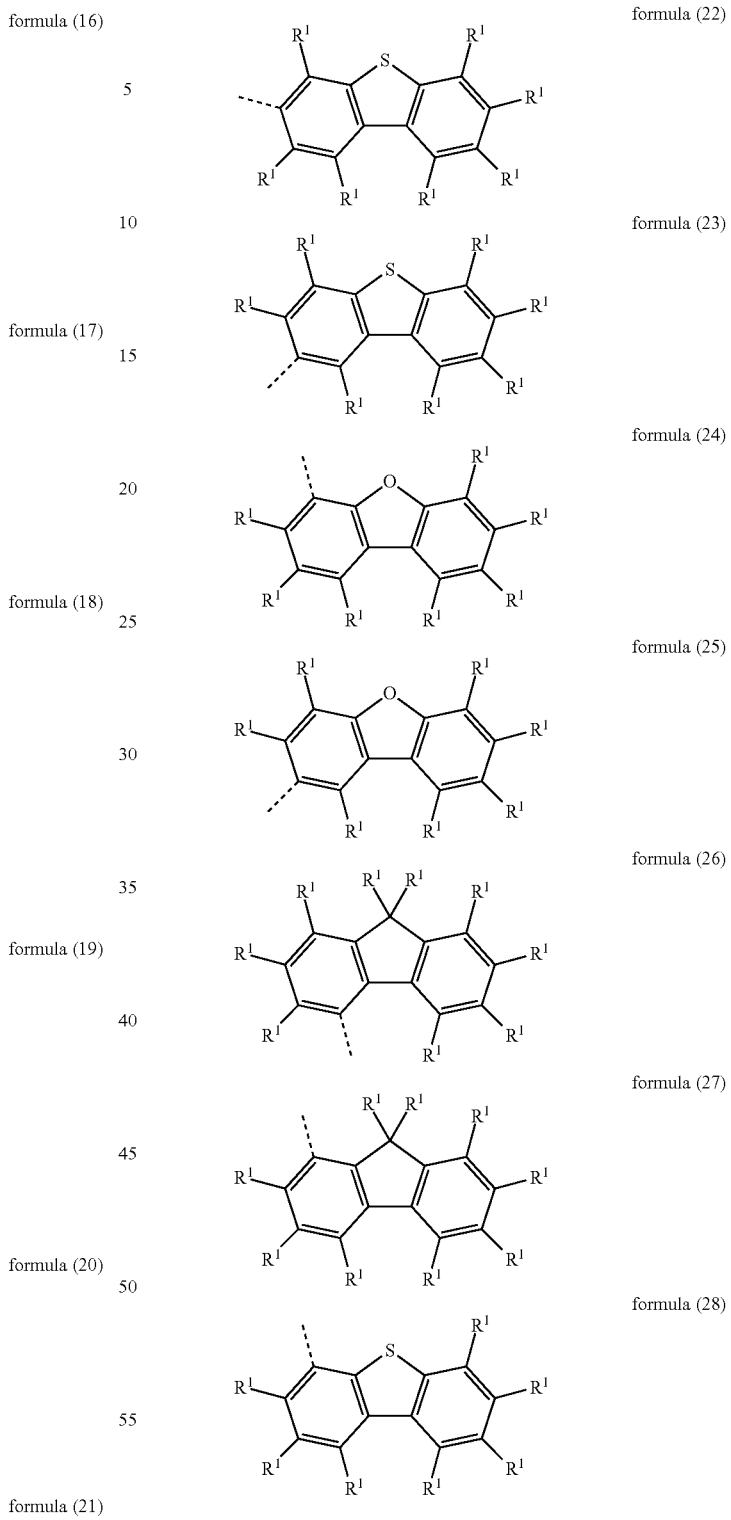

formula (22)

formula (23)

formula (24)

formula (25)

formula (26)

formula (27)

formula (28)

where the symbols used have the meanings given above, and the dashed bond indicates the position of the bond from the group to the nitrogen.

In a particularly preferred embodiment of the invention, the groups $Ar^1$ and $Ar^2$ are selected, identically or differently on each occurrence, from the groups of the following formulae (5a) to (28a):

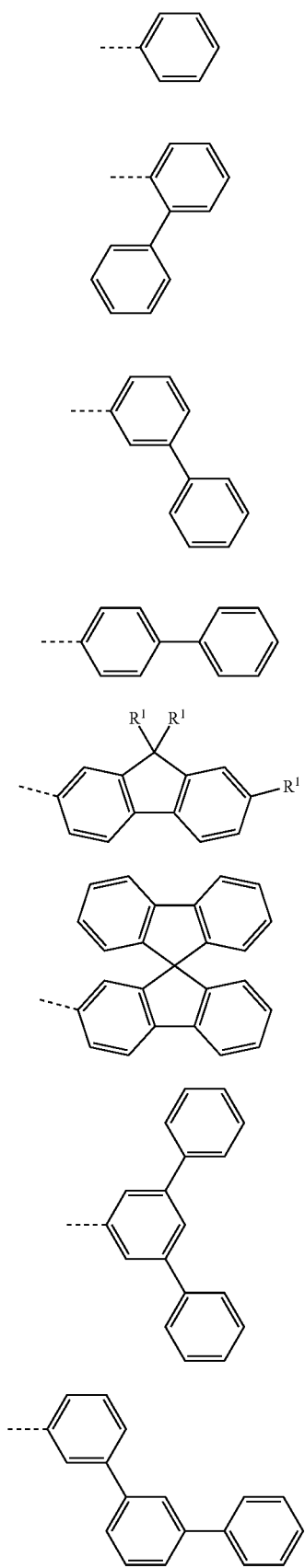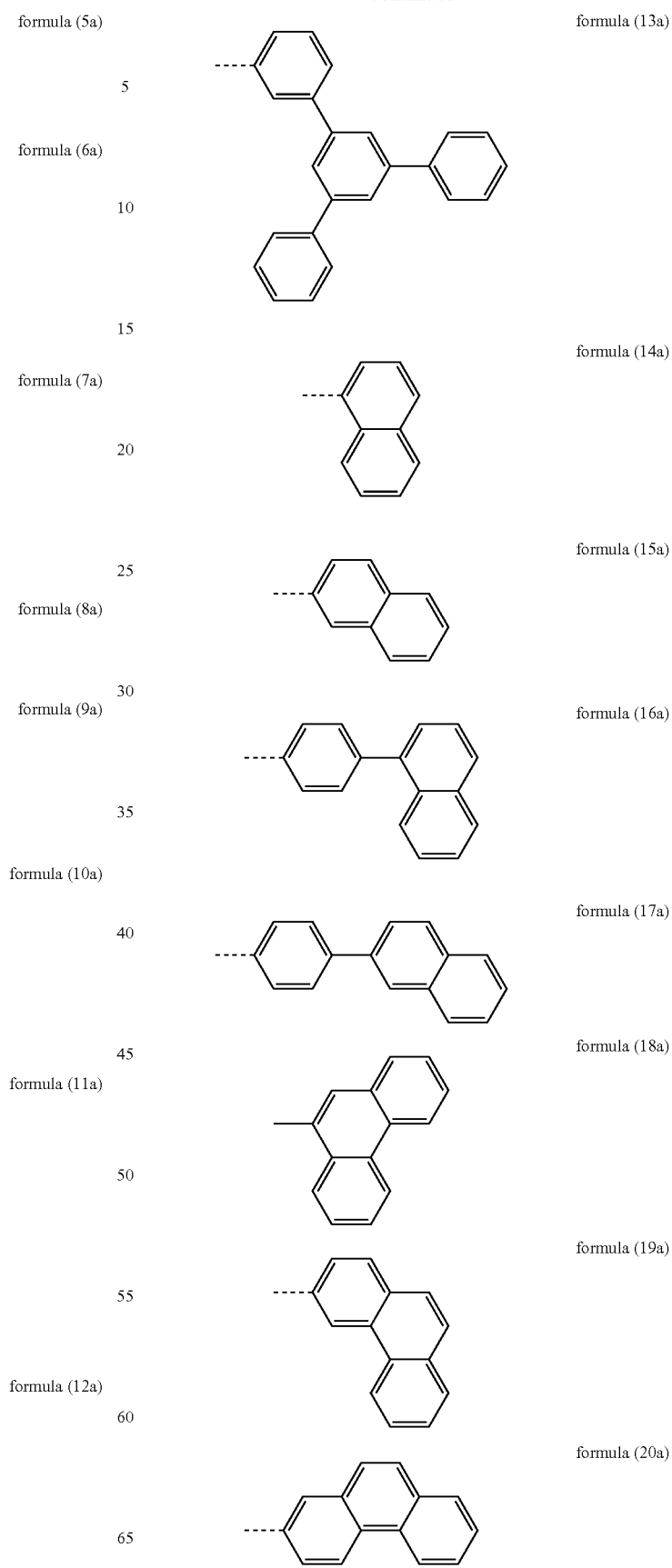

-continued

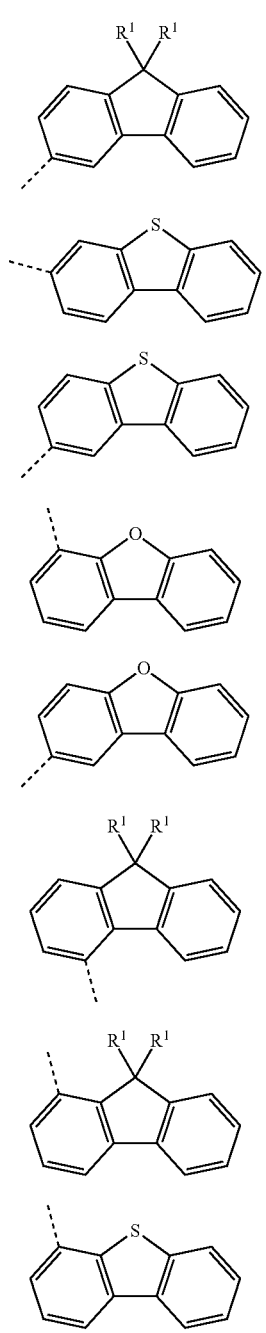

formula (21a)

formula (22a)

formula (23a)

formula (24a)

formula (25a)

formula (26a)

formula (27a)

formula (28a)

where the symbols used have the meanings given above, and the dashed bond indicates the position of the bond from the group to the nitrogen.

The two groups Ar$^1$ and Ar$^2$ of the above-mentioned formulae (5) to (28) and (5a) to (28a) which are bonded to the nitrogen can be combined with one another as desired. The groups of the formulae (5), (6), (7), (8), (9), (10), (11), (12), (13), (21), (22), (23), (24) and (25) or (5a), (6a), (7a), (8a), (9a), (10a), (11a), (12a), (13a), (21a), (22a), (23a), (24a) and (25a) are particularly preferred here.

Particularly preferred groups —NAr$^1$Ar$^2$ are therefore groups which contain the following combinations for Ar$^1$ and Ar$^2$:

| Ar$^1$ | Ar$^2$ |
|---|---|
| formula (5) | formula (5) |
| formula (5) | formula (6) |
| formula (5) | formula (7) |
| formula (5) | formula (8) |
| formula (5) | formula (9) |
| formula (5) | formula (10) |
| formula (5) | formula (11) |
| formula (5) | formula (12) |
| formula (5) | formula (13) |
| formula (5) | formula (21) |
| formula (5) | formula (22) |
| formula (5) | formula (23) |
| formula (5) | formula (24) |
| formula (5) | formula (25) |
| formula (6) | formula (6) |
| formula (6) | formula (7) |
| formula (6) | formula (8) |
| formula (6) | formula (9) |
| formula (6) | formula (10) |
| formula (6) | formula (11) |
| formula (6) | formula (12) |
| formula (6) | formula (13) |
| formula (6) | formula (21) |
| formula (6) | formula (22) |
| formula (6) | formula (23) |
| formula (6) | formula (24) |
| formula (6) | formula (25) |
| formula (7) | formula (7) |
| formula (7) | formula (8) |
| formula (7) | formula (9) |
| formula (7) | formula (10) |
| formula (7) | formula (11) |
| formula (7) | formula (12) |
| formula (7) | formula (13) |
| formula (7) | formula (21) |
| formula (7) | formula (22) |
| formula (7) | formula (23) |
| formula (7) | formula (24) |
| formula (7) | formula (25) |
| formula (8) | formula (8) |
| formula (8) | formula (9) |
| formula (8) | formula (10) |
| formula (8) | formula (11) |
| formula (8) | formula (12) |
| formula (8) | formula (13) |
| formula (8) | formula (21) |
| formula (8) | formula (22) |
| formula (8) | formula (23) |
| formula (8) | formula (24) |
| formula (8) | formula (25) |
| formula (9) | formula (9) |
| formula (9) | formula (10) |
| formula (9) | formula (11) |
| formula (9) | formula (12) |
| formula (9) | formula (13) |
| formula (9) | formula (21) |
| formula (9) | formula (22) |
| formula (9) | formula (23) |
| formula (9) | formula (24) |
| formula (9) | formula (25) |
| formula (10) | formula (10) |
| formula (10) | formula (11) |
| formula (10) | formula (12) |
| formula (10) | formula (13) |
| formula (10) | formula (21) |
| formula (10) | formula (22) |
| formula (10) | formula (23) |
| formula (10) | formula (24) |
| formula (10) | formula (25) |
| formula (11) | formula (11) |
| formula (11) | formula (12) |
| formula (11) | formula (13) |
| formula (11) | formula (21) |
| formula (11) | formula (22) |
| formula (11) | formula (23) |
| formula (11) | formula (24) |
| formula (11) | formula (25) |
| formula (12) | formula (12) |
| formula (12) | formula (13) |

-continued

| Ar¹ | Ar² |
|---|---|
| formula (12) | formula (21) |
| formula (12) | formula (22) |
| formula (12) | formula (23) |
| formula (12) | formula (24) |
| formula (12) | formula (25) |
| formula (13) | formula (13) |
| formula (13) | formula (21) |
| formula (13) | formula (22) |
| formula (13) | formula (23) |
| formula (13) | formula (24) |
| formula (13) | formula (25) |

Very particularly preferred groups —NAr¹Ar² are groups which contain the combinations Ar¹ and Ar² from the table given above in which formulae (5a) to (28a) are employed instead of formulae (5) to (28) respectively.

In a preferred embodiment of the invention, the group Ar¹ is a group of the formula (6), (7), (8), (9) or (21) and in particular a group of the formula (6a), (7a), (8a), (9a) or (21a), in particular (6a) or (9a). Very good results for the organic electroluminescent device are achieved, in particular, with these groups Ar¹. Apart from the combinations indicated in the above table, the following combinations of Ar¹ and Ar² are therefore particularly preferred:

| Ar¹ | Ar² |
|---|---|
| formula (6) | formula (14) |
| formula (6) | formula (15) |
| formula (6) | formula (16) |
| formula (6) | formula (17) |
| formula (6) | formula (18) |
| formula (6) | formula (19) |
| formula (6) | formula (20) |
| formula (6) | formula (26) |
| formula (6) | formula (27) |
| formula (6) | formula (28) |
| formula (9) | formula (14) |
| formula (9) | formula (15) |
| formula (9) | formula (16) |
| formula (9) | formula (17) |
| formula (9) | formula (18) |
| formula (9) | formula (19) |
| formula (9) | formula (20) |
| formula (9) | formula (26) |
| formula (9) | formula (27) |
| formula (9) | formula (28) |

Very particularly preferred groups —NAr¹Ar² are therefore furthermore groups which contain the combinations Ar¹ and Ar² from the table given above in which formula (6a) is employed instead of formula (6) and/or formula (9a) is employed instead of formula (9) and the formulae (14a) to (20a) and (26a) to (28a) are employed correspondingly instead of the formulae (14) to (20) and (26) to (28).

In a preferred embodiment of the invention, the groups Ar¹ and Ar² are different from one another.

In a further preferred embodiment of the invention, at least one of the groups Ar¹ and Ar² is unbridged, i.e. contains neither a fluorene nor a spirobifluorene, i.e. no group of the formula (8), (9) or (21), or (8a), (9a) or (21a) respectively. If the compound of the formulae (1) to (4) is employed as matrix material for green-phosphorescent emitters, both groups Ar¹ and Ar² are preferably unbridged, i.e. contain neither a fluorene nor a spirobifluorene.

In a further preferred embodiment of the invention, the compound of the formula (1), (2), (3a), (3b), (4a), (4b) or (4c) does not contain a spirobifluorene as group Ar¹ or Ar².

If the groups Ar¹ and Ar² in the compounds of the formulae (1), (2), (3a), (3b), (4a), (4b) and (4c) are linked to one another by a group E, the group —NAr¹Ar² then preferably has the structure of one of the following formulae (29), (30), (31) and (32):

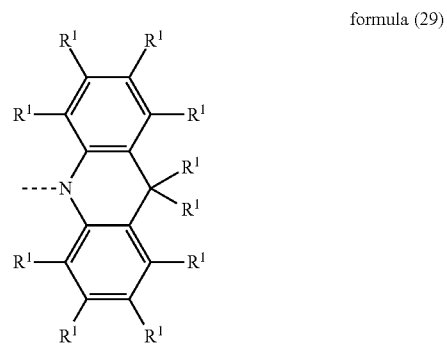

formula (29)

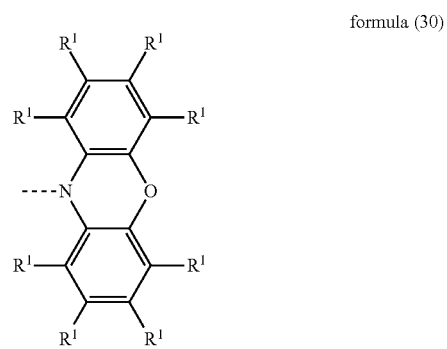

formula (30)

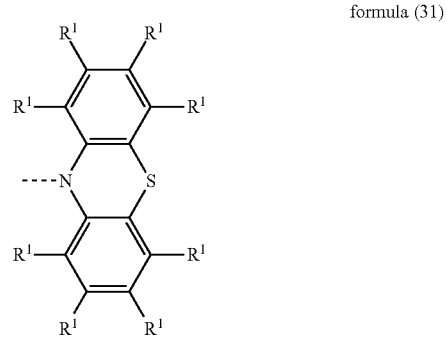

formula (31)

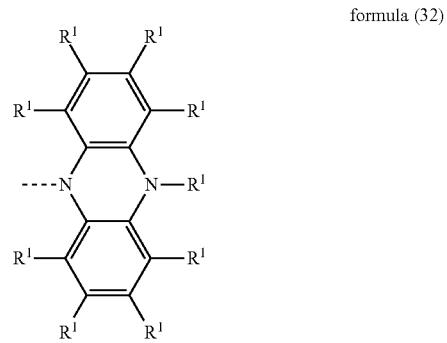

formula (32)

where the symbols used have the meanings given above, and the dashed bond indicates the bond to the spirobifluorene or to Ar.

Preferred embodiments of the formulae (29) to (32) are the following formulae (29a) to (32a):

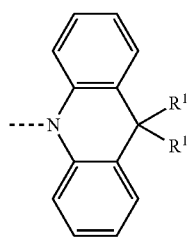
formula (29a)

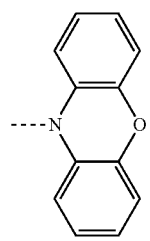
formula (30a)

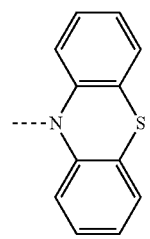
formula (31a)

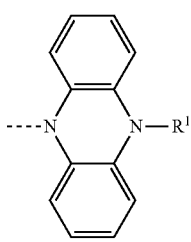
formula (32a)

where the symbols used have the meanings given above, and the dashed bond indicates the bond to the spirobifluorene or to Ar.

If the group Ar is linked to $Ar^1$ by a group E, the group —Ar—$NAr^1Ar^2$ then preferably has the structure of one of the following formulae (33) to (36), and the dashed bond indicates the bond to the spirobifluorene. An analogous situation applies to the linking of the group Ar to $Ar^2$.

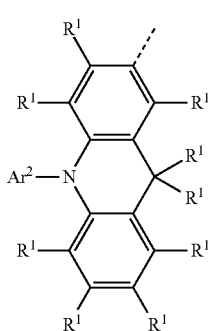
formula (33)

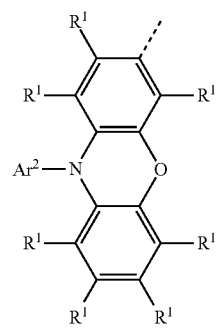
formula (34)

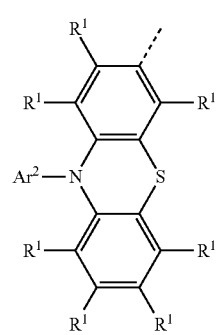
formula (35)

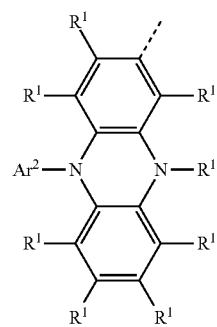
formula (36)

where the symbols used have the meanings given above, and the dashed bond indicates the bond to the spirobifluorene.

Preferred embodiments of the formulae (33) to (36) are the following formulae (33a) to (36a):

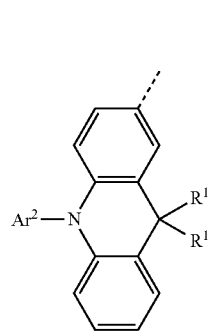
formula (33a)

formula (34a)
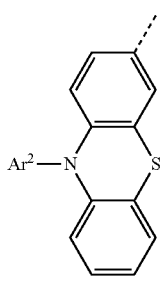
formula (35a)
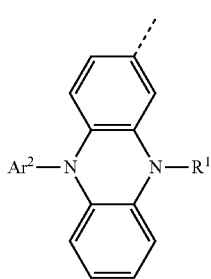
formula (36a)
where the symbols used have the meanings given above, and the dashed bond indicates the bond to the spirobifluorene.
In a further preferred embodiment of the invention, the index p=1 or 2, and the group —(Ar)$_p$— stands for a group of one of the following formulae (37) to (50):
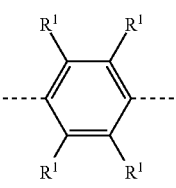
formula (37)
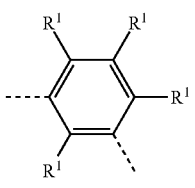
formula (38)
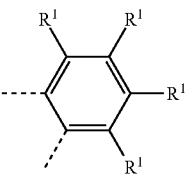
formula (39)
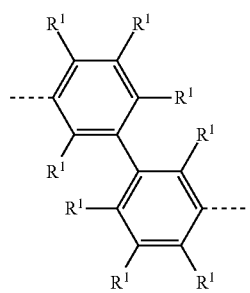
formula (40)
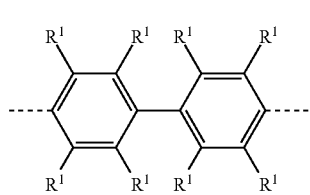
formula (41)
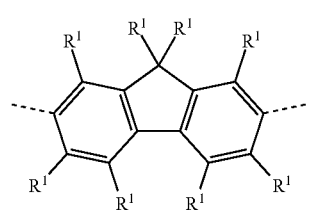
formula (42)
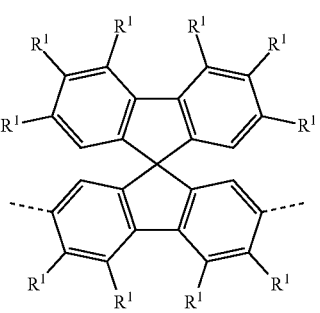
formula (43)
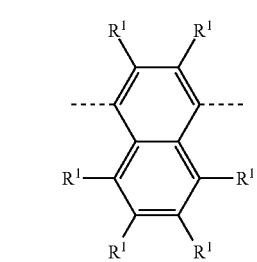
formula (44)
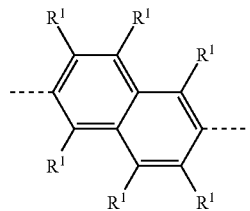
formula (45)

-continued formula (46)

formula (47)

formula (48)

formula (49)

formula (50)

where the symbols used have the meanings given above, and one dashed bond indicates the bond to the spirobifluorene and the other dashed bond indicates the bond to the nitrogen atom.

In a particularly preferred embodiment of the invention, the index p=1 or 2, and the group —(Ar)$_p$— stands for a group of one of the following formulae (37a) to (50a):

formula (37a)

formula (38a)

formula (39a)

formula (40a)

formula (41a)

formula (42a)

formula (43a)

formula (44a)

formula (45a)

formula (46a)

formula (47a)

formula (48a)

formula (49a)

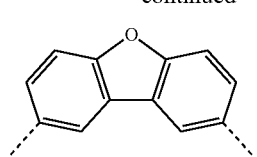

formula (50a)

where the symbols used have the meanings given above, and one dashed bond indicates the bond to the spirobifluorene and the other dashed bond indicates the bond to the nitrogen atom.

In a preferred embodiment of the invention, R in the compounds of the formulae (1) to (4) is selected, identically or differently on each occurrence, from the group consisting of H, D, F, $Si(R^2)_3$, CN, a straight-chain alkyl or alkoxy group having 1 to 10 C atoms or a branched or cyclic alkyl or alkoxy group having 3 to 10 C atoms, each of which may be substituted by one or more radicals $R^2$, where one or more non-adjacent $CH_2$ groups may be replaced by O and where one or more H atoms may be replaced by D or F, an aromatic ring system having 6 to 60 C atoms selected from the group consisting of benzene, naphthalene, phenanthrene, fluorene, spirobifluorene or a combination of two, three or four of these groups, which may in each case be identical or different, which may in each case be substituted by one or more radicals $R^2$, where two or more adjacent substituents R may optionally form a mono- or polycyclic, aliphatic ring system, which may be substituted by one or more radicals $R^2$.

In a particularly preferred embodiment of the invention, R in the compounds of the formulae (1) to (4) is selected, identically or differently on each occurrence, from the group consisting of H, D, a straight-chain alkyl group having 1 to 10 C atoms or a branched or cyclic alkyl group having 3 to 10 C atoms, each of which may be substituted by one or more radicals $R^2$, an aromatic ring system having 6 to 60 C atoms selected from the group consisting of benzene, naphthalene, phenanthrene, fluorene, spirobifluorene or a combination of two or three of these groups, which may in each case be identical or different, which may in each case be substituted by one or more radicals $R^2$, where two or more adjacent substituents R may optionally form a mono- or polycyclic, aliphatic ring system, which may be substituted by one or more radicals $R^2$.

In a very particularly preferred embodiment of the invention, R in the compounds of the formulae (1) to (4) is equal to H.

In a further preferred embodiment of the invention, the radical $R^1$ bonded to $Ar^1$ or $Ar^2$ or Ar is selected, identically or differently on each occurrence, from the group consisting of H, D, a straight-chain alkyl group having 1 to 10 C atoms or a branched or cyclic alkyl group having 3 to 10 C atoms.

In a further preferred embodiment of the invention, at least one radical $R^1$ bonded in the ortho-position of the aryl group of $Ar^1$ or $Ar^2$ which is bonded directly to the nitrogen is not equal to hydrogen or deuterium. This applies, in particular, if a further aryl group is not already bonded in the ortho-position of the aryl group, as is the case, for example, in formula (6).

It may furthermore be preferred for the two substituents $R^1$ in the 9-position of a fluorene to form a cycloalkyl ring together, preferably having 3 to 8 C atoms, particularly preferably having 5 or 6 C atoms.

In a further preferred embodiment, $R^1$, which is bonded to the carbon bridge in formula (29) or (33), is selected, identically or differently on each occurrence, from the group consisting of a straight-chain alkyl group having 1 to 10 C atoms, a branched or cyclic alkyl group having 3 to 10 C atoms or an aromatic ring system having 6 to 30 C atoms, which is as defined above and which may be substituted by one or more radicals $R^2$. The two groups $R^1$ here may also form with one another a ring system, which may be aliphatic or also aromatic in addition to the definition of $R^1$ given above. A spiro system is formed by ring formation.

In a further preferred embodiment, $R^1$, which is bonded to the nitrogen bridge in formula (32) or (36), is selected from the group consisting of a straight-chain alkyl group having 1 to 10 C atoms, a branched or cyclic alkyl group having 3 to 10 C atoms or an aromatic ring system having 6 to 30 C atoms, in particular an aromatic ring system having 6 to 24 C atoms, which is as defined above and which may be substituted by one or more radicals $R^2$.

For compounds which are processed by vacuum evaporation, the alkyl groups preferably have not more than four C atoms, particularly preferably not more than 1 C atom. For compounds which are processed from solution, suitable compounds are also those which are substituted by linear, branched or cyclic alkyl groups having up to 10 C atoms or which are substituted by oligoarylene groups, for example ortho-, meta-, para- or branched terphenyl or quaterphenyl groups.

In a preferred embodiment of the invention, $R^2$ is selected, identically or differently on each occurrence, from the group consisting of H, D, a straight-chain alkyl group having 1 to 10 C atoms or a branched or cyclic alkyl group having 3 to 10 C atoms or an aromatic ring system having 6 to C atoms, which is as defined above and which may in each case be substituted by one or more radicals $R^3$.

In a particularly preferred embodiment of the invention, $R^2$ is selected, identically or differently on each occurrence, from the group consisting of H, D, a straight-chain alkyl group having 1 to 5 C atoms or a branched or cyclic alkyl group having 3 to 5 C atoms, or an aromatic ring system having 6 to 18 C atoms, which is as defined above.

Particular preference is given to compounds of the formulae (1), (2), (3a), (3b), (4a), (4b) and (4c) in which the preferred embodiments mentioned above occur simultaneously. Particular preference is therefore given to compounds for which:

Ar is, identically or differently on each occurrence, an aromatic ring system, where, for p=1 or 2, —(Ar)$_p$— is selected from the groups of the formulae (37) to (50); Ar here may also be connected to Ar$^1$ and/or Ar$^2$ by a group E;

Ar$^1$, Ar$^2$ are, identically or differently on each occurrence, an aromatic ring system selected from the groups of the formulae (5) to (28); or —NAr$^1$Ar$^2$ stands for a group of one of the formulae (29) to (32); or —Ar—NAr$^1$Ar$^2$ stands for a group of one of the formulae (33) to (36);

E is on each occurrence, identically or differently, C(R$^1$)$_2$, N(R$^1$), O or S;

R is selected on each occurrence, identically or differently, from the group consisting of H, D, F, Si(R$^2$)$_3$, a straight-chain alkyl or alkoxy group having 1 to 10 C atoms or a branched or cyclic alkyl or alkoxy group having 3 to 10 C atoms, each of which may be substituted by one or more radicals R$^2$, where one or more non-adjacent CH$_2$ groups may be replaced by O and where one or more H atoms may be replaced by D or F, an aromatic ring system having 6 to 60 C atoms selected from the group consisting of benzene, naphthalene, phenanthrene, fluorene, spirobifluorene or a combination of two or three of these groups, which may in each case be identical or different, which may in each case be substituted by one or more radicals R$^2$, where two or more adjacent substituents R may optionally form a mono- or polycyclic, aliphatic ring system, which may be substituted by one or more radicals R$^2$;

R$^1$ is, if the radical R$^1$ is bonded to Ar$^1$ or Ar$^2$, selected, identically or differently on each occurrence, from the group consisting of H, D, a straight-chain alkyl group having 1 to 10 C atoms or a branched or cyclic alkyl group having 3 to 10 C atoms;

or R$^1$ which is bonded to the carbon bridge in formula (29) or (33) is selected, identically or differently on each occurrence, from the group consisting of a straight-chain alkyl group having 1 to 10 C atoms, a branched or cyclic alkyl group having 3 to 10 C atoms or an aromatic ring system having 6 to 30 C atoms, which may be substituted by one or more radicals R$^2$; the two radicals R$^1$ here may also form an aliphatic or aromatic ring system with one another;

or R$^1$ which is bonded to the nitrogen bridge in formula (32) or (36) is selected from the group consisting of a straight-chain alkyl group having 1 to 10 C atoms, a branched or cyclic alkyl group having 3 to 10 C atoms or an aromatic ring system having 6 to 30 C atoms, which may be substituted by one or more radicals R$^2$;

R$^2$ is selected on each occurrence, identically or differently, from the group consisting of H, D, a straight-chain alkyl group having 1 to 5 C atoms or a branched or cyclic alkyl group having 3 to 5 C atoms, or an aromatic ring system having 6 to 18 C atoms;

R$^3$ is selected from the group consisting of H, D, F, an aliphatic hydrocarbon radical having 1 to 10 C atoms, an aromatic ring system having 6 to 24 C atoms, in which one or more H atoms may be replaced by D or F, where two or more adjacent substituents R$^3$ may form a mono- or polycyclic, aliphatic, aromatic or heteroaromatic ring system with one another;

m is 0, 1 or 2;

n is on each occurrence, identically or differently, 0, 1 or 2;

p is 0, 1 or 2.

Very particular preference is given to compounds of the formulae (1), (2), (3a), (3b), (4a), (4b) and (4c) for which:

Ar is, identically or differently on each occurrence, an aromatic ring system, where, for p=1 or 2, —(Ar)$_p$— is selected from the groups of the formulae (37a) to (50a); Ar here may also be connected to Ar$^1$ or Ar$^2$ by a group E;

Ar$^1$, Ar$^2$ are, identically or differently on each occurrence, an aromatic ring system selected from the groups of the formulae (5a) to (28a), where at least one group Ar$^1$ and/or Ar$^2$ represents an unbridged group;

or —NAr$^1$Ar$^2$ stands for a group of one of the formulae (29a) to (32a);

or —Ar—NAr$^1$Ar$^2$ stands for a group of one of the formulae (33a) to (36a);

E is on each occurrence, identically or differently, C(R$^1$)$_2$, NR$^1$, O or S;

R is selected on each occurrence, identically or differently, from the group consisting of H, D, a straight-chain alkyl group having 1 to 10 C atoms or a branched or cyclic alkyl group having 3 to 10 C atoms, each of which may be substituted by one or more radicals R$^2$, an aromatic ring system having 6 to 60 C atoms selected from the group consisting of benzene, naphthalene, phenanthrene, fluorene, spirobifluorene or a combination of two of these groups, which may in each case be identical or different, which may in each case be substituted by one or more radicals R$^2$, where two or more adjacent substituents R may optionally form a mono- or polycyclic, aliphatic ring system, which may be substituted by one or more radicals R$^2$; R is preferably equal to H;

R$^1$ is, if the radical R$^1$ is bonded to Ar$^1$ or Ar$^2$, selected, identically or differently on each occurrence, from the group consisting of H, D, a straight-chain alkyl group having 1 to 5 C atoms or a branched or cyclic alkyl group having 3 to 5 C atoms;

or R$^1$ which is bonded to the carbon bridge in formula (29) or (33) is selected, identically or differently on each occurrence, from the group consisting of a straight-chain alkyl group having 1 to 10 C atoms, a branched or cyclic alkyl group having 3 to 10 C atoms or an aromatic ring system having 6 to 30 C atoms, which may be substituted by one or more radicals R$^2$; the two radicals R$^1$ here may also form an aliphatic or aromatic ring system with one another;

or R$^1$ which is bonded to the nitrogen bridge in formula (32) or (36) is selected from the group consisting of a straight-chain alkyl group having 1 to 10 C atoms, a branched or cyclic alkyl group having 3 to 10 C atoms or an aromatic ring system having 6 to 24 C atoms, which may be substituted by one or more radicals R$^2$;

R$^2$ is selected on each occurrence, identically or differently, from the group consisting of H, D, a straight-chain alkyl group having 1 to 5 C atoms or a branched or cyclic alkyl group having 3 to 5 C atoms, or an aromatic ring system having 6 to 18 C atoms;

R$^3$ is selected from the group consisting of H, D, F, an aliphatic hydrocarbon radical having 1 to 5 C atoms, an aromatic ring system having 6 to 12 C atoms, in which one or more H atoms may be replaced by D or F, where two or more adjacent substituents R$^3$ may form a mono- or polycyclic, aliphatic, aromatic or heteroaromatic ring system with one another;

m is 0;

n is on each occurrence, identically or differently, 0 or 1;

p is 0, 1 or 2.

Examples of suitable compounds according to the invention are the compounds shown in the following table:

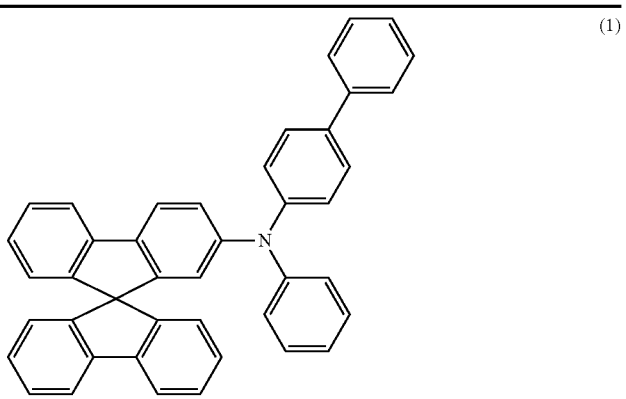
(1)
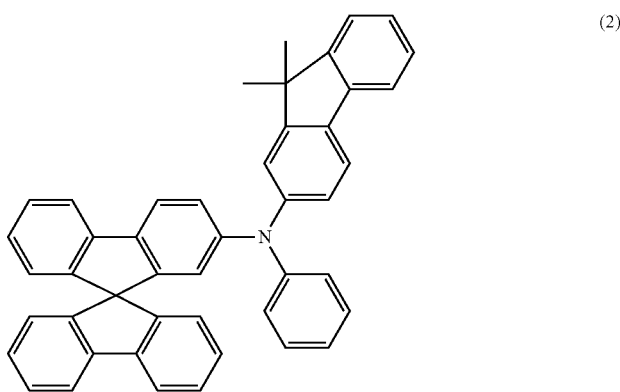
(2)
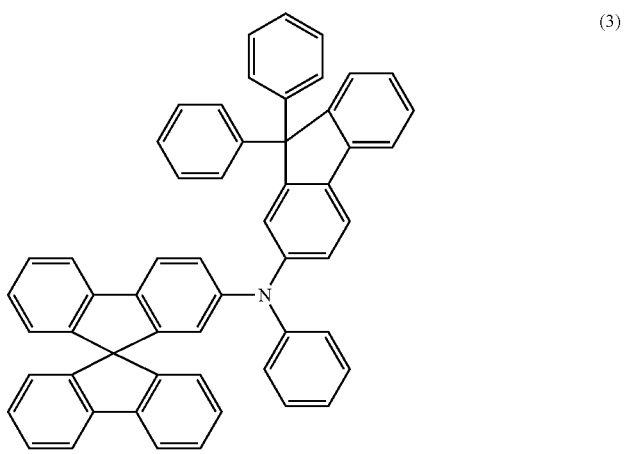
(3)
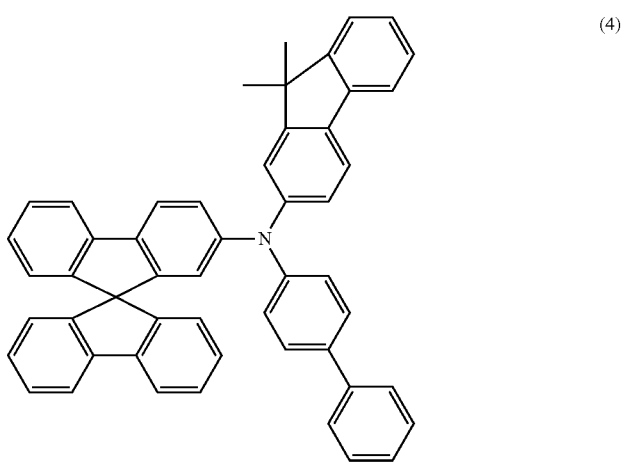
(4)

-continued
(5)
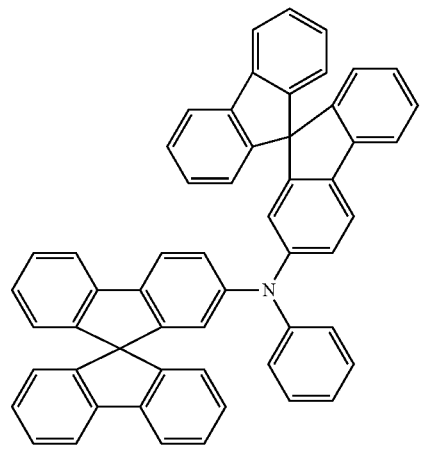 [SMILES: c1ccc(N(c2ccc3c(c2)C2(c4ccccc4-c4ccccc42)c2ccccc2-3)c2ccc3c(c2)C2(c4ccccc4-c4ccccc42)c2ccccc2-3)cc1]
(6)
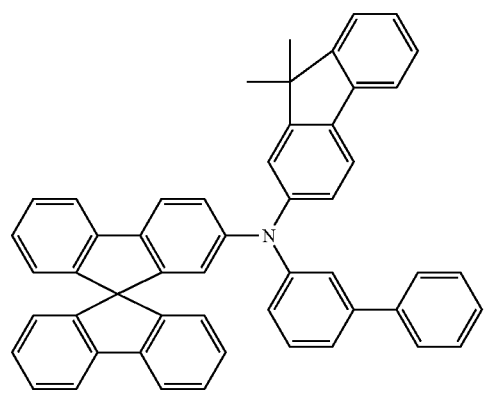 [SMILES: CC1(C)c2ccccc2-c2ccc(N(c3cccc(-c4ccccc4)c3)c3ccc4c(c3)C3(c5ccccc5-c5ccccc53)c3ccccc3-4)cc21]
(7)
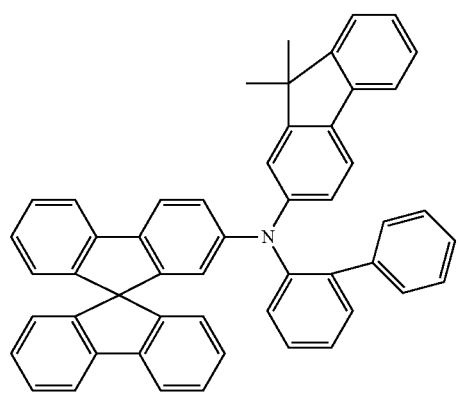 [SMILES: CC1(C)c2ccccc2-c2ccc(N(c3ccc4c(c3)C3(c5ccccc5-c5ccccc53)c3ccccc3-4)c3ccccc3-c3ccccc3)cc21]

-continued
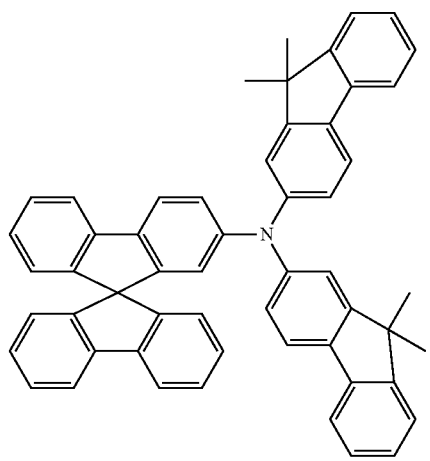
(8)
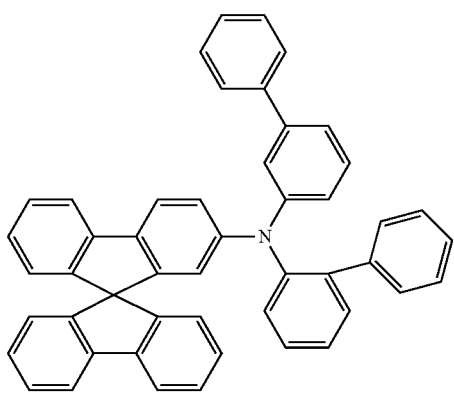 [SMILES: c1ccc(-c2cccc(N(c3ccc4c(c3)C3(c5ccccc5-c5ccccc53)c3ccccc3-4)c3ccccc3-c3ccccc3)c2)cc1]
(9)
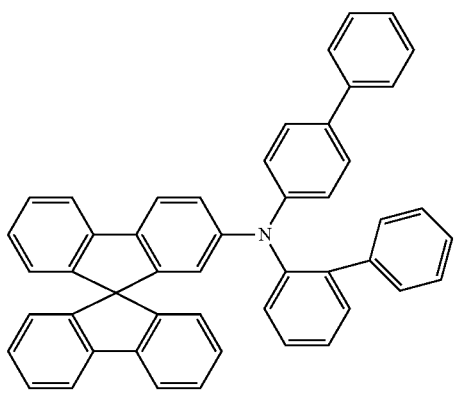 [SMILES: c1ccc(-c2ccc(N(c3ccc4c(c3)C3(c5ccccc5-c5ccccc53)c3ccccc3-4)c3ccccc3-c3ccccc3)cc2)cc1]
(10)
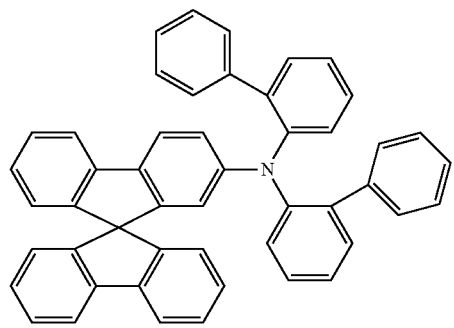 [SMILES: c1ccc(-c2ccccc2N(c2ccc3c(c2)C2(c4ccccc4-c4ccccc42)c2ccccc2-3)c2ccccc2-c2ccccc2)cc1]
(11)

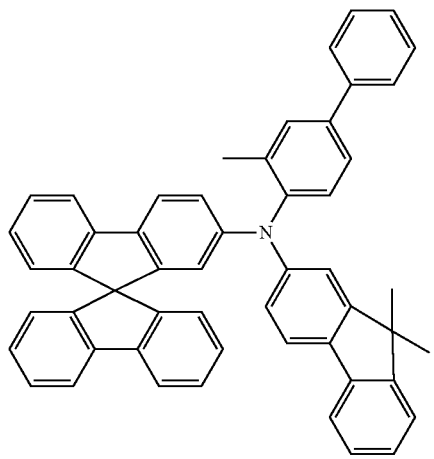 [SMILES: Cc1cc(-c2ccccc2)ccc1N(c1ccc2c(c1)C(C)(C)c1ccccc1-2)c1ccc2c(c1)C1(c3ccccc3-c3ccccc31)c1ccccc1-2]
(12)
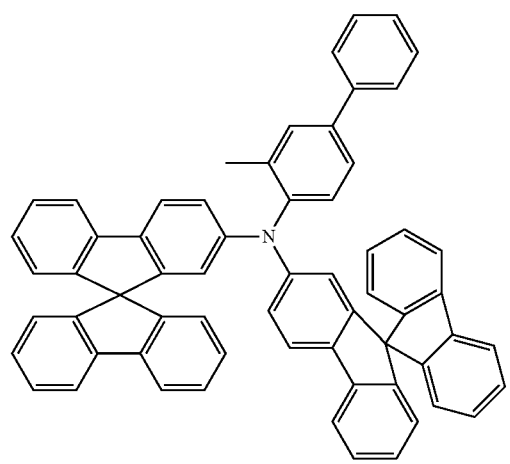 [SMILES: Cc1cc(-c2ccccc2)ccc1N(c1ccc2c(c1)C1(c3ccccc3-c3ccccc31)c1ccccc1-2)c1ccc2c(c1)C1(c3ccccc3-c3ccccc31)c1ccccc1-2]
(13)
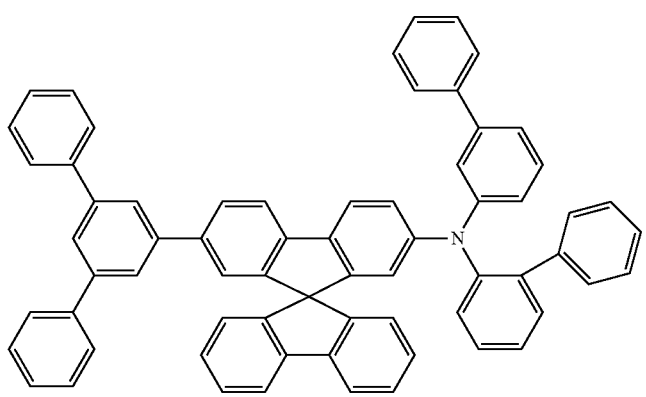 [SMILES: c1ccc(-c2cc(-c3ccccc3)cc(-c3ccc4c(c3)C3(c5ccccc5-c5ccccc53)c3cc(N(c5cccc(-c6ccccc6)c5)c5ccccc5-c5ccccc5)ccc3-4)c2)cc1]
(14)

-continued
(15)
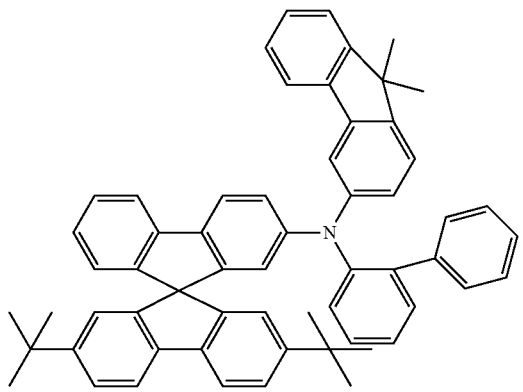 [SMILES: CC(C)(C)c1ccc2c(c1)C1(c3ccccc3-c3ccc(N(c4ccc5c(c4)-c4ccccc4C5(C)C)c4ccccc4-c4ccccc4)cc31)c1cc(C(C)(C)C)ccc1-2]
(16)
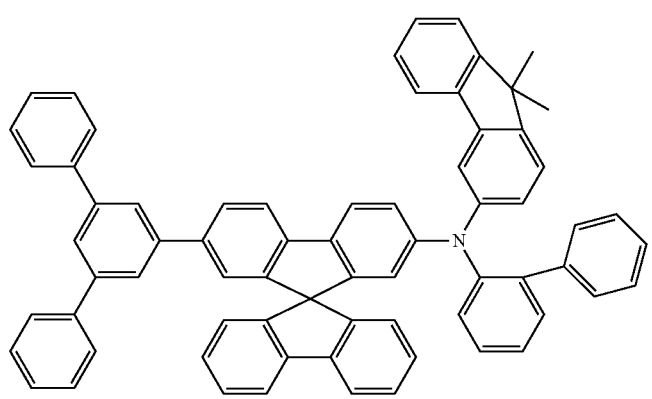 [SMILES: CC1(C)c2ccccc2-c2cc(N(c3ccc4c(c3)C3(c5ccccc5-c5ccccc53)c3cc(-c5cc(-c6ccccc6)cc(-c6ccccc6)c5)ccc3-4)c3ccccc3-c3ccccc3)ccc21]
(17)
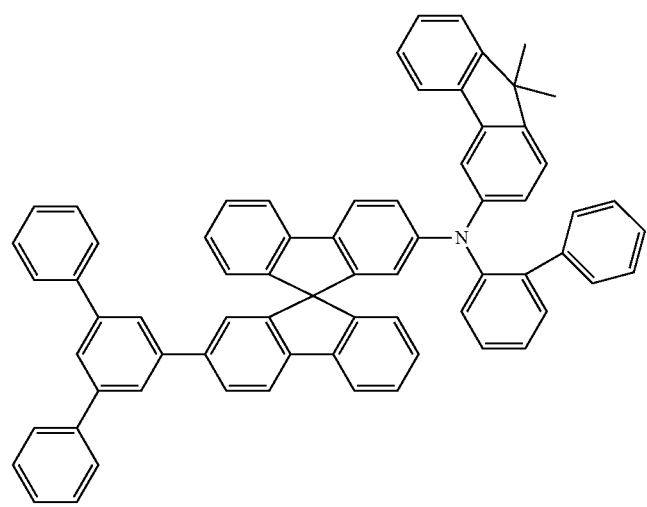 [SMILES: CC1(C)c2ccccc2-c2cc(N(c3ccc4c(c3)C3(c5ccccc5-c5ccc(-c6cc(-c7ccccc7)cc(-c7ccccc7)c6)cc53)c3ccccc3-4)c3ccccc3-c3ccccc3)ccc21]
(18)
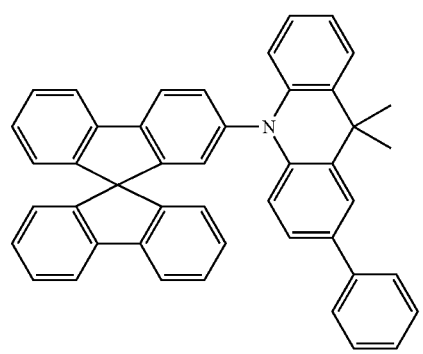 [SMILES: CC1(C)c2ccccc2N(c2ccc3c(c2)C2(c4ccccc4-c4ccccc42)c2ccccc2-3)c2ccc(-c3ccccc3)cc21]

(19)
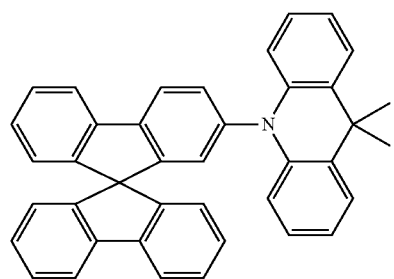 [SMILES: CC1(C)c2ccccc2N(c2ccc3c(c2)C2(c4ccccc4-c4ccccc42)c2ccccc2-3)c2ccccc21]
(20)
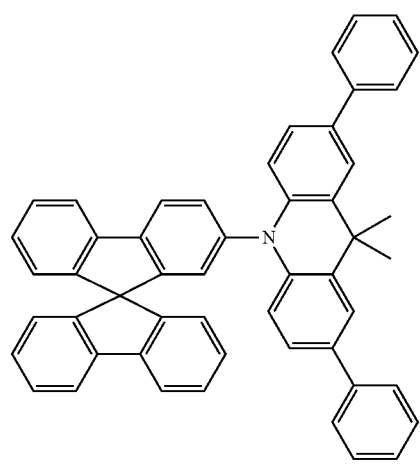 [SMILES: CC1(C)c2cc(-c3ccccc3)ccc2N(c2ccc3c(c2)C2(c4ccccc4-c4ccccc42)c2ccccc2-3)c2ccc(-c3ccccc3)cc21]
(21)
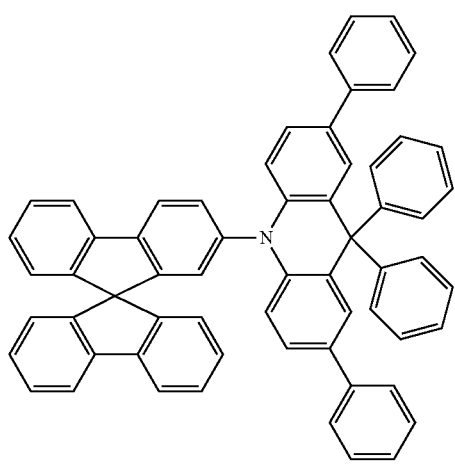 [SMILES: c1ccc(-c2ccc3c(c2)C(c2ccccc2)(c2ccccc2)c2cc(-c4ccccc4)ccc2N3c2ccc3c(c2)C2(c4ccccc4-c4ccccc42)c2ccccc2-3)cc1]
(22)
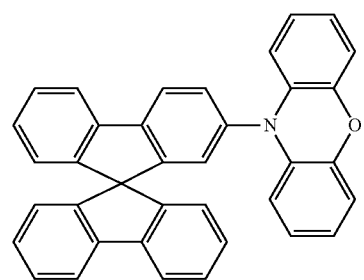 [SMILES: c1ccc2c(c1)Oc1ccccc1N2c1ccc2c(c1)C1(c3ccccc3-c3ccccc31)c1ccccc1-2]

-continued
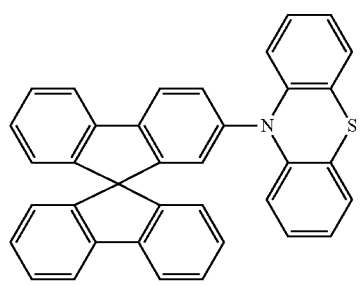 [SMILES: c1ccc2c(c1)Sc1ccccc1N2c1ccc2c(c1)C1(c3ccccc3-c3ccccc31)c1ccccc1-2]
(23)
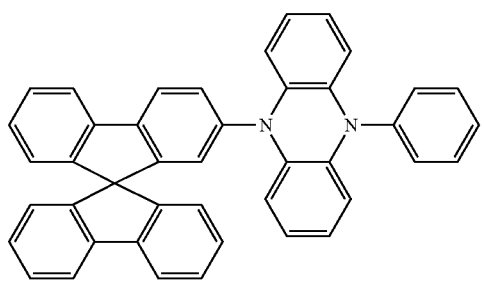 [SMILES: c1ccc(N2c3ccccc3N(c3ccc4c(c3)C3(c5ccccc5-c5ccccc53)c3ccccc3-4)c3ccccc32)cc1]
(24)
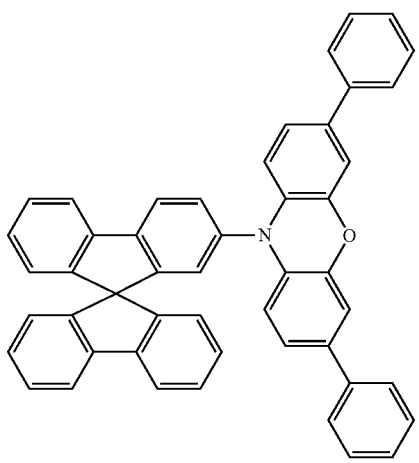
(25)
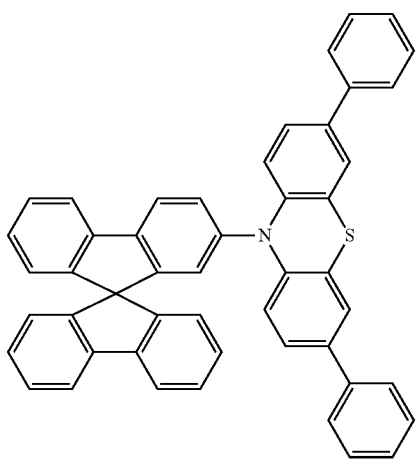 [SMILES: c1ccc(-c2ccc3c(c2)Oc2cc(-c4ccccc4)ccc2N3c2ccc3c(c2)C2(c4ccccc4-c4ccccc42)c2ccccc2-3)cc1]
(26)

-continued
(27)
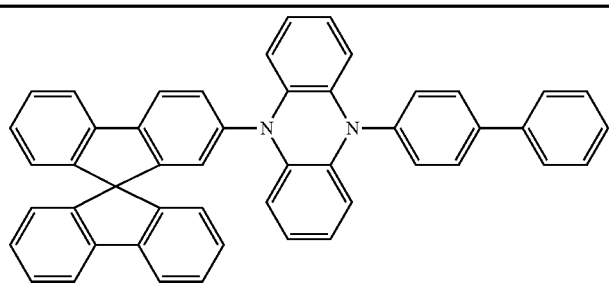
(28)
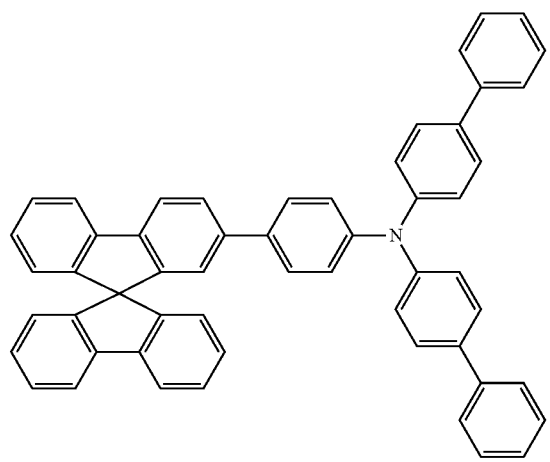 [SMILES: c1ccc(-c2ccc(N(c3ccc(-c4ccccc4)cc3)c3ccc(-c4ccc5c(c4)C4(c6ccccc6-c6ccccc64)c4ccccc4-5)cc3)cc2)cc1]
(29)
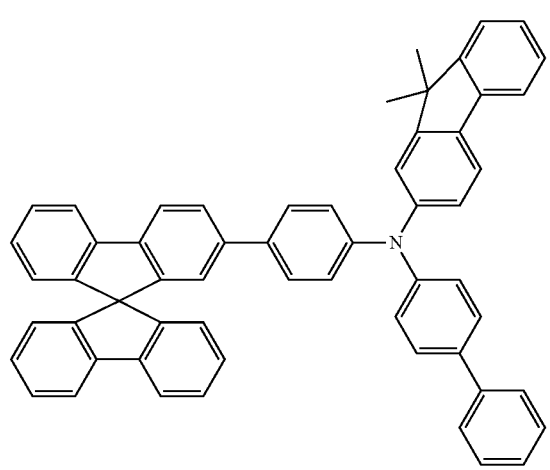 [SMILES: CC1(C)c2ccccc2-c2ccc(N(c3ccc(-c4ccccc4)cc3)c3ccc(-c4ccc5c(c4)C4(c6ccccc6-c6ccccc64)c4ccccc4-5)cc3)cc21]
(30)
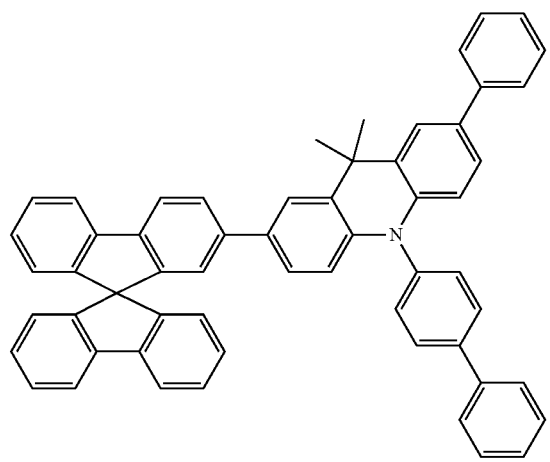 [SMILES: CC1(C)c2cc(-c3ccccc3)ccc2N(c2ccc(-c3ccccc3)cc2)c2ccc(-c3ccc4c(c3)C3(c5ccccc5-c5ccccc53)c3ccccc3-4)cc21]

-continued
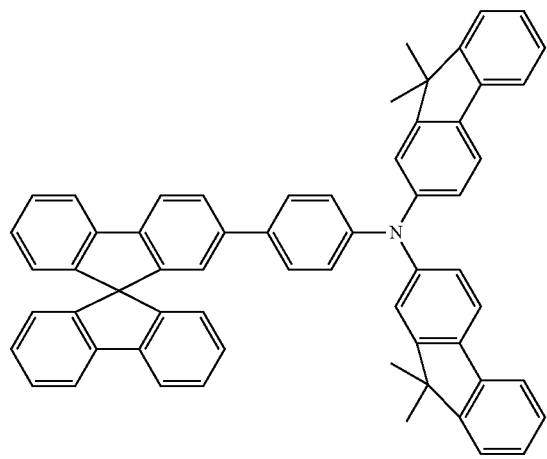 [SMILES: CC1(C)c2ccccc2-c2ccc(N(c3ccc(-c4ccc5c(c4)C4(c6ccccc6-c6ccccc64)c4ccccc4-5)cc3)c3ccc4c(c3)C(C)(C)c3ccccc3-4)cc21]
(31)
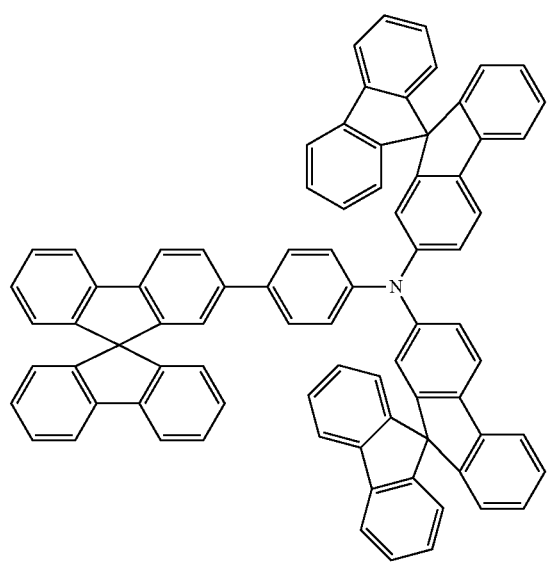 [SMILES: c1ccc2c(c1)-c1ccccc1C21c2ccccc2-c2ccc(-c3ccc(N(c4ccc5c(c4)C4(c6ccccc6-c6ccccc64)c4ccccc4-5)c4ccc5c(c4)C4(c6ccccc6-c6ccccc64)c4ccccc4-5)cc3)cc21]
(32)
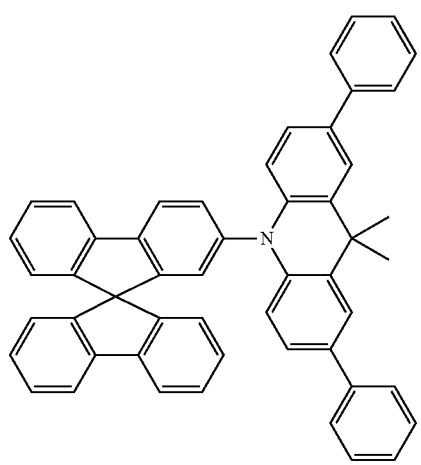 [SMILES: CC1(C)c2cc(-c3ccccc3)ccc2N(c2ccc3c(c2)C2(c4ccccc4-c4ccccc42)c2ccccc2-3)c2ccc(-c3ccccc3)cc21]
(33)

(34)
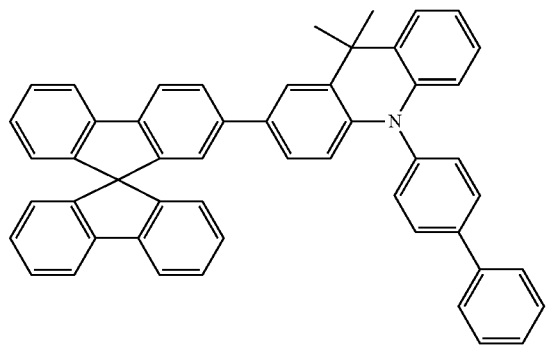 [SMILES: CC1(C)c2ccccc2N(c2ccc(-c3ccccc3)cc2)c2ccc(-c3ccc4c(c3)C3(c5ccccc5-c5ccccc53)c3ccccc3-4)cc21]
(35)
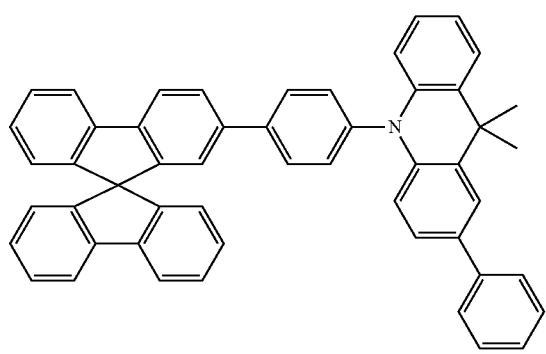 [SMILES: CC1(C)c2ccccc2N(c2ccc(-c3ccc4c(c3)C3(c5ccccc5-c5ccccc53)c3ccccc3-4)cc2)c2ccc(-c3ccccc3)cc21]
(36)
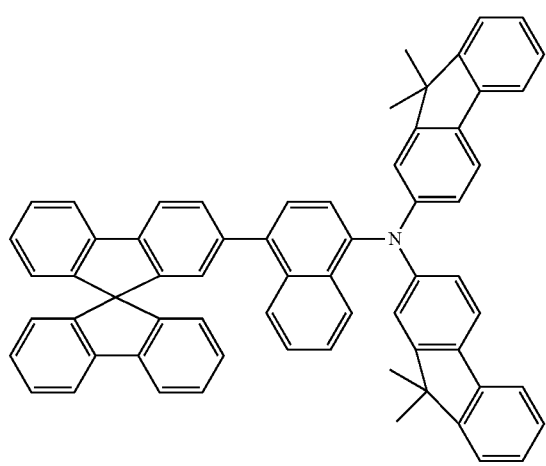 [SMILES: CC1(C)c2ccccc2-c2ccc(N(c3ccc4c(c3)C(C)(C)c3ccccc3-4)c3ccc(-c4ccc5c(c4)C4(c6ccccc6-c6ccccc64)c4ccccc4-5)c4ccccc34)cc21]
(37)
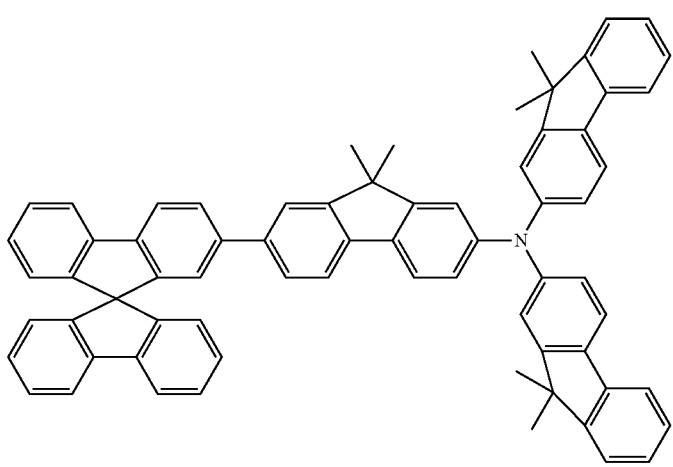 [SMILES: CC1(C)c2ccccc2-c2ccc(N(c3ccc4c(c3)C(C)(C)c3ccccc3-4)c3ccc4c(c3)C(C)(C)c3cc(-c5ccc6c(c5)C5(c7ccccc7-c7ccccc75)c5ccccc5-6)ccc3-4)cc21]

-continued
(38)
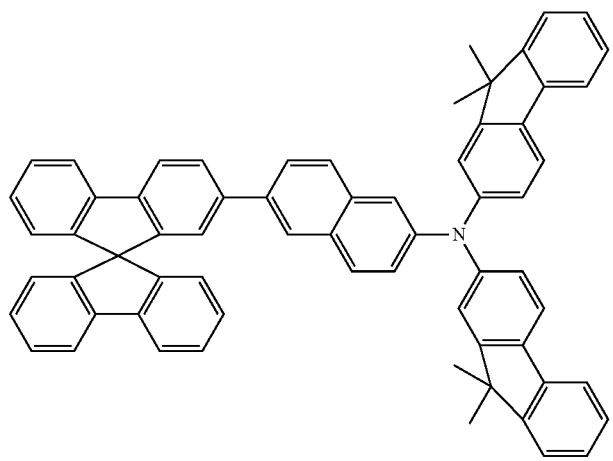 [SMILES: CC1(C)c2ccccc2-c2ccc(N(c3ccc4c(c3)C(C)(C)c3ccccc3-4)c3ccc4cc(-c5ccc6c(c5)C5(c7ccccc7-c7ccccc75)c5ccccc5-6)ccc4c3)cc21]
(39)
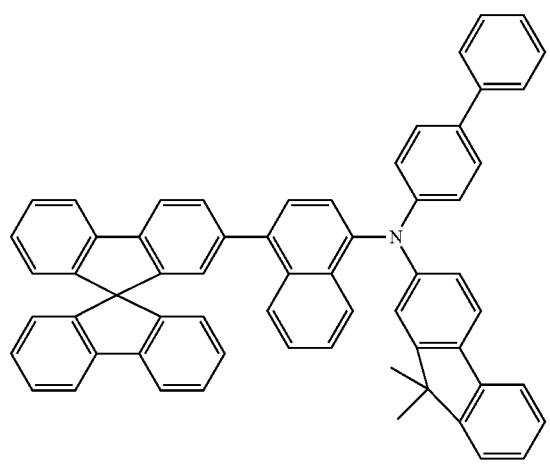 [SMILES: CC1(C)c2ccccc2-c2ccc(N(c3ccc(-c4ccccc4)cc3)c3ccc(-c4ccc5c(c4)C4(c6ccccc6-c6ccccc64)c4ccccc4-5)c4ccccc34)cc21]
(40)
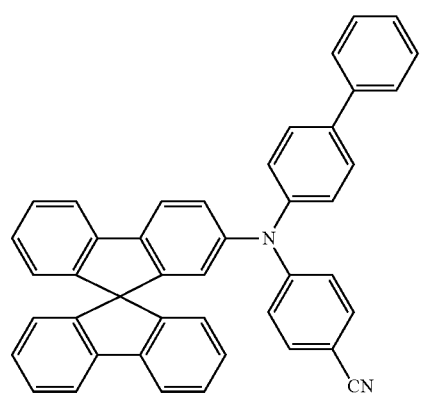 [SMILES: N#Cc1ccc(N(c2ccc(-c3ccccc3)cc2)c2ccc3c(c2)C2(c4ccccc4-c4ccccc42)c2ccccc2-3)cc1]

-continued
(41)
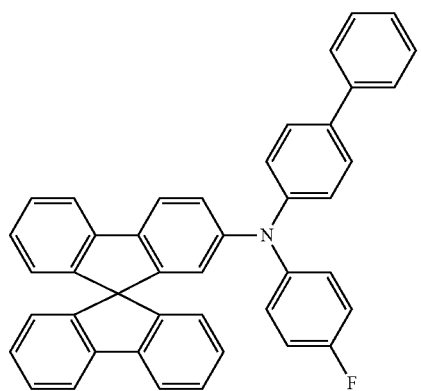 [SMILES: Fc1ccc(N(c2ccc(-c3ccccc3)cc2)c2ccc3c(c2)C2(c4ccccc4-c4ccccc42)c2ccccc2-3)cc1]
(42)
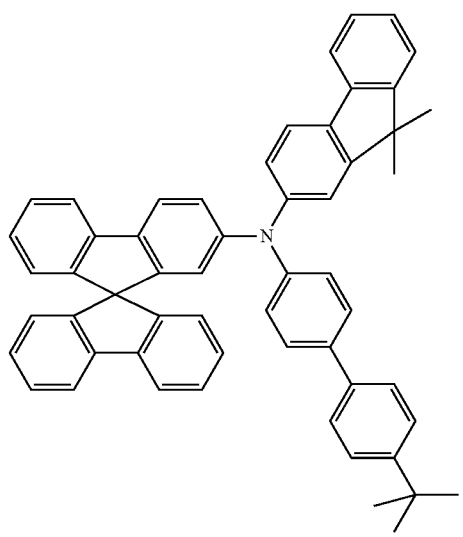 [SMILES: CC(C)(C)c1ccc(-c2ccc(N(c3ccc4c(c3)C(C)(C)c3ccccc3-4)c3ccc4c(c3)C3(c5ccccc5-c5ccccc53)c3ccccc3-4)cc2)cc1]
(43)
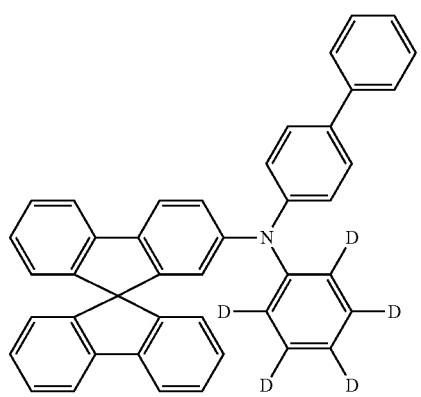 [SMILES: [2H]c1c([2H])c([2H])c(N(c2ccc(-c3ccccc3)cc2)c2ccc3c(c2)C2(c4ccccc4-c4ccccc42)c2ccccc2-3)c([2H])c1[2H]]

-continued
(44)
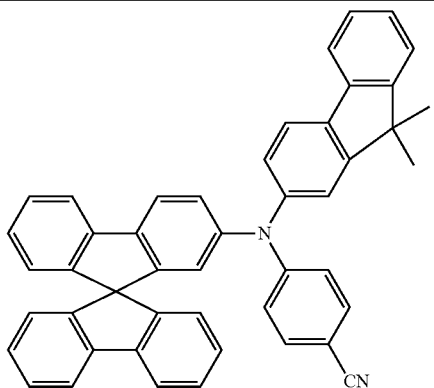
(45)
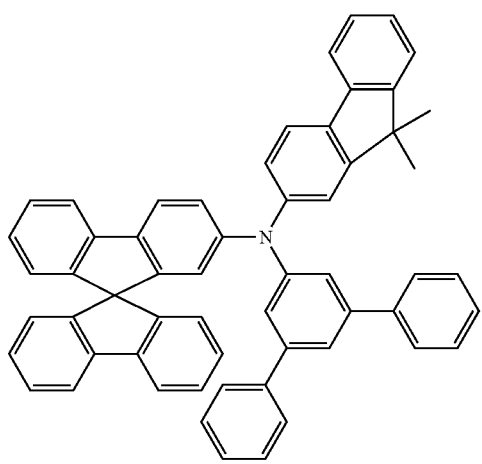
(46)
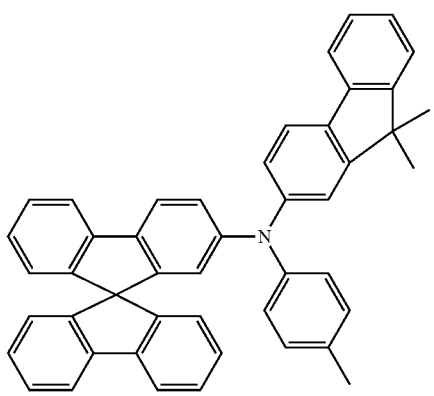 [SMILES: CC1(C)c2ccccc2-c2ccc(N(c3ccc(C#N)cc3)c3ccc4c(c3)C3(c5ccccc5-c5ccccc53)c3ccccc3-4)cc21]
(47)
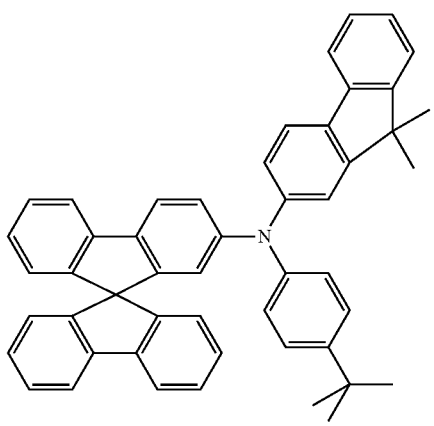 [SMILES: CC(C)(C)c1ccc(N(c2ccc3c(c2)C(C)(C)c2ccccc2-3)c2ccc3c(c2)C2(c4ccccc4-c4ccccc42)c2ccccc2-3)cc1]

-continued
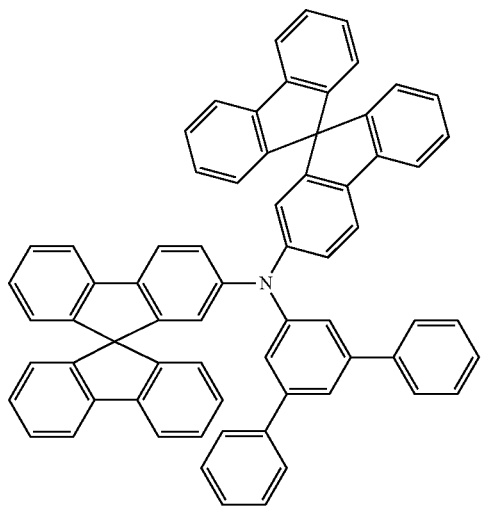 [SMILES: c1ccc(-c2cc(-c3ccccc3)cc(N(c3ccc4c(c3)C3(c5ccccc5-c5ccccc53)c3ccccc3-4)c3ccc4c(c3)C3(c5ccccc5-c5ccccc53)c3ccccc3-4)c2)cc1]
(48)
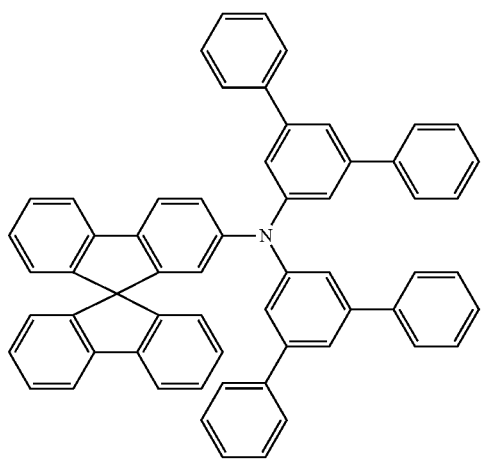 [SMILES: c1ccc(-c2cc(-c3ccccc3)cc(N(c3cc(-c4ccccc4)cc(-c4ccccc4)c3)c3ccc4c(c3)C3(c5ccccc5-c5ccccc53)c3ccccc3-4)c2)cc1]
(49)
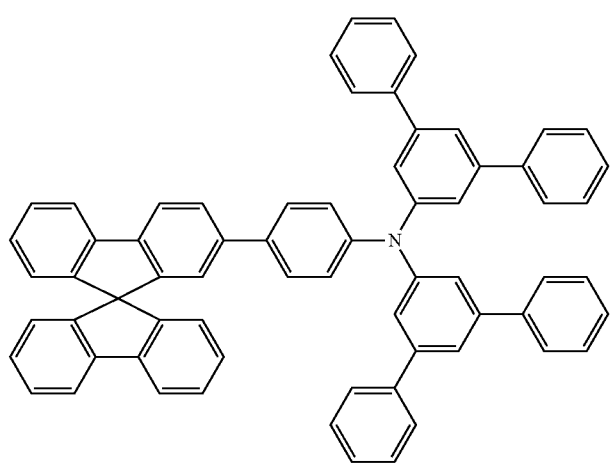 [SMILES: c1ccc(-c2cc(-c3ccccc3)cc(N(c3ccc(-c4ccc5c(c4)C4(c6ccccc6-c6ccccc64)c4ccccc4-5)cc3)c3cc(-c4ccccc4)cc(-c4ccccc4)c3)c2)cc1]
(50)

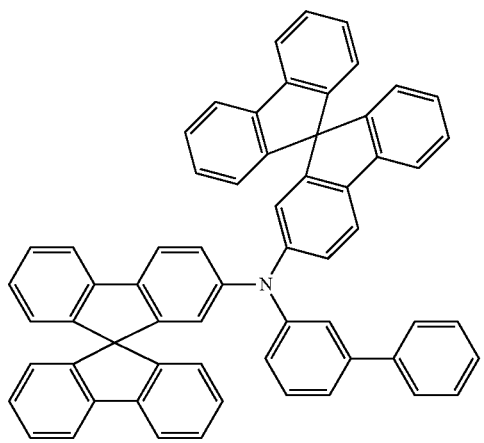 [SMILES: c1ccc(-c2cccc(N(c3ccc4c(c3)C3(c5ccccc5-c5ccccc53)c3ccccc3-4)c3ccc4c(c3)C3(c5ccccc5-c5ccccc53)c3ccccc3-4)c2)cc1]
(51)
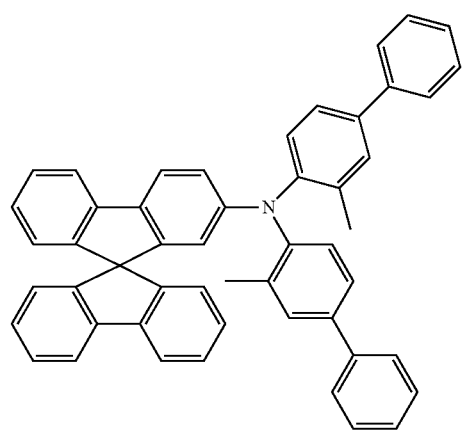 [SMILES: Cc1cc(-c2ccccc2)ccc1N(c1ccc2c(c1)C1(c3ccccc3-c3ccccc31)c1ccccc1-2)c1ccc(-c2ccccc2)cc1C]
(52)
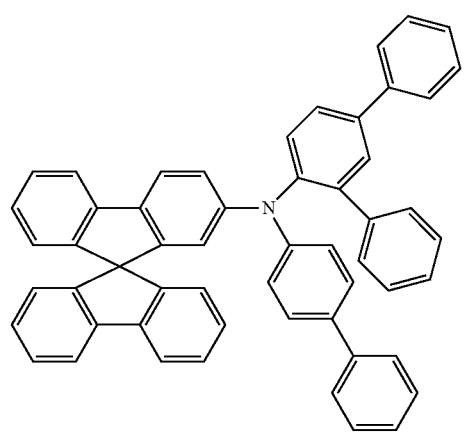 [SMILES: c1ccc(-c2ccc(N(c3ccc4c(c3)C3(c5ccccc5-c5ccccc53)c3ccccc3-4)c3ccc(-c4ccccc4)cc3-c3ccccc3)cc2)cc1]
(53)

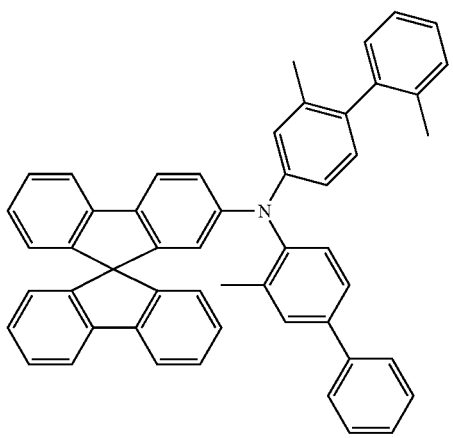 [SMILES: Cc1ccccc1-c1ccc(N(c2ccc3c(c2)C2(c4ccccc4-c4ccccc42)c2ccccc2-3)c2ccc(-c3ccccc3)cc2C)cc1C]
(54)
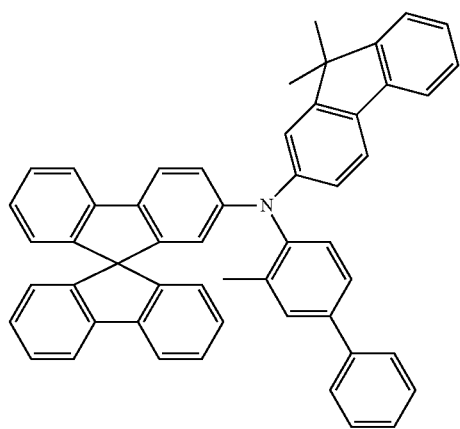 [SMILES: Cc1cc(-c2ccccc2)ccc1N(c1ccc2c(c1)C(C)(C)c1ccccc1-2)c1ccc2c(c1)C1(c3ccccc3-c3ccccc31)c1ccccc1-2]
(55)
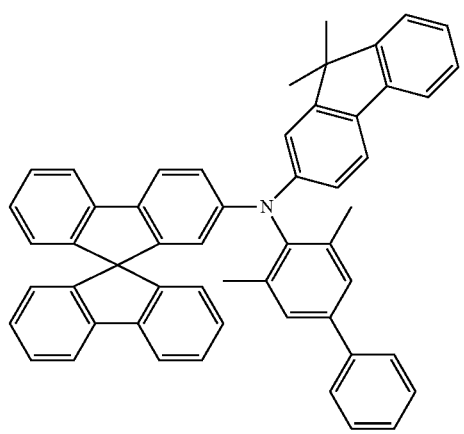 [SMILES: Cc1cc(-c2ccccc2)cc(C)c1N(c1ccc2c(c1)C(C)(C)c1ccccc1-2)c1ccc2c(c1)C1(c3ccccc3-c3ccccc31)c1ccccc1-2]
(56)

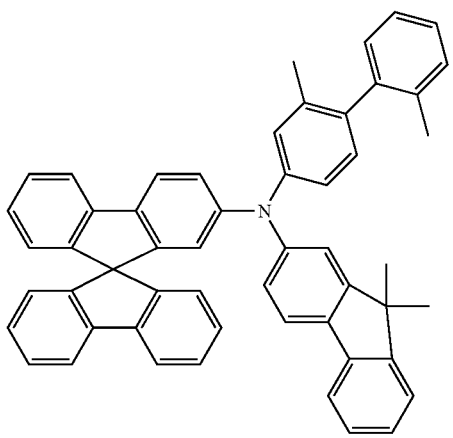 [SMILES: Cc1ccccc1-c1ccc(N(c2ccc3c(c2)C(C)(C)c2ccccc2-3)c2ccc3c(c2)C2(c4ccccc4-c4ccccc42)c2ccccc2-3)cc1C]
(57)
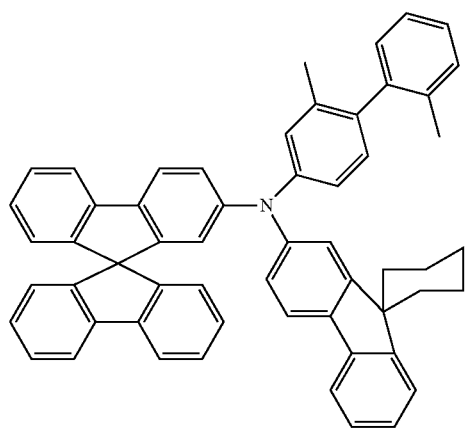 [SMILES: Cc1ccccc1-c1ccc(N(c2ccc3c(c2)C2(CCCCC2)c2ccccc2-3)c2ccc3c(c2)C2(c4ccccc4-c4ccccc42)c2ccccc2-3)cc1C]
(58)
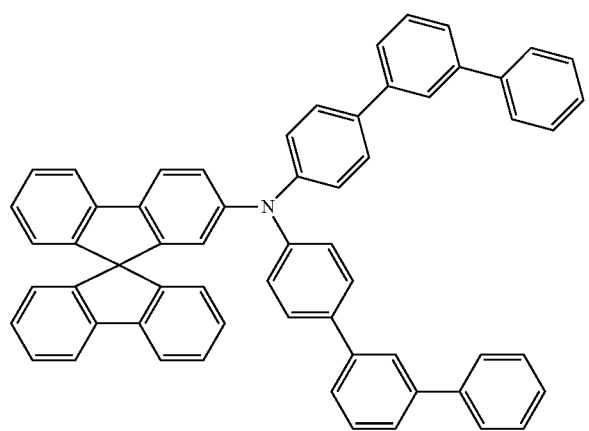 [SMILES: c1ccc(-c2cccc(-c3ccc(N(c4ccc(-c5cccc(-c6ccccc6)c5)cc4)c4ccc5c(c4)C4(c6ccccc6-c6ccccc64)c4ccccc4-5)cc3)c2)cc1]
(59)

-continued
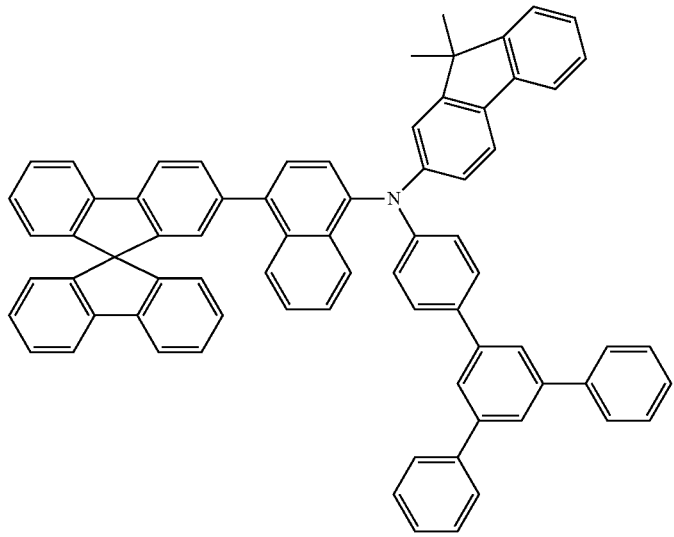 [SMILES: CC1(C)c2ccccc2-c2ccc(N(c3ccc(-c4cc(-c5ccccc5)cc(-c5ccccc5)c4)cc3)c3ccc(-c4ccc5c(c4)C4(c6ccccc6-c6ccccc64)c4ccccc4-5)c4ccccc34)cc21]
(60)
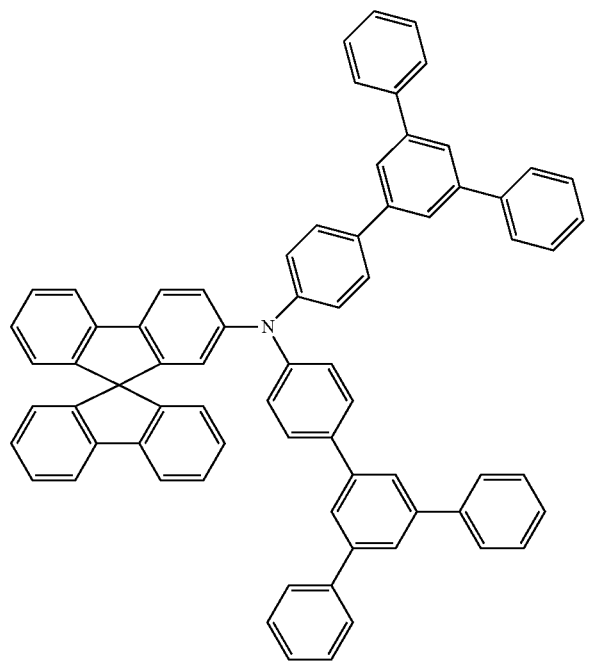 [SMILES: c1ccc(-c2cc(-c3ccccc3)cc(-c3ccc(N(c4ccc(-c5cc(-c6ccccc6)cc(-c6ccccc6)c5)cc4)c4ccc5c(c4)C4(c6ccccc6-c6ccccc64)c4ccccc4-5)cc3)c2)cc1]
(61)
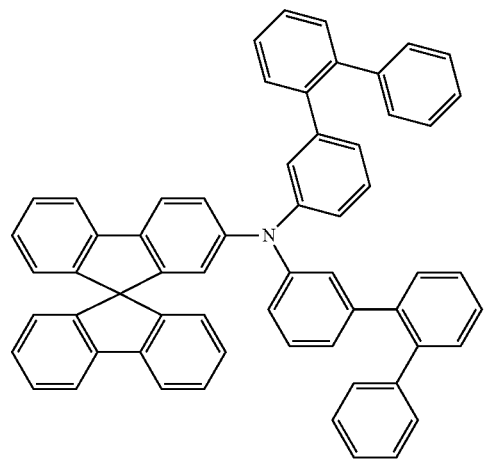 [SMILES: c1ccc(-c2ccccc2-c2cccc(N(c3cccc(-c4ccccc4-c4ccccc4)c3)c3ccc4c(c3)C3(c5ccccc5-c5ccccc53)c3ccccc3-4)c2)cc1]
(62)

-continued
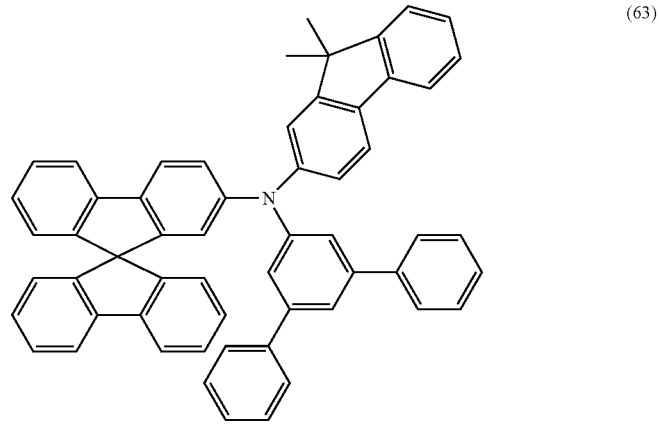
(63)
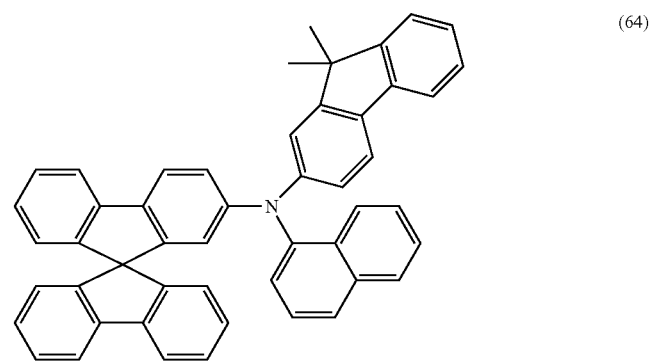
(64)
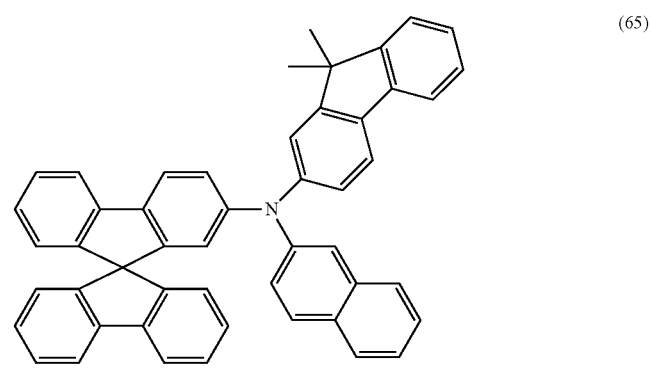
(65)
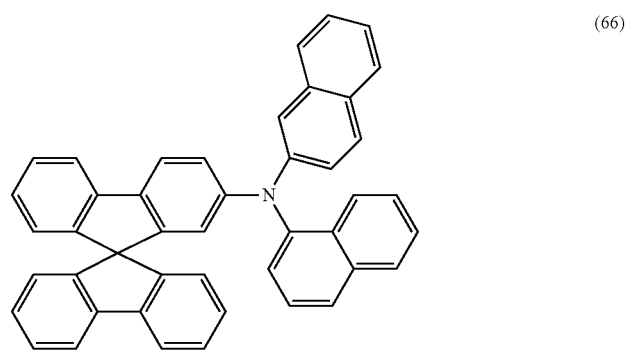
(66)

-continued
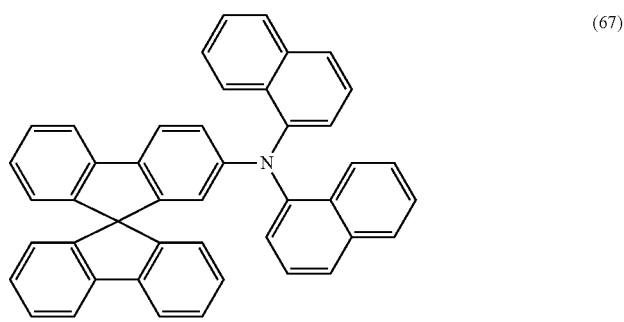
(67)
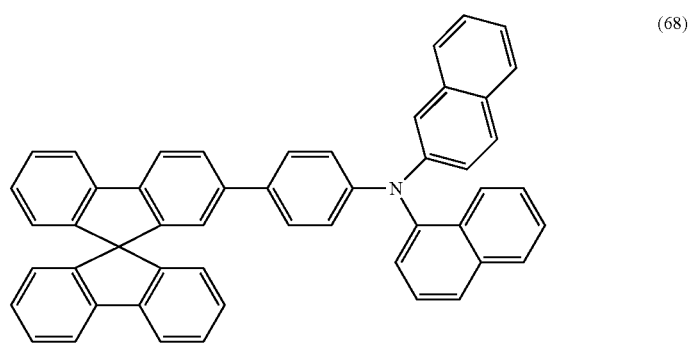
(68)
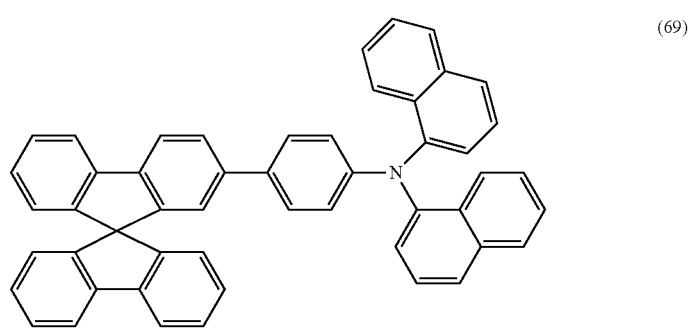
(69)
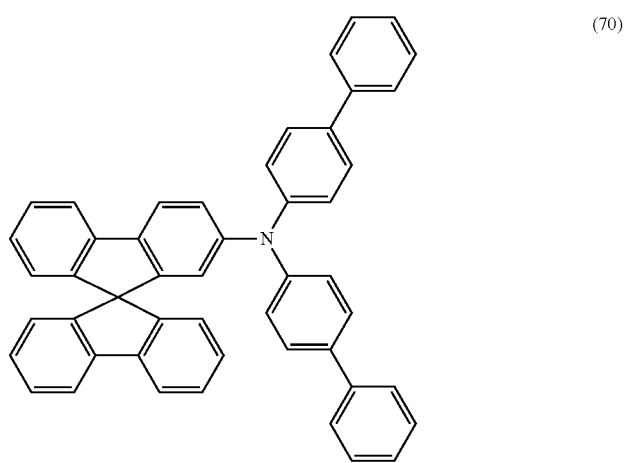
(70)

-continued
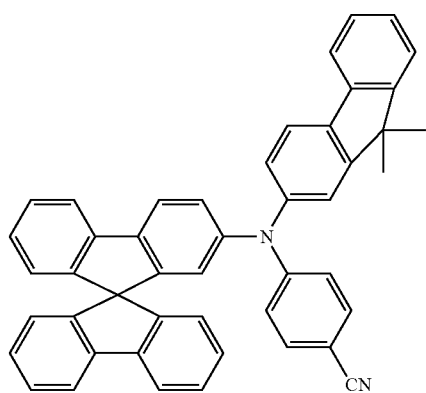 [SMILES: CC1(C)c2ccccc2-c2ccc(N(c3ccc(C#N)cc3)c3ccc4c(c3)C3(c5ccccc5-c5ccccc53)c3ccccc3-4)cc21]
(71)
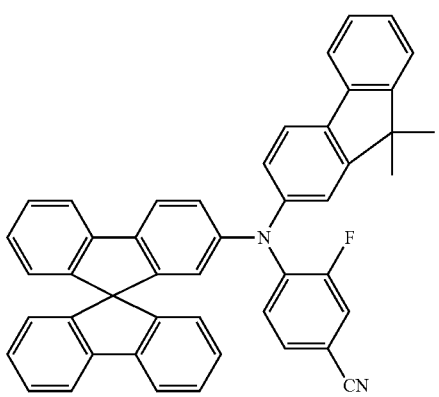 [SMILES: CC1(C)c2ccccc2-c2ccc(N(c3ccc4c(c3)C3(c5ccccc5-c5ccccc53)c3ccccc3-4)c3ccc(C#N)cc3F)cc21]
(72)
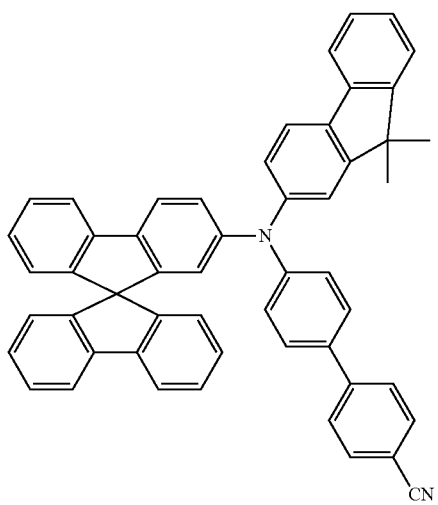 [SMILES: CC1(C)c2ccccc2-c2ccc(N(c3ccc(-c4ccc(C#N)cc4)cc3)c3ccc4c(c3)C3(c5ccccc5-c5ccccc53)c3ccccc3-4)cc21]
(73)

(74)
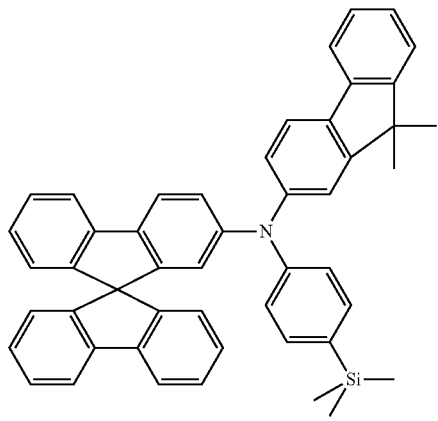 [SMILES: CC1(C)c2ccccc2-c2ccc(N(c3ccc([Si](C)(C)C)cc3)c3ccc4c(c3)C3(c5ccccc5-c5ccccc53)c3ccccc3-4)cc21]
(75)
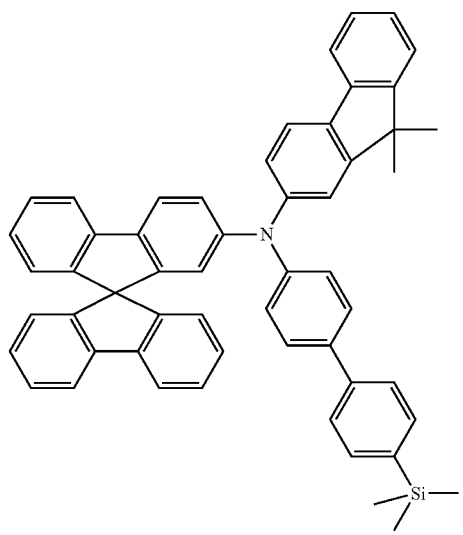 [SMILES: CC1(C)c2ccccc2-c2ccc(N(c3ccc(-c4ccc([Si](C)(C)C)cc4)cc3)c3ccc4c(c3)C3(c5ccccc5-c5ccccc53)c3ccccc3-4)cc21]
(76)
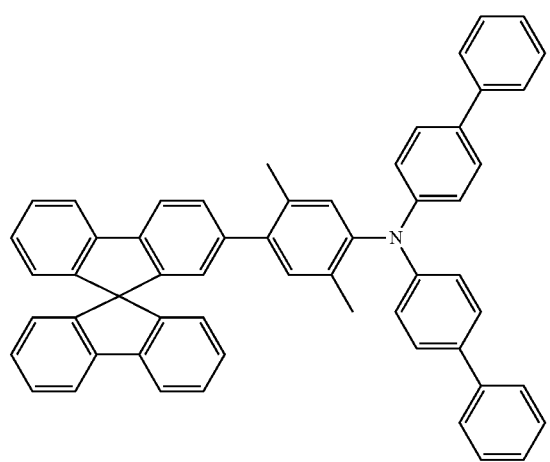 [SMILES: Cc1cc(N(c2ccc(-c3ccccc3)cc2)c2ccc(-c3ccccc3)cc2)c(C)cc1-c1ccc2c(c1)C1(c3ccccc3-c3ccccc31)c1ccccc1-2]

-continued
(77)
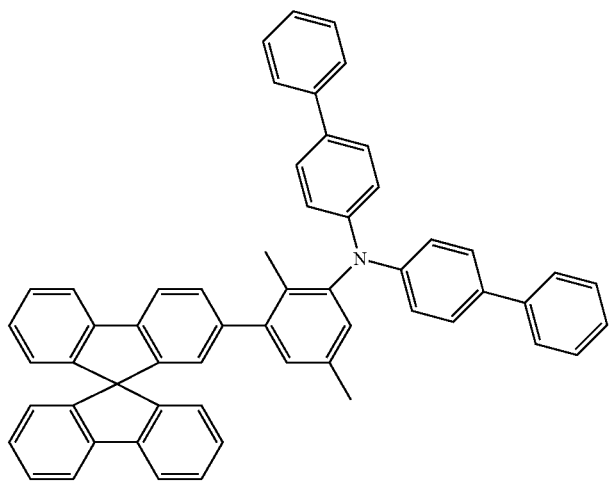 [SMILES: Cc1cc(-c2ccc3c(c2)C2(c4ccccc4-c4ccccc42)c2ccccc2-3)c(C)c(N(c2ccc(-c3ccccc3)cc2)c2ccc(-c3ccccc3)cc2)c1]
(78)
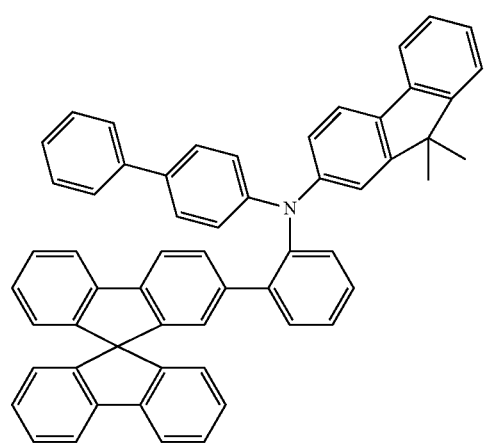 [SMILES: CC1(C)c2ccccc2-c2ccc(N(c3ccc(-c4ccccc4)cc3)c3ccccc3-c3ccc4c(c3)C3(c5ccccc5-c5ccccc53)c3ccccc3-4)cc21]
(79)
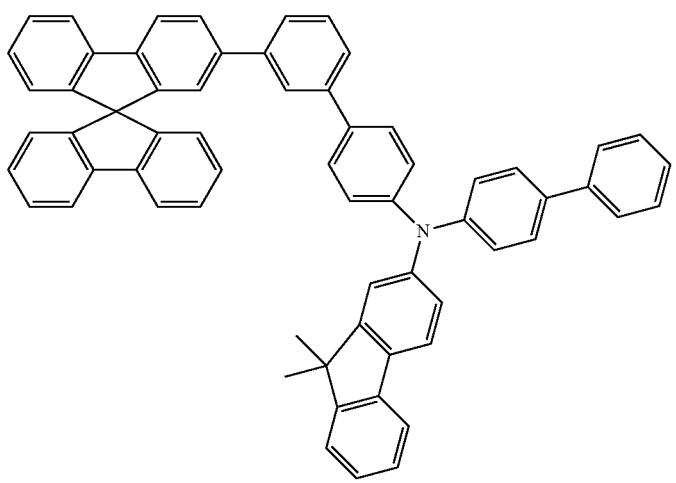 [SMILES: CC1(C)c2ccccc2-c2ccc(N(c3ccc(-c4ccccc4)cc3)c3ccc(-c4cccc(-c5ccc6c(c5)C5(c7ccccc7-c7ccccc75)c5ccccc5-6)c4)cc3)cc21]

-continued
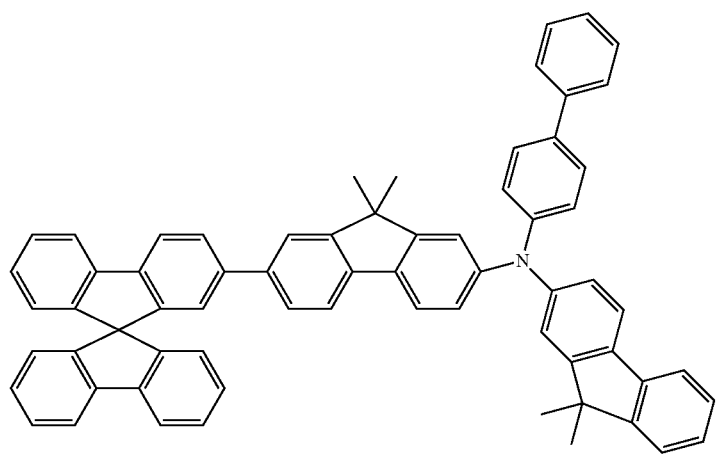 [SMILES: CC1(C)c2ccccc2-c2ccc(N(c3ccc(-c4ccccc4)cc3)c3ccc4c(c3)C(C)(C)c3cc(-c5ccc6c(c5)C5(c7ccccc7-c7ccccc75)c5ccccc5-6)ccc3-4)cc21]
(80)
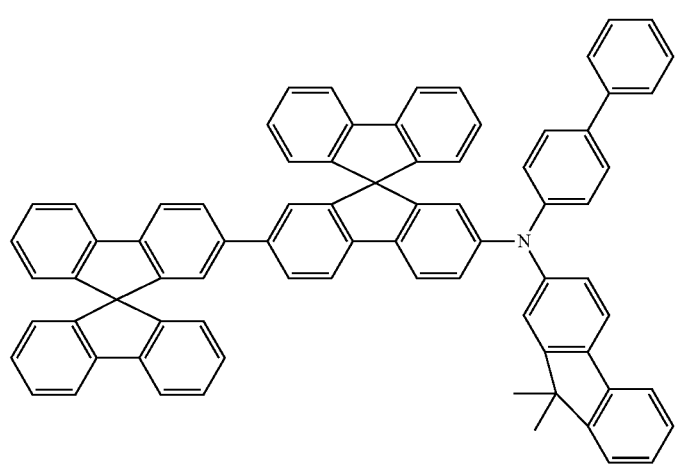 [SMILES: CC1(C)c2ccccc2-c2ccc(N(c3ccc(-c4ccccc4)cc3)c3ccc4c(c3)C3(c5ccccc5-c5ccccc53)c3cc(-c5ccc6c(c5)C5(c7ccccc7-c7ccccc75)c5ccccc5-6)ccc3-4)cc21]
(81)
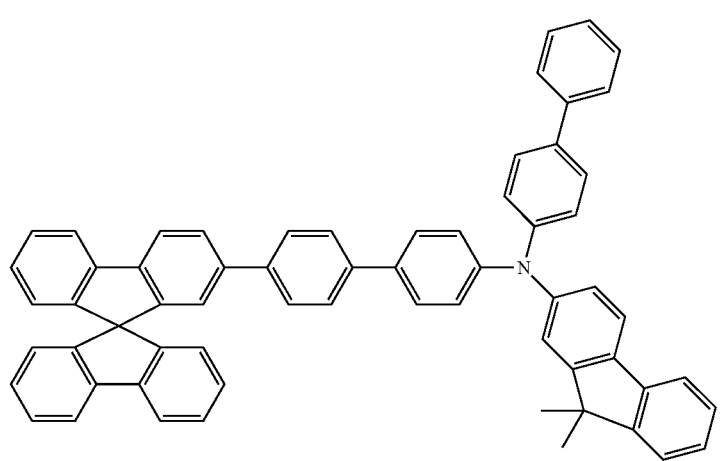 [SMILES: CC1(C)c2ccccc2-c2ccc(N(c3ccc(-c4ccccc4)cc3)c3ccc(-c4ccc(-c5ccc6c(c5)C5(c7ccccc7-c7ccccc75)c5ccccc5-6)cc4)cc3)cc21]
(82)

-continued
(83)
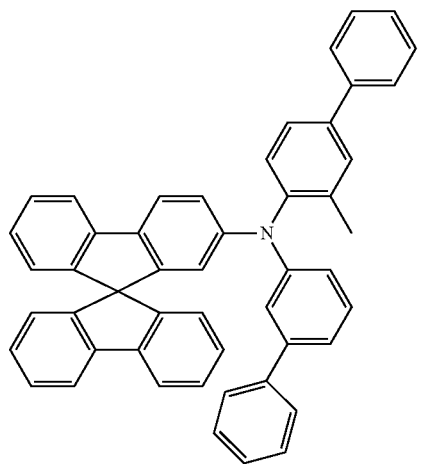 [SMILES: Cc1cc(-c2ccccc2)ccc1N(c1cccc(-c2ccccc2)c1)c1ccc2c(c1)C1(c3ccccc3-c3ccccc31)c1ccccc1-2]
(84)
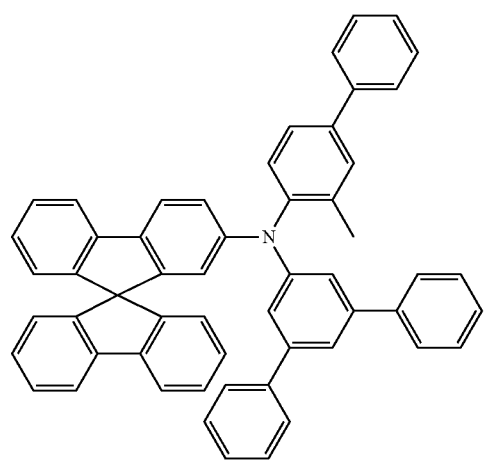 [SMILES: Cc1cc(-c2ccccc2)ccc1N(c1cc(-c2ccccc2)cc(-c2ccccc2)c1)c1ccc2c(c1)C1(c3ccccc3-c3ccccc31)c1ccccc1-2]
(85)
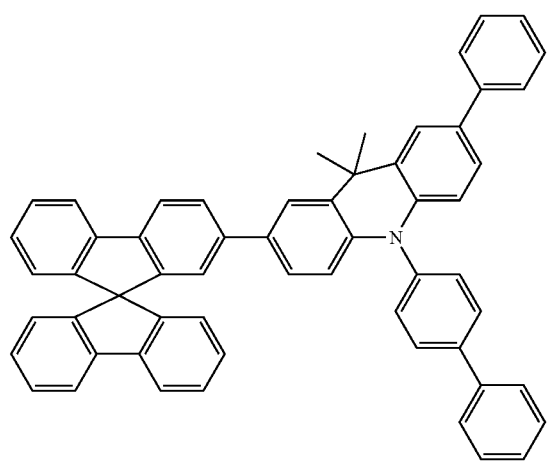 [SMILES: CC1(C)c2cc(-c3ccccc3)ccc2N(c2ccc(-c3ccccc3)cc2)c2ccc(-c3ccc4c(c3)C3(c5ccccc5-c5ccccc53)c3ccccc3-4)cc21]

-continued
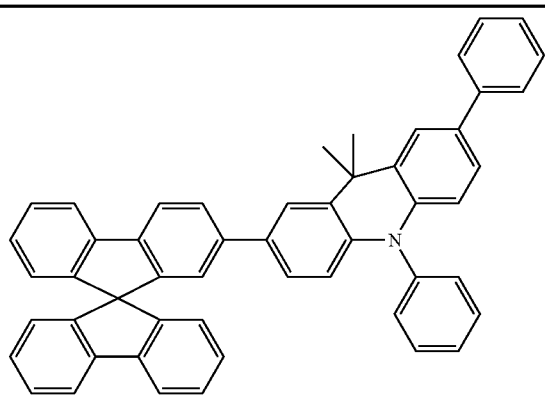
(86)
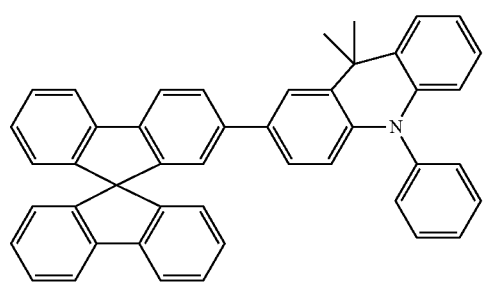 [SMILES: CC1(C)c2ccccc2N(c2ccccc2)c2ccc(-c3ccc4c(c3)C3(c5ccccc5-c5ccccc53)c3ccccc3-4)cc21]
(87)
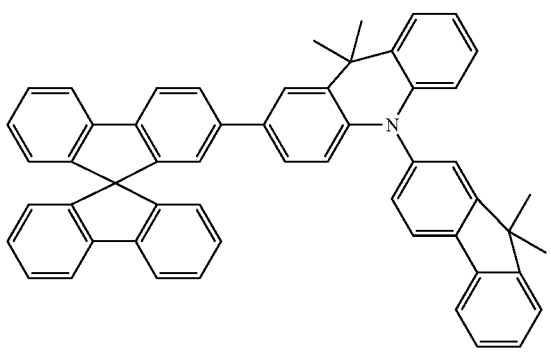 [SMILES: CC1(C)c2ccccc2-c2ccc(N3c4ccccc4C(C)(C)c4cc(-c5ccc6c(c5)C5(c7ccccc7-c7ccccc75)c5ccccc5-6)ccc43)cc21]
(88)
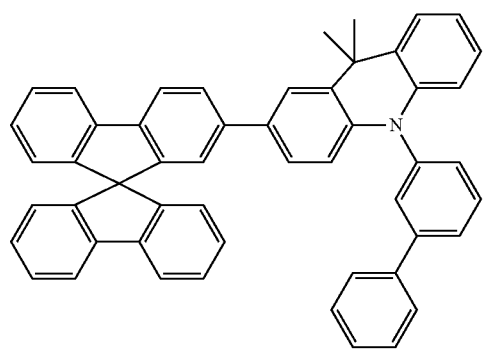 [SMILES: CC1(C)c2ccccc2N(c2cccc(-c3ccccc3)c2)c2ccc(-c3ccc4c(c3)C3(c5ccccc5-c5ccccc53)c3ccccc3-4)cc21]
(89)
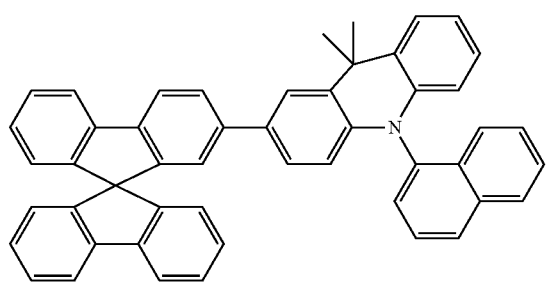 [SMILES: CC1(C)c2ccccc2N(c2cccc3ccccc23)c2ccc(-c3ccc4c(c3)C3(c5ccccc5-c5ccccc53)c3ccccc3-4)cc21]
(90)

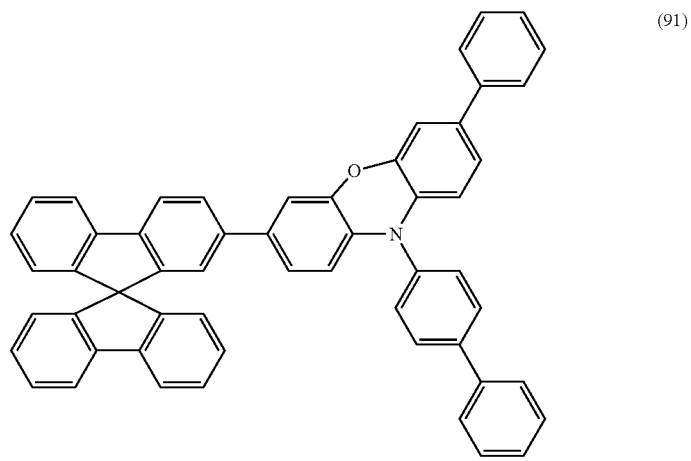
(91)
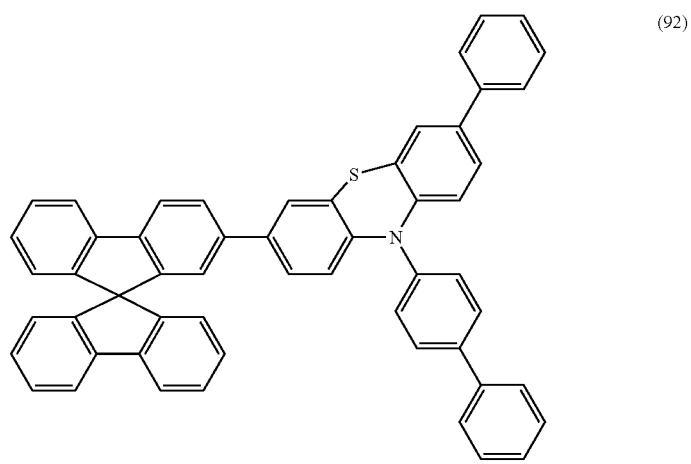
(92)
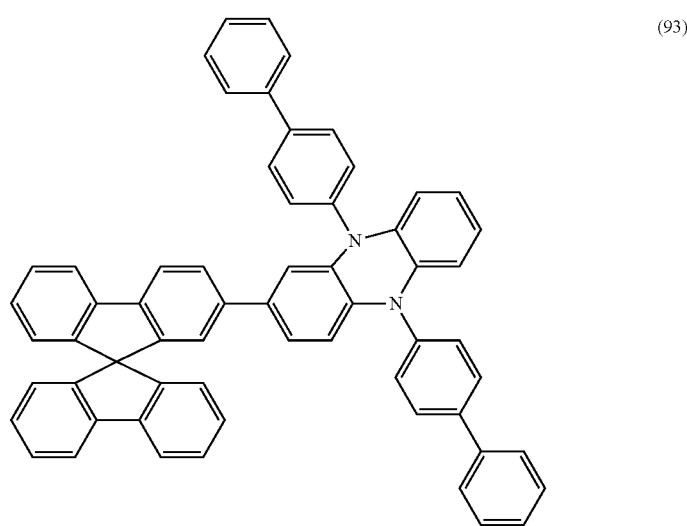
(93)

-continued
(94)
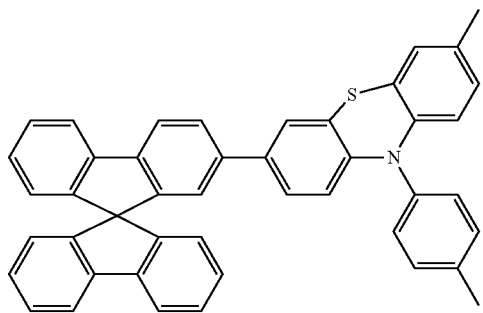 [SMILES: Cc1ccc(N2c3ccc(C)cc3Sc3cc(-c4ccc5c(c4)C4(c6ccccc6-c6ccccc64)c4ccccc4-5)ccc32)cc1]
(95)
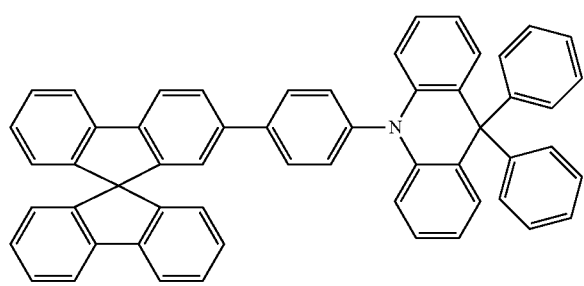 [SMILES: c1ccc(C2(c3ccccc3)c3ccccc3N(c3ccc(-c4ccc5c(c4)C4(c6ccccc6-c6ccccc64)c4ccccc4-5)cc3)c3ccccc32)cc1]
(96)
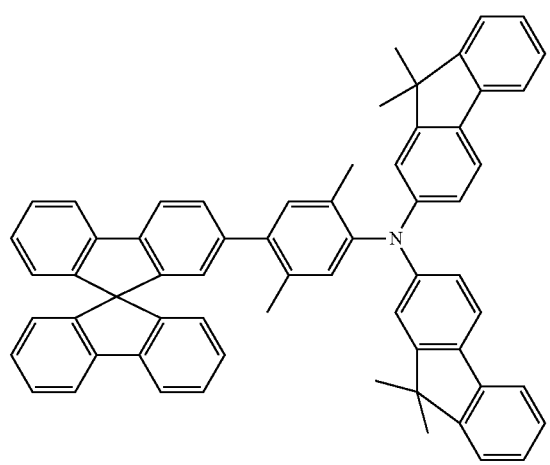 [SMILES: Cc1cc(N(c2ccc3c(c2)C(C)(C)c2ccccc2-3)c2ccc3c(c2)C(C)(C)c2ccccc2-3)c(C)cc1-c1ccc2c(c1)C1(c3ccccc3-c3ccccc31)c1ccccc1-2]
(97)
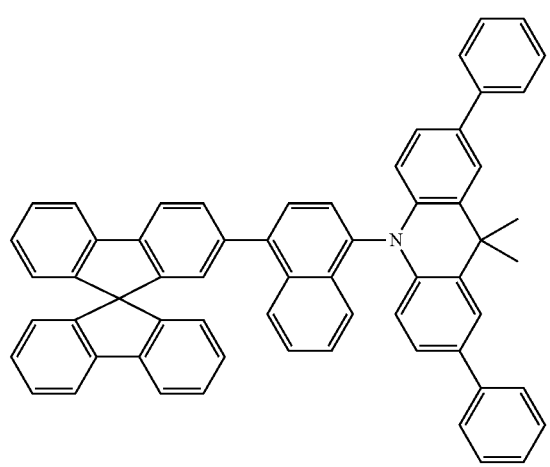 [SMILES: CC1(C)c2cc(-c3ccccc3)ccc2N(c2ccc(-c3ccc4c(c3)C3(c5ccccc5-c5ccccc53)c3ccccc3-4)c3ccccc23)c2ccc(-c3ccccc3)cc21]

-continued
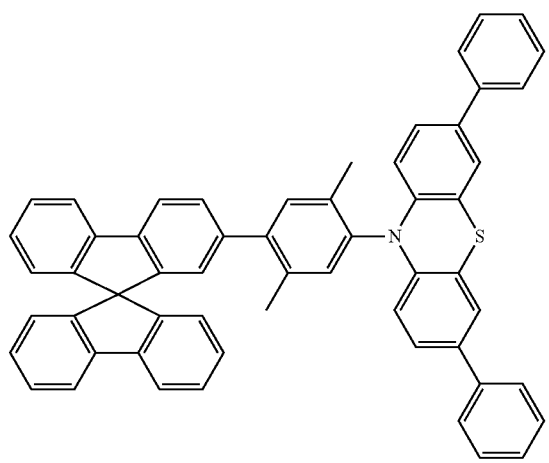 [SMILES: Cc1cc(N2c3ccc(-c4ccccc4)cc3Sc3cc(-c4ccccc4)ccc32)c(C)cc1-c1ccc2c(c1)C1(c3ccccc3-c3ccccc31)c1ccccc1-2]
(98)
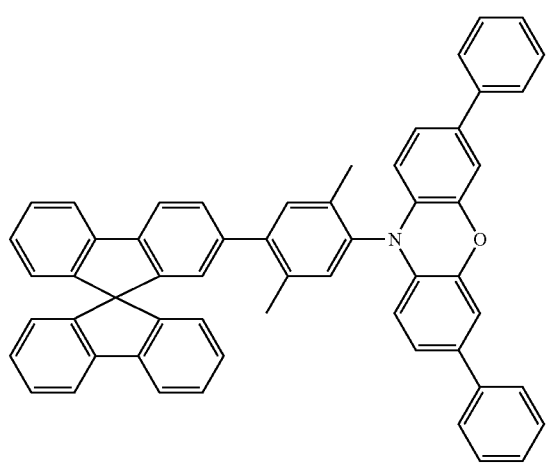
(99)
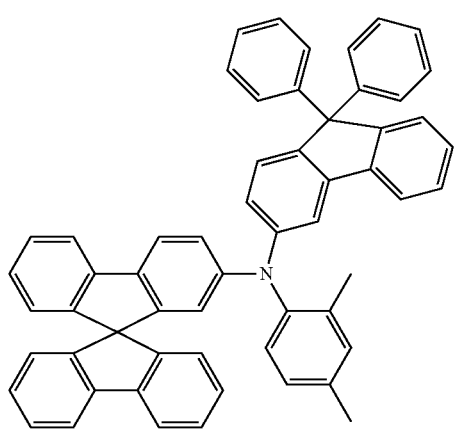 [SMILES: Cc1ccc(N(c2ccc3c(c2)-c2ccccc2C3(c2ccccc2)c2ccccc2)c2ccc3c(c2)C2(c4ccccc4-c4ccccc42)c2ccccc2-3)c(C)c1]
(100)

-continued
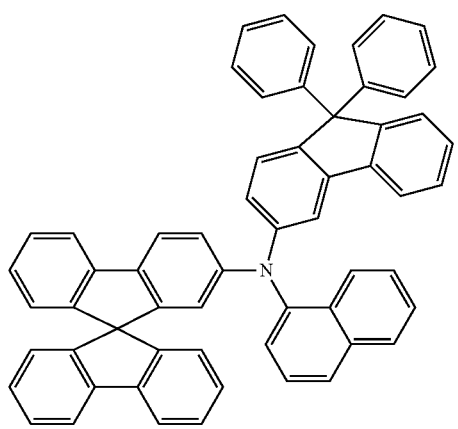 [SMILES: c1ccc(C2(c3ccccc3)c3ccccc3-c3cc(N(c4ccc5c(c4)C4(c6ccccc6-c6ccccc64)c4ccccc4-5)c4cccc5ccccc45)ccc32)cc1]
(101)
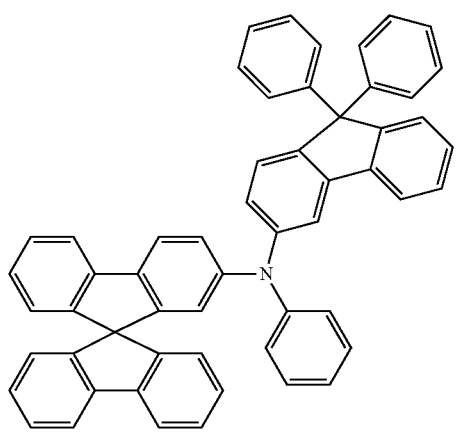 [SMILES: c1ccc(N(c2ccc3c(c2)-c2ccccc2C3(c2ccccc2)c2ccccc2)c2ccc3c(c2)C2(c4ccccc4-c4ccccc42)c2ccccc2-3)cc1]
(102)
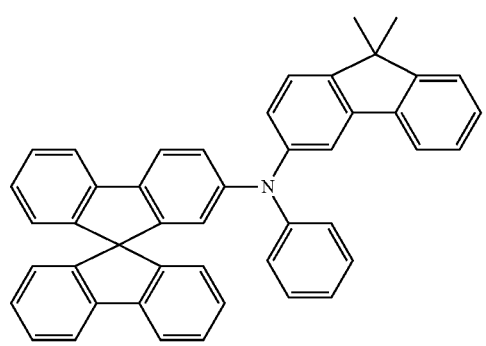 [SMILES: CC1(C)c2ccccc2-c2cc(N(c3ccccc3)c3ccc4c(c3)C3(c5ccccc5-c5ccccc53)c3ccccc3-4)ccc21]
(103)
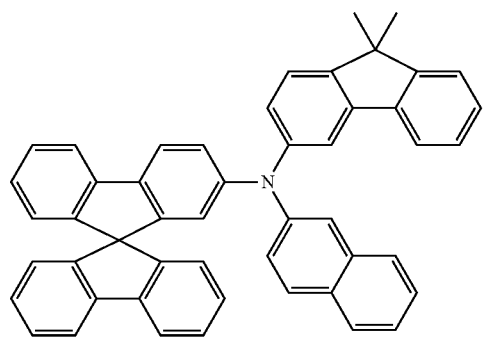 [SMILES: CC1(C)c2ccccc2-c2cc(N(c3ccc4c(c3)C3(c5ccccc5-c5ccccc53)c3ccccc3-4)c3ccc4ccccc4c3)ccc21]
(104)

-continued
(105)
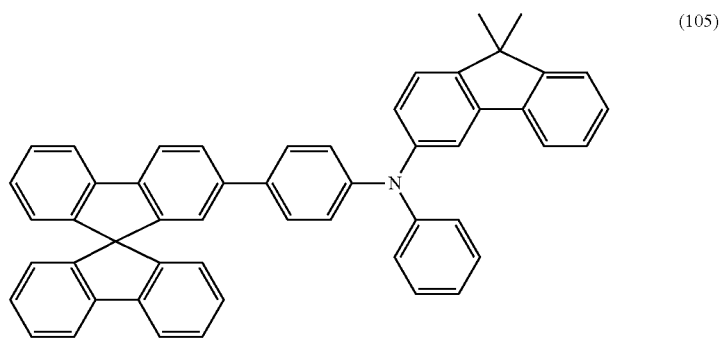
(106)
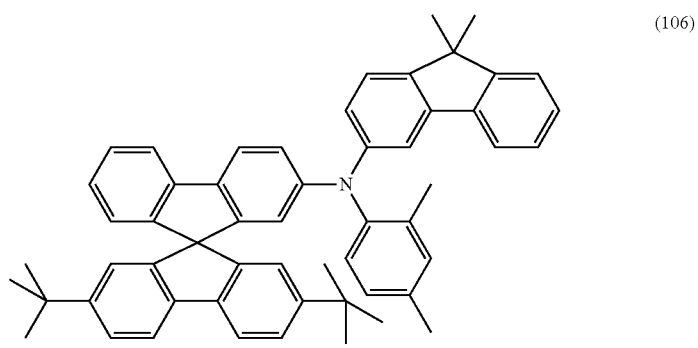
(107)
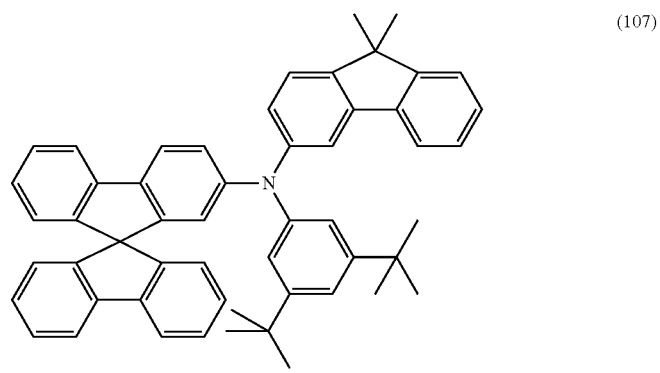
(108)
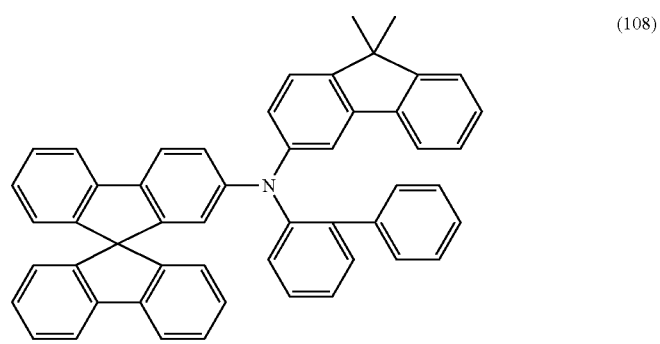

-continued
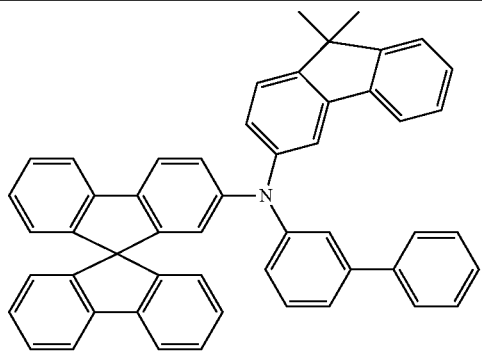
(109)
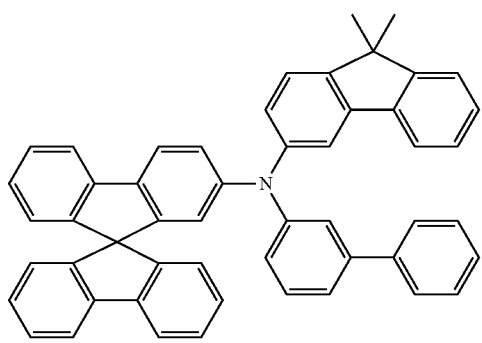 [SMILES: CC1(C)c2ccccc2-c2cc(N(c3cccc(-c4ccccc4)c3)c3ccc4c(c3)C3(c5ccccc5-c5ccccc53)c3ccccc3-4)ccc21]
(110)
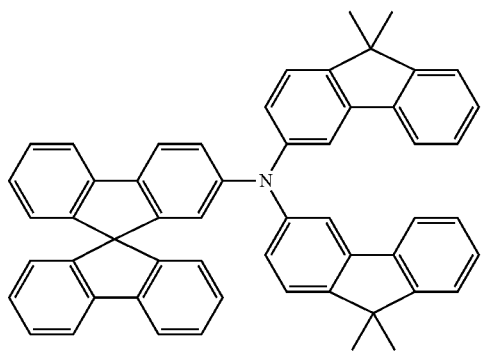 [SMILES: CC1(C)c2ccccc2-c2cc(N(c3ccc4c(c3)-c3ccccc3C4(C)C)c3ccc4c(c3)C3(c5ccccc5-c5ccccc53)c3ccccc3-4)ccc21]
(111)
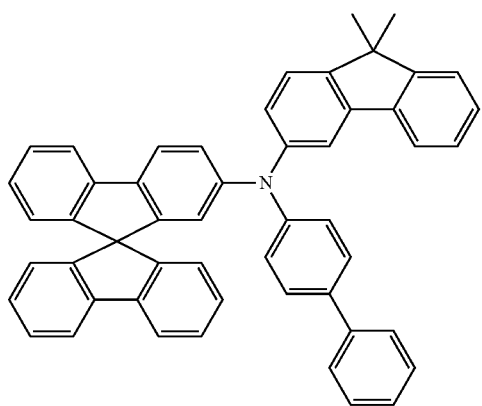 [SMILES: CC1(C)c2ccccc2-c2cc(N(c3ccc(-c4ccccc4)cc3)c3ccc4c(c3)C3(c5ccccc5-c5ccccc53)c3ccccc3-4)ccc21]
(112)

-continued
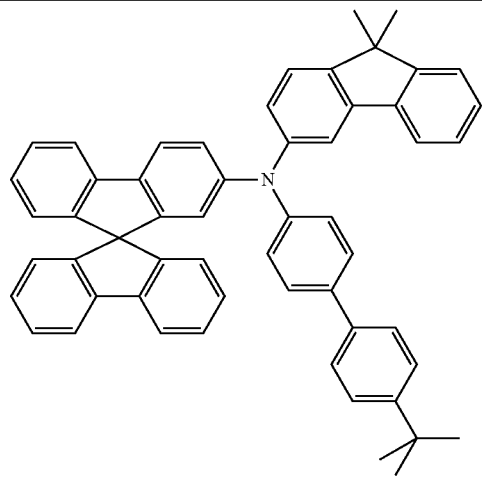
(113)
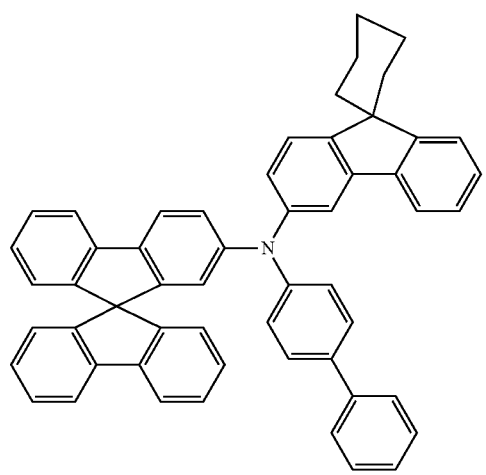 [SMILES: c1ccc(-c2ccc(N(c3ccc4c(c3)-c3ccccc3C43CCCCC3)c3ccc4c(c3)C3(c5ccccc5-c5ccccc53)c3ccccc3-4)cc2)cc1]
(114)
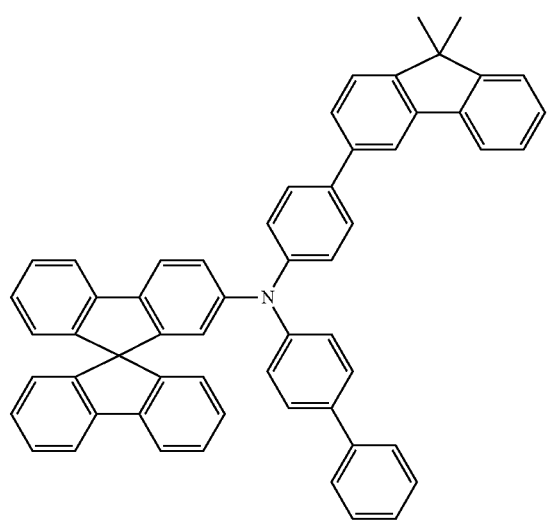 [SMILES: CC1(C)c2ccccc2-c2cc(-c3ccc(N(c4ccc(-c5ccccc5)cc4)c4ccc5c(c4)C4(c6ccccc6-c6ccccc64)c4ccccc4-5)cc3)ccc21]
(115)

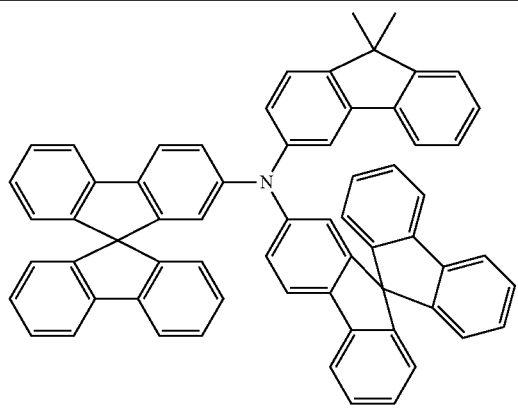
(116)
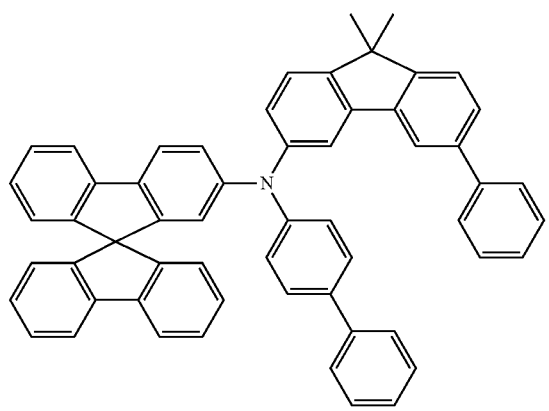 [SMILES: CC1(C)c2ccc(-c3ccccc3)cc2-c2cc(N(c3ccc(-c4ccccc4)cc3)c3ccc4c(c3)C3(c5ccccc5-c5ccccc53)c3ccccc3-4)ccc21]
(117)
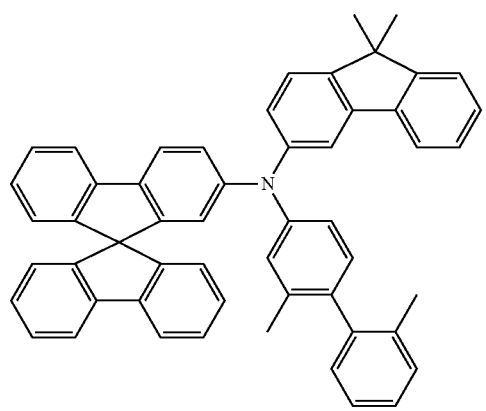 [SMILES: Cc1ccccc1-c1ccc(N(c2ccc3c(c2)-c2ccccc2C3(C)C)c2ccc3c(c2)C2(c4ccccc4-c4ccccc42)c2ccccc2-3)cc1C]
(118)
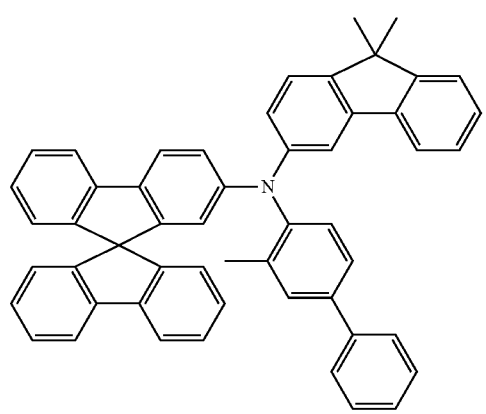
(119)

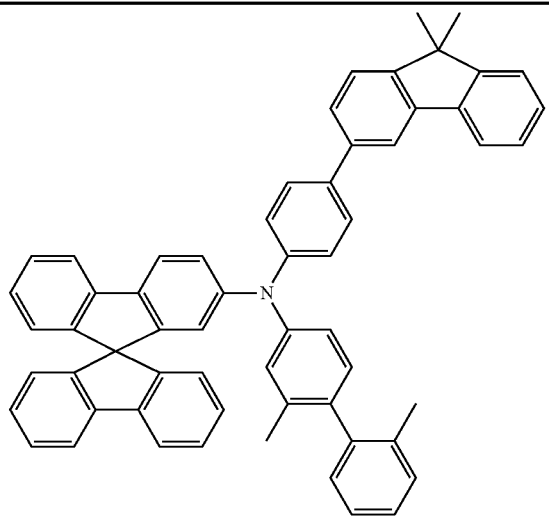
(120)
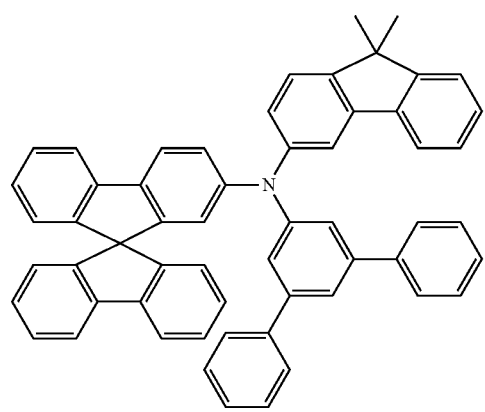 [SMILES: CC1(C)c2ccccc2-c2cc(N(c3cc(-c4ccccc4)cc(-c4ccccc4)c3)c3ccc4c(c3)C3(c5ccccc5-c5ccccc53)c3ccccc3-4)ccc21]
(121)
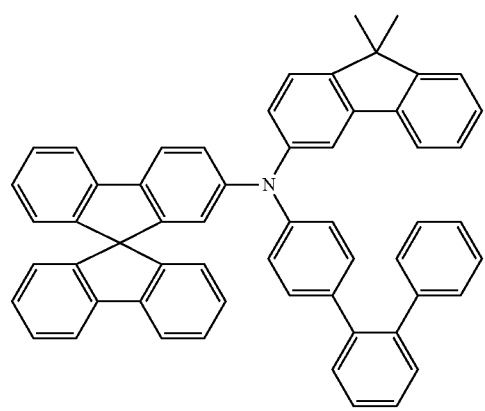 [SMILES: CC1(C)c2ccccc2-c2cc(N(c3ccc(-c4ccccc4-c4ccccc4)cc3)c3ccc4c(c3)C3(c5ccccc5-c5ccccc53)c3ccccc3-4)ccc21]
(122)
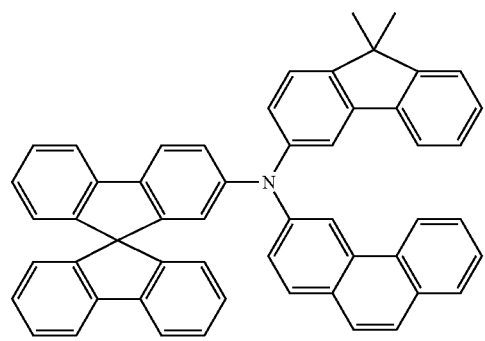 [SMILES: CC1(C)c2ccccc2-c2cc(N(c3ccc4c(c3)C3(c5ccccc5-c5ccccc53)c3ccccc3-4)c3ccc4ccc5ccccc5c4c3)ccc21]
(123)

(124)
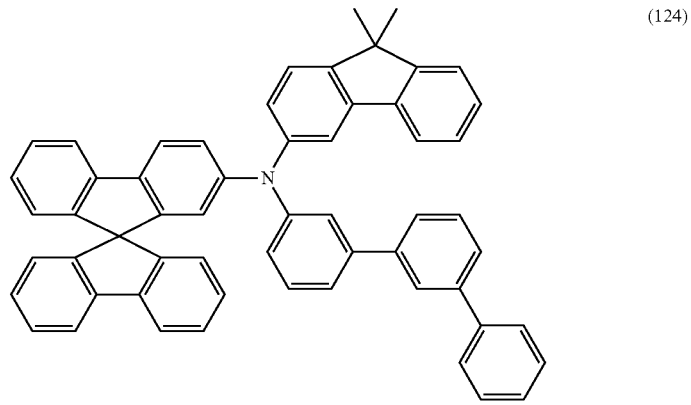
(125)
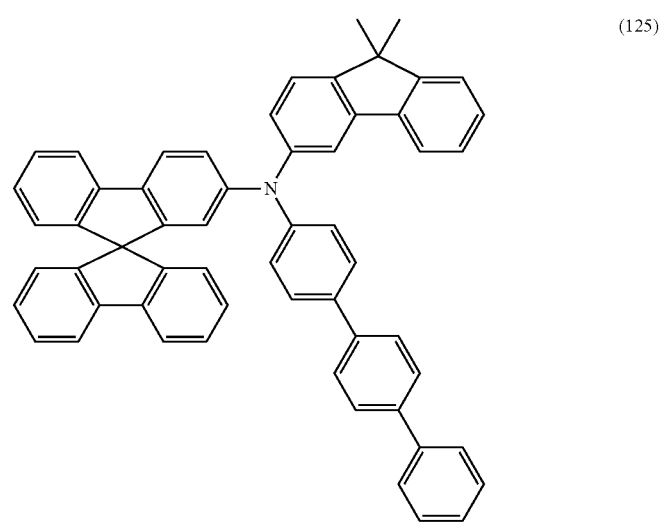
(126)
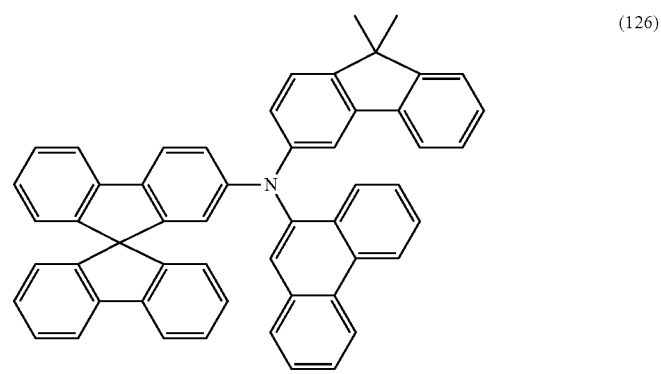

-continued
(127)
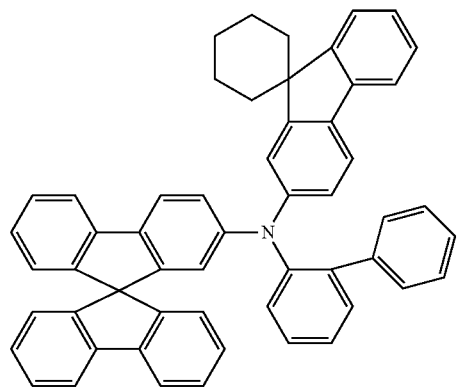 [SMILES: c1ccc(-c2ccccc2N(c2ccc3c(c2)C2(CCCCC2)c2ccccc2-3)c2ccc3c(c2)C2(c4ccccc4-c4ccccc42)c2ccccc2-3)cc1]
(128)
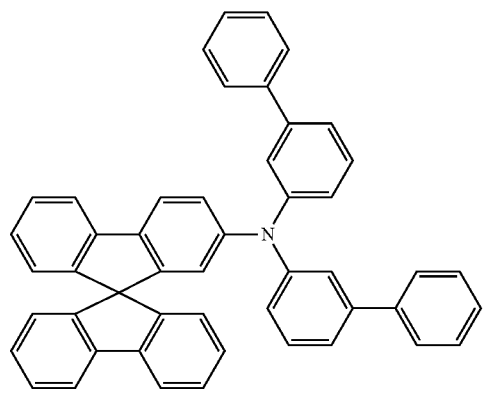 [SMILES: c1ccc(-c2cccc(N(c3cccc(-c4ccccc4)c3)c3ccc4c(c3)C3(c5ccccc5-c5ccccc53)c3ccccc3-4)c2)cc1]
(129)
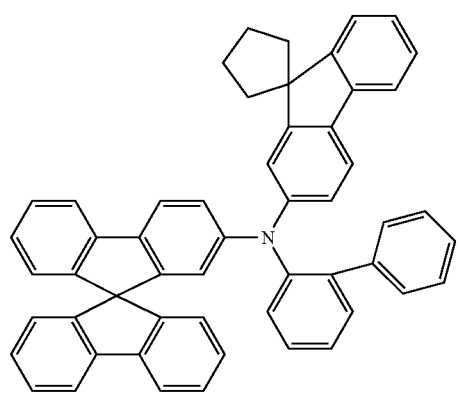 [SMILES: c1ccc(-c2ccccc2N(c2ccc3c(c2)C2(CCCC2)c2ccccc2-3)c2ccc3c(c2)C2(c4ccccc4-c4ccccc42)c2ccccc2-3)cc1]
(130)
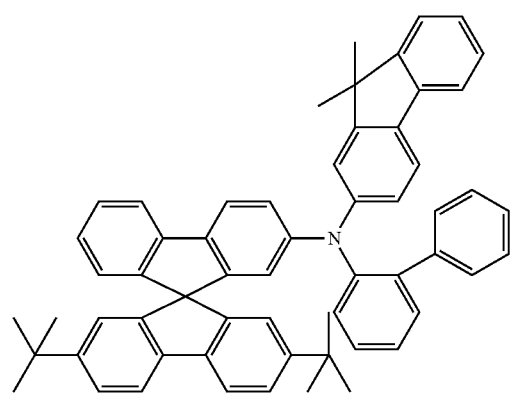 [SMILES: CC(C)(C)c1ccc2c(c1)C1(c3ccccc3-c3ccc(N(c4ccc5c(c4)C(C)(C)c4ccccc4-5)c4ccccc4-c4ccccc4)cc31)c1cc(C(C)(C)C)ccc1-2]

-continued
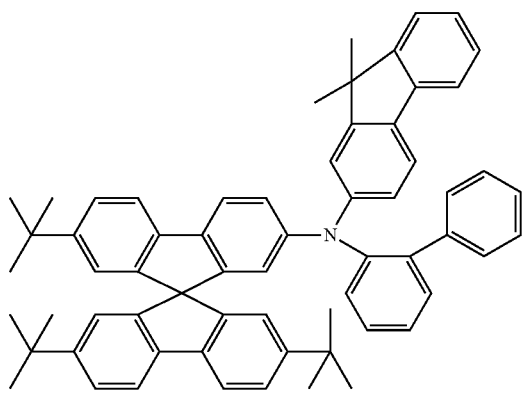 [SMILES: CC(C)(C)c1ccc2c(c1)C1(c3cc(N(c4ccc5c(c4)C(C)(C)c4ccccc4-5)c4ccccc4-c4ccccc4)ccc3-2)c2cc(C(C)(C)C)ccc2-c2ccc(C(C)(C)C)cc21]
(131)
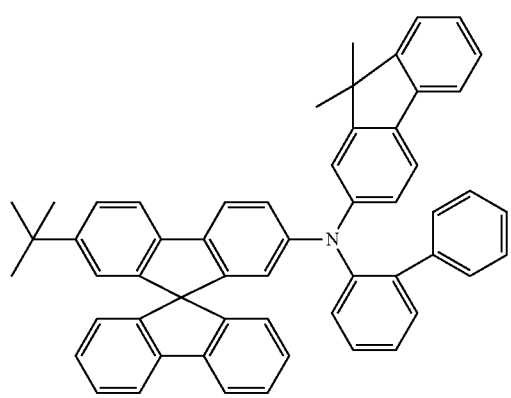 [SMILES: CC(C)(C)c1ccc2c(c1)C1(c3ccccc3-c3ccccc31)c1cc(N(c3ccc4c(c3)C(C)(C)c3ccccc3-4)c3ccccc3-c3ccccc3)ccc1-2]
(132)
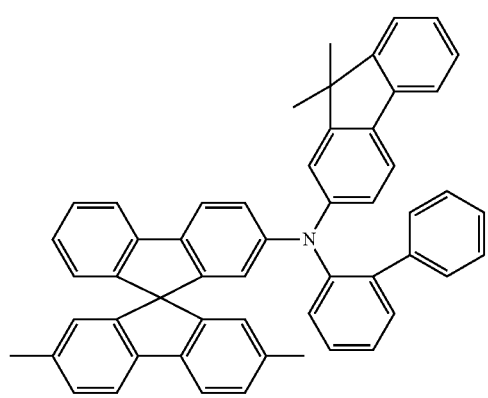 [SMILES: Cc1ccc2c(c1)C1(c3ccccc3-c3ccc(N(c4ccc5c(c4)C(C)(C)c4ccccc4-5)c4ccccc4-c4ccccc4)cc31)c1cc(C)ccc1-2]
(133)
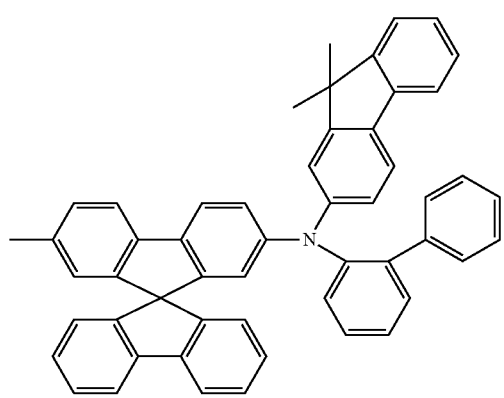 [SMILES: Cc1ccc2c(c1)C1(c3ccccc3-c3ccccc31)c1cc(N(c3ccc4c(c3)C(C)(C)c3ccccc3-4)c3ccccc3-c3ccccc3)ccc1-2]
(134)

(135)
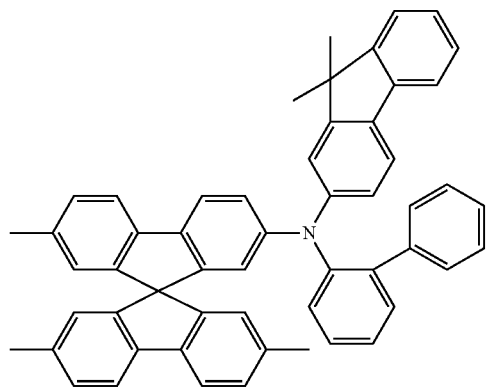 [SMILES: Cc1ccc2c(c1)C1(c3cc(C)ccc3-2)c2cc(C)ccc2-c2ccc(N(c3ccc4c(c3)C(C)(C)c3ccccc3-4)c3ccccc3-c3ccccc3)cc21]
(136)
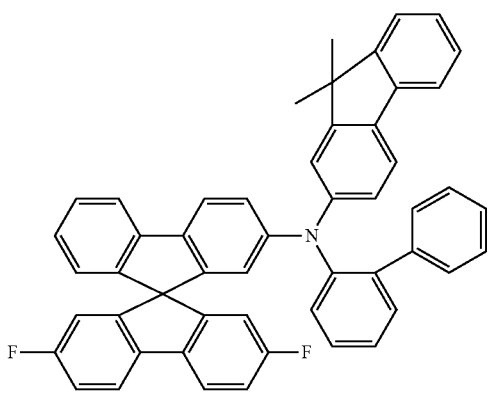 [SMILES: CC1(C)c2ccccc2-c2ccc(N(c3ccc4c(c3)C3(c5ccccc5-4)c4cc(F)ccc4-c4ccc(F)cc43)c3ccccc3-c3ccccc3)cc21]
(137)
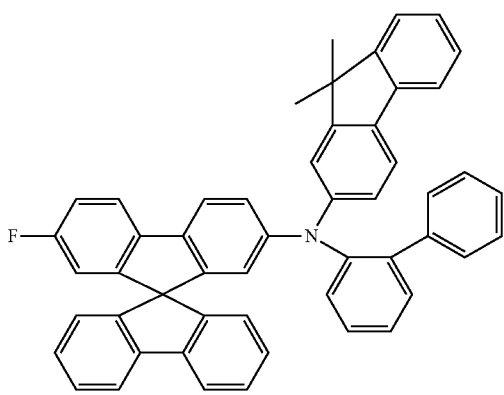 [SMILES: CC1(C)c2ccccc2-c2ccc(N(c3ccc4c(c3)C3(c5ccccc5-c5ccccc53)c3cc(F)ccc3-4)c3ccccc3-c3ccccc3)cc21]
(138)
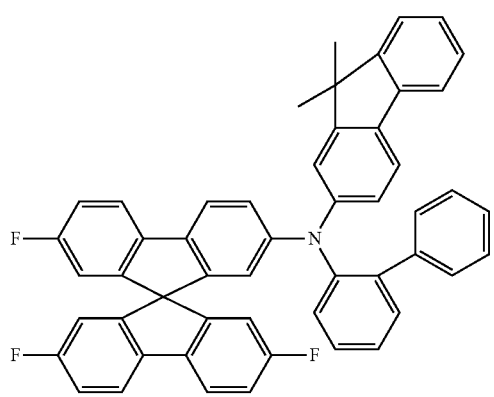 [SMILES: CC1(C)c2ccccc2-c2ccc(N(c3ccc4c(c3)C3(c5cc(F)ccc5-c5ccc(F)cc53)c3cc(F)ccc3-4)c3ccccc3-c3ccccc3)cc21]

-continued
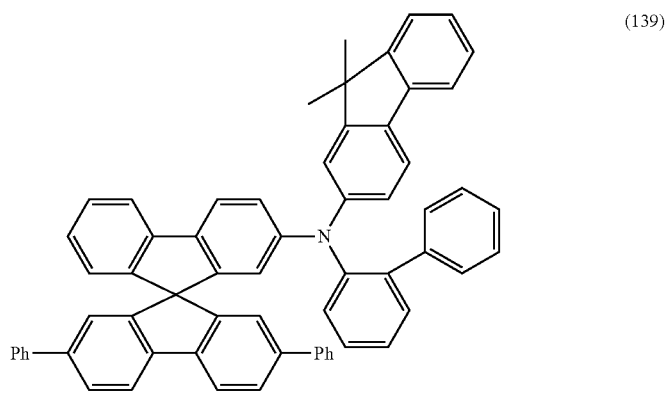
(139)
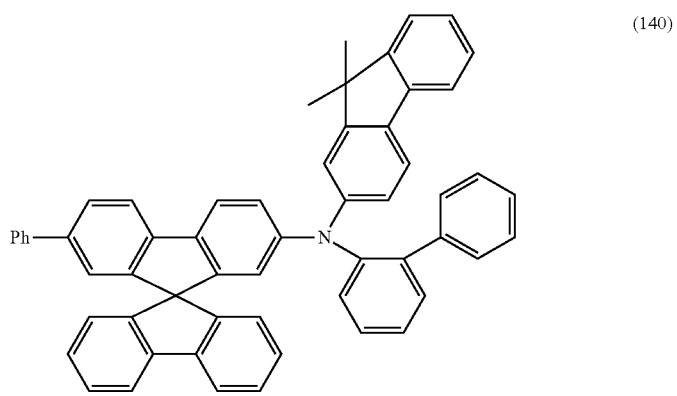
(140)
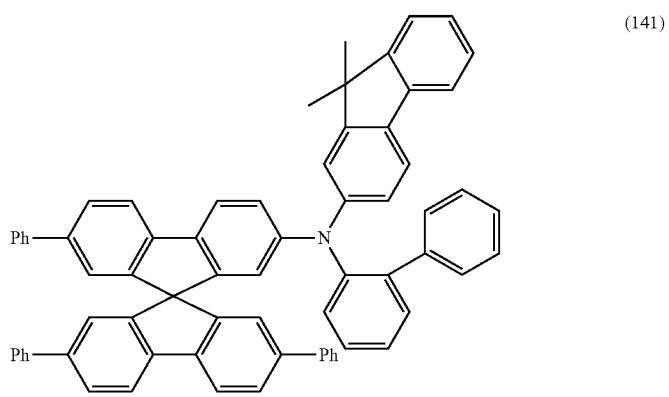
(141)
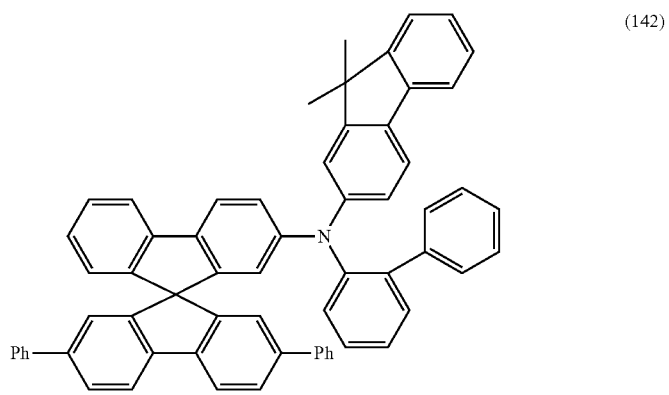
(142)

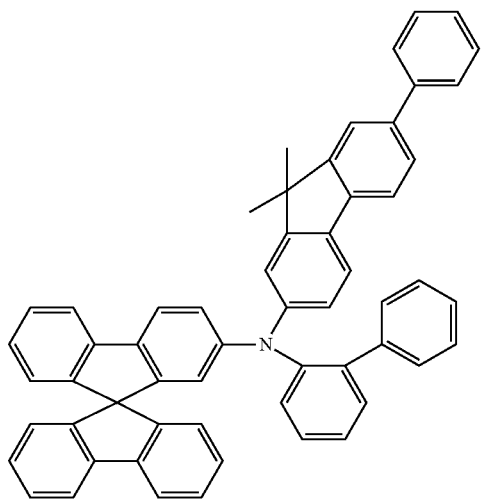 [SMILES: CC1(C)c2cc(-c3ccccc3)ccc2-c2ccc(N(c3ccc4c(c3)C3(c5ccccc5-c5ccccc53)c3ccccc3-4)c3ccccc3-c3ccccc3)cc21]
(143)
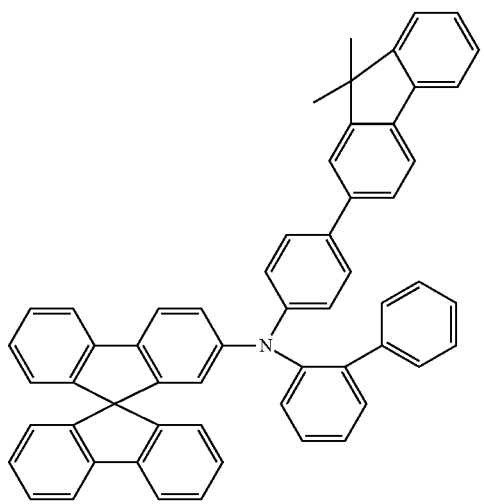 [SMILES: CC1(C)c2ccccc2-c2ccc(-c3ccc(N(c4ccc5c(c4)C4(c6ccccc6-c6ccccc64)c4ccccc4-5)c4ccccc4-c4ccccc4)cc3)cc21]
(144)
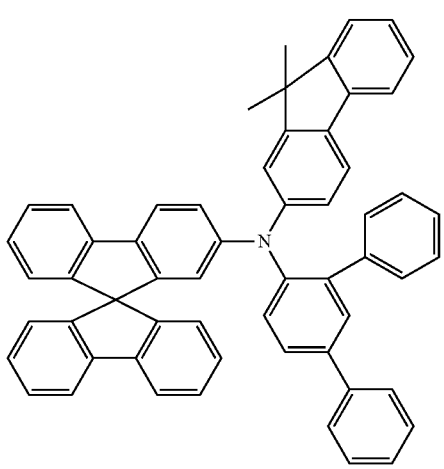 [SMILES: CC1(C)c2ccccc2-c2ccc(N(c3ccc4c(c3)C3(c5ccccc5-c5ccccc53)c3ccccc3-4)c3ccc(-c4ccccc4)cc3-c3ccccc3)cc21]
(145)

(146)
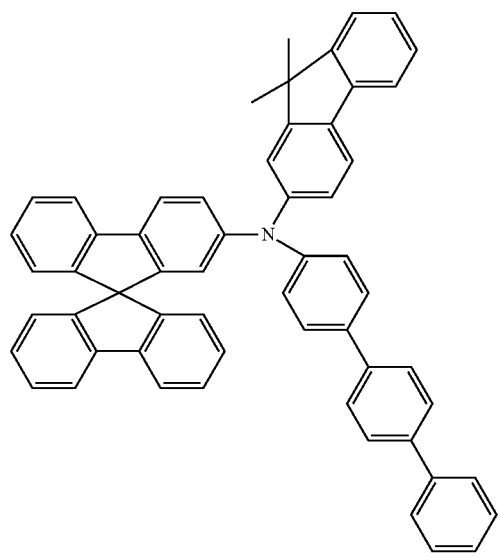 [SMILES: CC1(C)c2ccccc2-c2ccc(N(c3ccc(-c4ccc(-c5ccccc5)cc4)cc3)c3ccc4c(c3)C3(c5ccccc5-c5ccccc53)c3ccccc3-4)cc21]
(147)
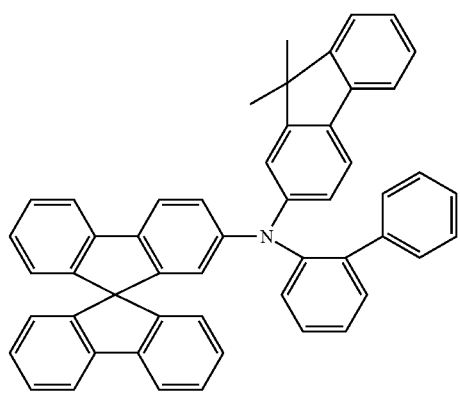 [SMILES: CC1(C)c2ccccc2-c2ccc(N(c3ccc4c(c3)C3(c5ccccc5-c5ccccc53)c3ccccc3-4)c3ccccc3-c3ccccc3)cc21]
(148)
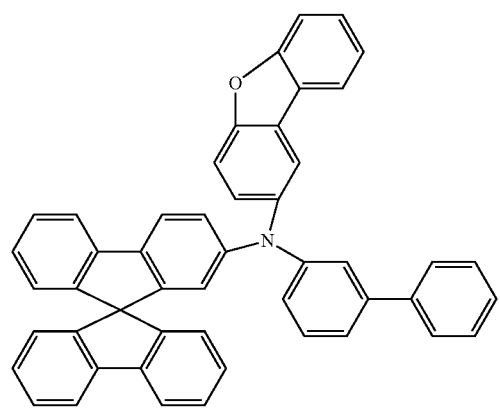 [SMILES: c1ccc(-c2cccc(N(c3ccc4c(c3)C3(c5ccccc5-c5ccccc53)c3ccccc3-4)c3ccc4oc5ccccc5c4c3)c2)cc1]

-continued
(149)
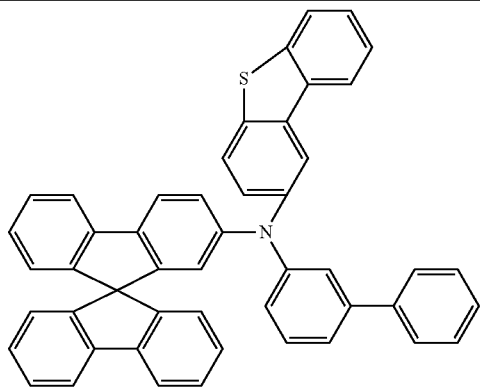
(150)
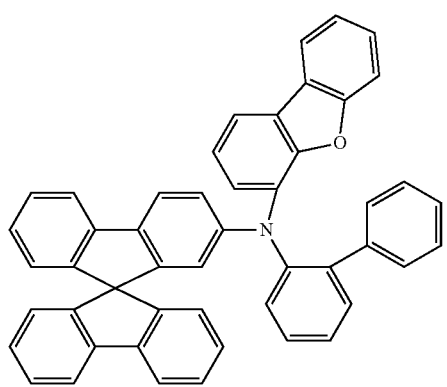 [SMILES: c1ccc(-c2ccccc2N(c2ccc3c(c2)C2(c4ccccc4-c4ccccc42)c2ccccc2-3)c2cccc3c2oc2ccccc23)cc1]
(151)
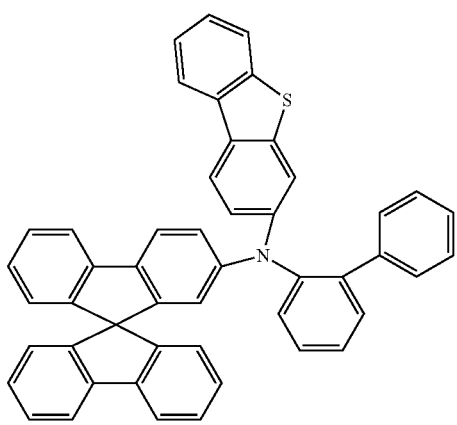 [SMILES: c1ccc(-c2ccccc2N(c2ccc3c(c2)C2(c4ccccc4-c4ccccc42)c2ccccc2-3)c2ccc3c(c2)sc2ccccc23)cc1]
(152)
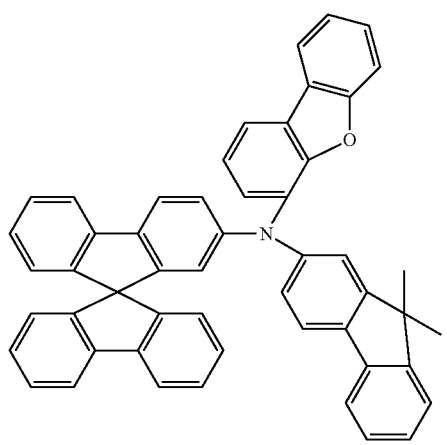 [SMILES: CC1(C)c2ccccc2-c2ccc(N(c3ccc4c(c3)C3(c5ccccc5-c5ccccc53)c3ccccc3-4)c3cccc4c3oc3ccccc34)cc21]

-continued
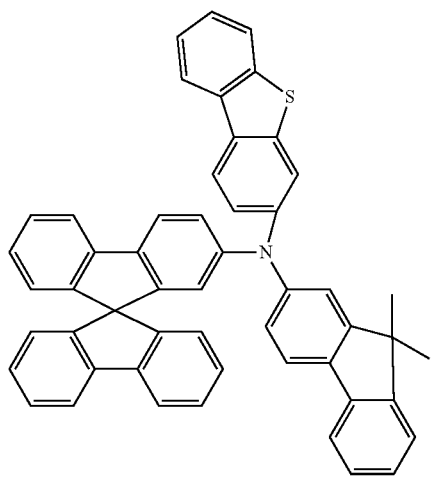 [SMILES: CC1(C)c2ccccc2-c2ccc(N(c3ccc4c(c3)C3(c5ccccc5-c5ccccc53)c3ccccc3-4)c3ccc4c(c3)sc3ccccc34)cc21]
(153)
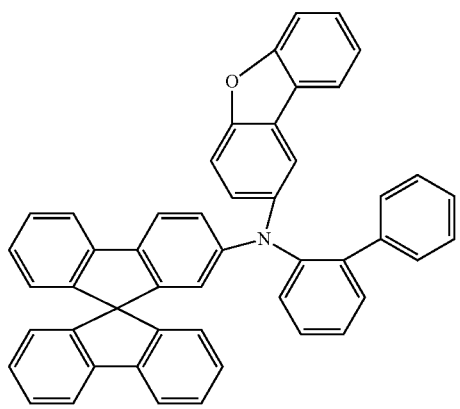 [SMILES: c1ccc(-c2ccccc2N(c2ccc3c(c2)C2(c4ccccc4-c4ccccc42)c2ccccc2-3)c2ccc3oc4ccccc4c3c2)cc1]
(154)
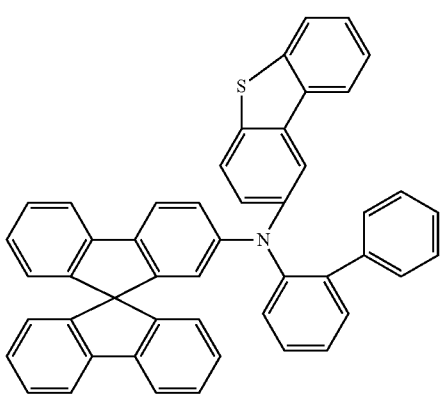 [SMILES: c1ccc(-c2ccccc2N(c2ccc3c(c2)C2(c4ccccc4-c4ccccc42)c2ccccc2-3)c2ccc3sc4ccccc4c3c2)cc1]
(155)

-continued
(156)
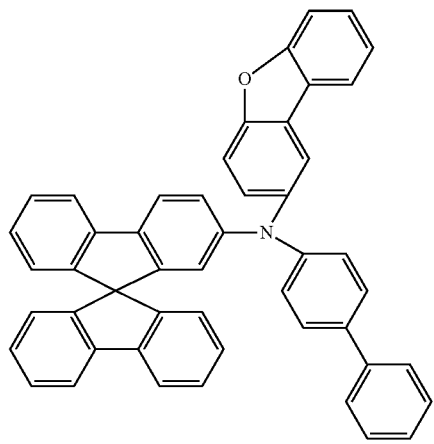 [SMILES: c1ccc(-c2ccc(N(c3ccc4c(c3)C3(c5ccccc5-c5ccccc53)c3ccccc3-4)c3ccc4oc5ccccc5c4c3)cc2)cc1]
(157)
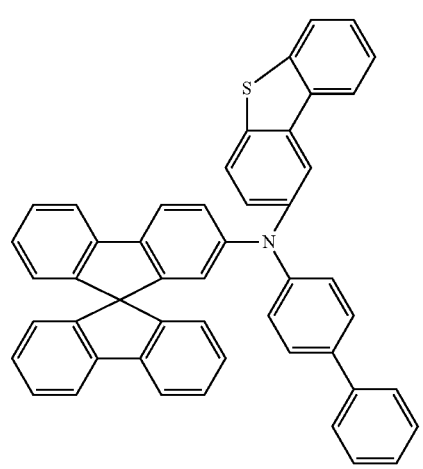 [SMILES: c1ccc(-c2ccc(N(c3ccc4c(c3)C3(c5ccccc5-c5ccccc53)c3ccccc3-4)c3ccc4sc5ccccc5c4c3)cc2)cc1]
(158)
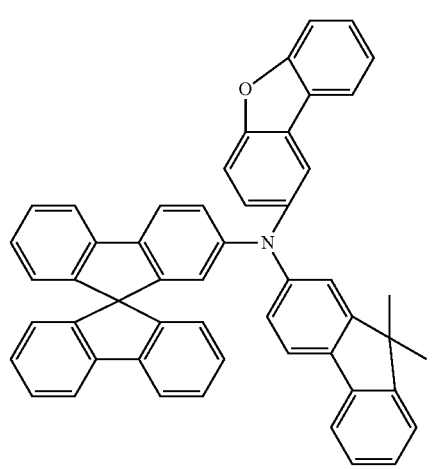 [SMILES: CC1(C)c2ccccc2-c2ccc(N(c3ccc4c(c3)C3(c5ccccc5-c5ccccc53)c3ccccc3-4)c3ccc4oc5ccccc5c4c3)cc21]

-continued
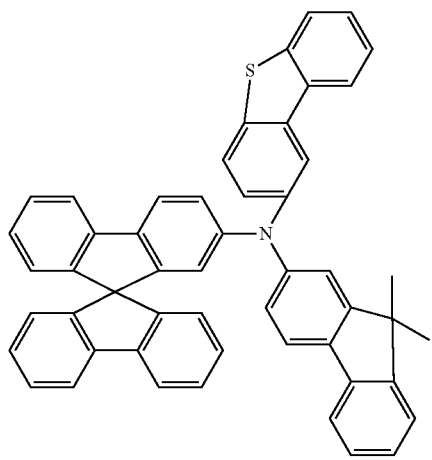 [SMILES: CC1(C)c2ccccc2-c2ccc(N(c3ccc4c(c3)C3(c5ccccc5-c5ccccc53)c3ccccc3-4)c3ccc4sc5ccccc5c4c3)cc21]
(159)
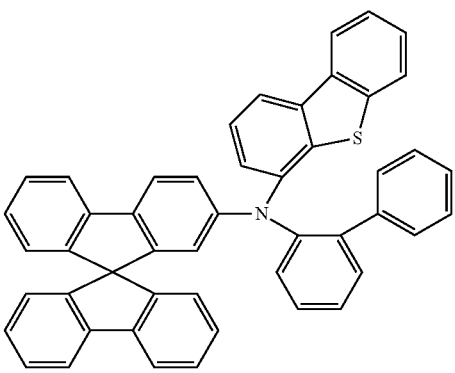 [SMILES: c1ccc(-c2ccccc2N(c2ccc3c(c2)C2(c4ccccc4-c4ccccc42)c2ccccc2-3)c2cccc3c2sc2ccccc23)cc1]
(160)
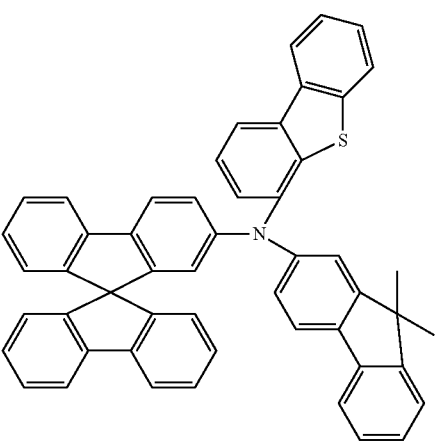 [SMILES: CC1(C)c2ccccc2-c2ccc(N(c3ccc4c(c3)C3(c5ccccc5-c5ccccc53)c3ccccc3-4)c3cccc4c3sc3ccccc34)cc21]
(161)

(162)
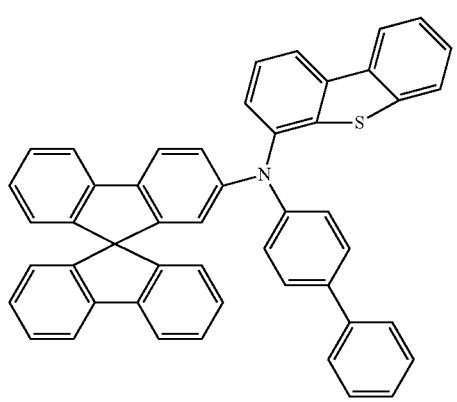 [SMILES: c1ccc(-c2ccc(N(c3ccc4c(c3)C3(c5ccccc5-c5ccccc53)c3ccccc3-4)c3cccc4c3sc3ccccc34)cc2)cc1]
(163)
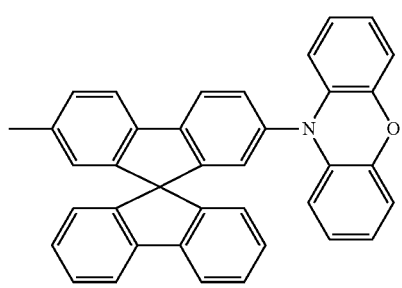 [SMILES: Cc1ccc2c(c1)C1(c3ccccc3-c3ccccc31)c1cc(N3c4ccccc4Oc4ccccc43)ccc1-2]
(164)
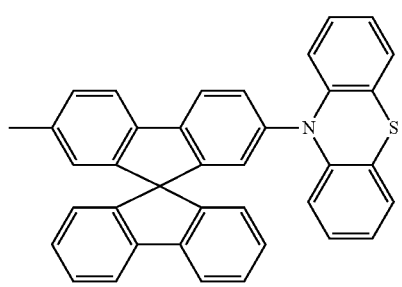 [SMILES: Cc1ccc2c(c1)C1(c3ccccc3-c3ccccc31)c1cc(N3c4ccccc4Sc4ccccc43)ccc1-2]
(165)
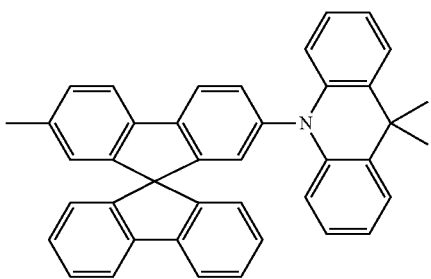
(166)
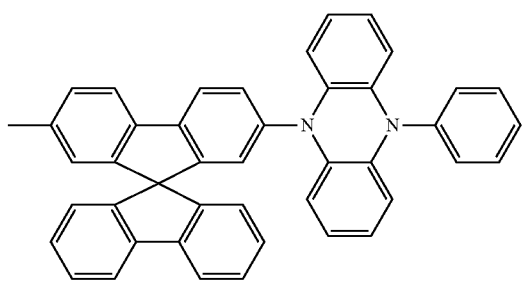 [SMILES: Cc1ccc2c(c1)C1(c3ccccc3-c3ccccc31)c1cc(N3c4ccccc4N(c4ccccc4)c4ccccc43)ccc1-2]

-continued
(167)
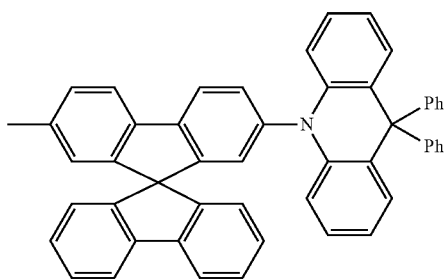 [SMILES: Cc1ccc2c(c1)C1(c3ccccc3-c3ccccc31)c1cc(N3c4ccccc4C(c4ccccc4)(c4ccccc4)c4ccccc43)ccc1-2]
(168)
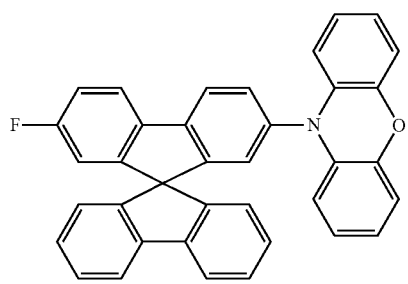 [SMILES: Fc1ccc2c(c1)C1(c3ccccc3-c3ccccc31)c1cc(N3c4ccccc4Oc4ccccc43)ccc1-2]
(169)
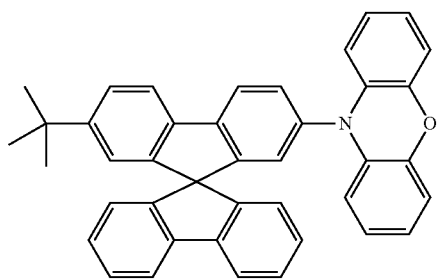 [SMILES: CC(C)(C)c1ccc2c(c1)C1(c3ccccc3-c3ccccc31)c1cc(N3c4ccccc4Oc4ccccc43)ccc1-2]
(170)
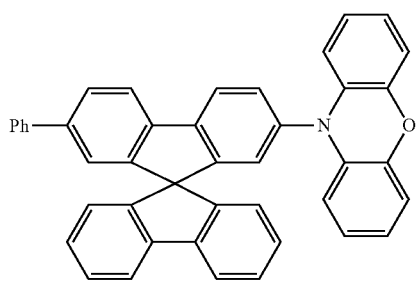 [SMILES: c1ccc(-c2ccc3c(c2)C2(c4ccccc4-c4ccccc42)c2cc(N4c5ccccc5Oc5ccccc54)ccc2-3)cc1]
(171)
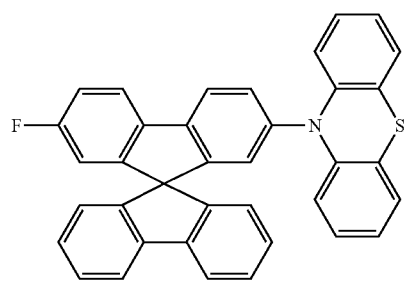 [SMILES: Fc1ccc2c(c1)C1(c3ccccc3-c3ccccc31)c1cc(N3c4ccccc4Sc4ccccc43)ccc1-2]

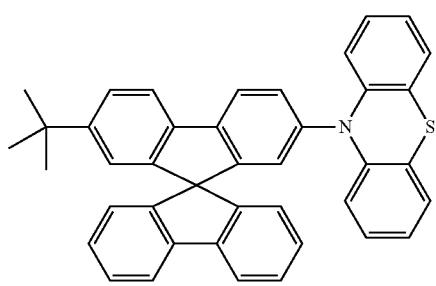 [SMILES: CC(C)(C)c1ccc2c(c1)C1(c3ccccc3-c3ccccc31)c1cc(N3c4ccccc4Sc4ccccc43)ccc1-2]
(172)
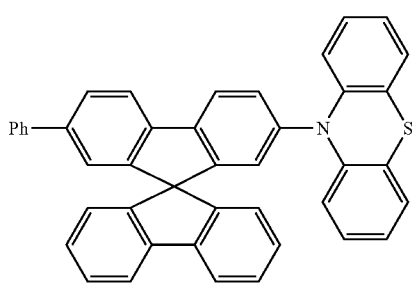 [SMILES: c1ccc(-c2ccc3c(c2)C2(c4ccccc4-c4ccccc42)c2cc(N4c5ccccc5Sc5ccccc54)ccc2-3)cc1]
(173)
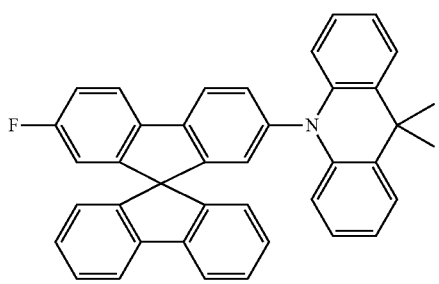 [SMILES: CC1(C)c2ccccc2N(c2ccc3c(c2)C2(c4ccccc4-c4ccccc42)c2cc(F)ccc2-3)c2ccccc21]
(174)
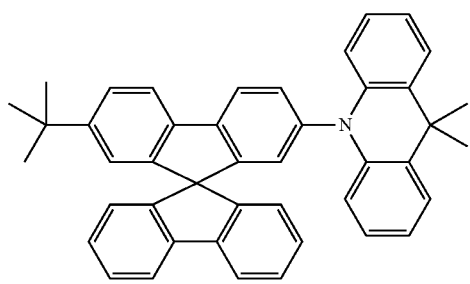 [SMILES: CC(C)(C)c1ccc2c(c1)C1(c3ccccc3-c3ccccc31)c1cc(N3c4ccccc4C(C)(C)c4ccccc43)ccc1-2]
(175)
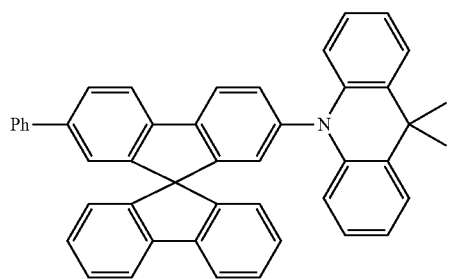 [SMILES: CC1(C)c2ccccc2N(c2ccc3c(c2)C2(c4ccccc4-c4ccccc42)c2cc(-c4ccccc4)ccc2-3)c2ccccc21]
(176)

-continued
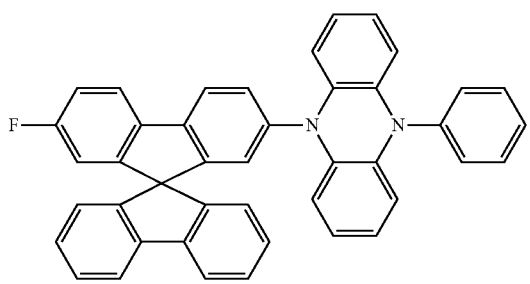 [SMILES: Fc1ccc2c(c1)C1(c3ccccc3-c3ccccc31)c1cc(N3c4ccccc4N(c4ccccc4)c4ccccc43)ccc1-2]
(177)
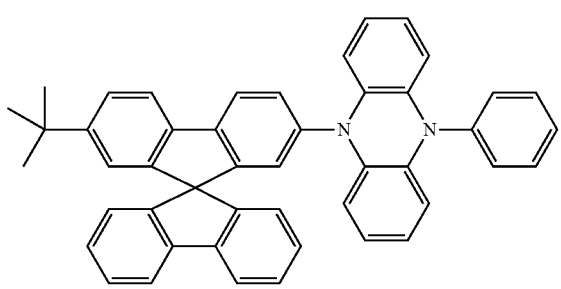 [SMILES: CC(C)(C)c1ccc2c(c1)C1(c3ccccc3-c3ccccc31)c1cc(N3c4ccccc4N(c4ccccc4)c4ccccc43)ccc1-2]
(178)
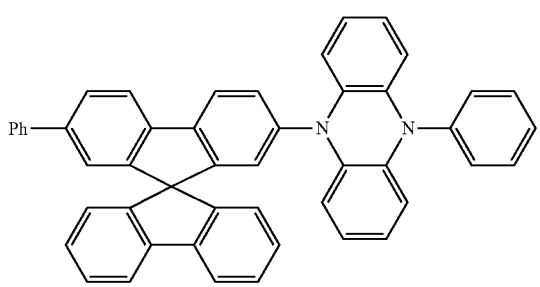 [SMILES: c1ccc(-c2ccc3c(c2)C2(c4ccccc4-c4ccccc42)c2cc(N4c5ccccc5N(c5ccccc5)c5ccccc54)ccc2-3)cc1]
(179)
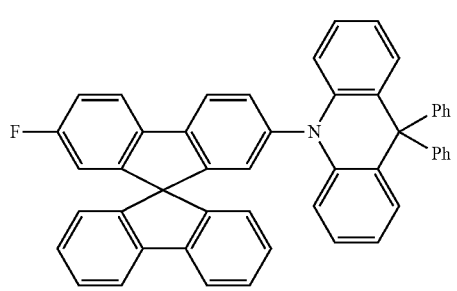 [SMILES: Fc1ccc2c(c1)C1(c3ccccc3-c3ccccc31)c1cc(N3c4ccccc4C(c4ccccc4)(c4ccccc4)c4ccccc43)ccc1-2]
(180)
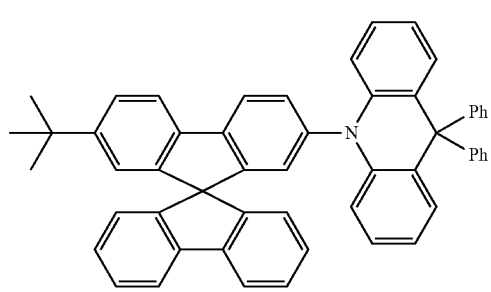 [SMILES: CC(C)(C)c1ccc2c(c1)C1(c3ccccc3-c3ccccc31)c1cc(N3c4ccccc4C(c4ccccc4)(c4ccccc4)c4ccccc43)ccc1-2]
(181)

-continued
(182)
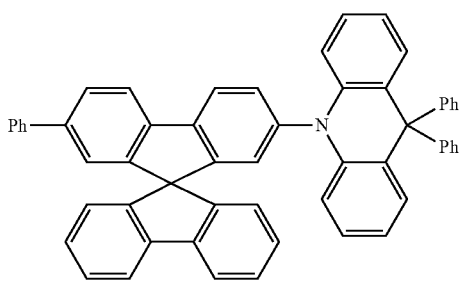 [SMILES: c1ccc(-c2ccc3c(c2)C2(c4ccccc4-c4ccccc42)c2cc(N4c5ccccc5C(c5ccccc5)(c5ccccc5)c5ccccc54)ccc2-3)cc1]
(183)
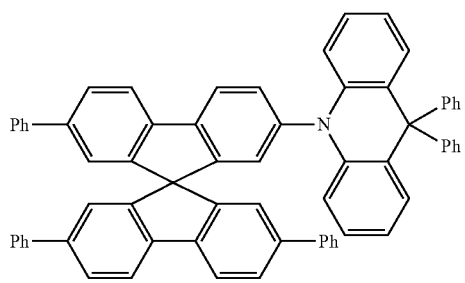 [SMILES: c1ccc(-c2ccc3c(c2)C2(c4cc(-c5ccccc5)ccc4-3)c3cc(-c4ccccc4)ccc3-c3ccc(N4c5ccccc5C(c5ccccc5)(c5ccccc5)c5ccccc54)cc32)cc1]
(184)
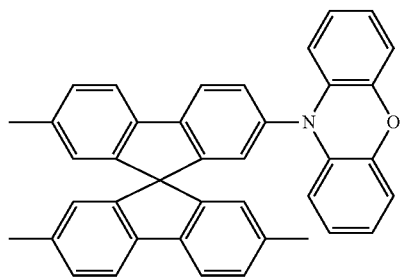 [SMILES: Cc1ccc2c(c1)C1(c3cc(C)ccc3-2)c2cc(C)ccc2-c2ccc(N3c4ccccc4Oc4ccccc43)cc21]
(185)
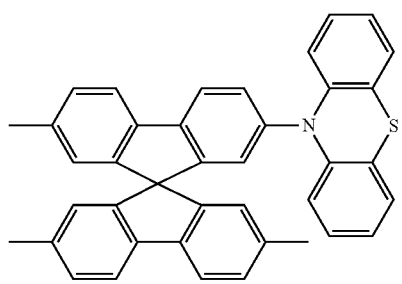 [SMILES: Cc1ccc2c(c1)C1(c3cc(C)ccc3-2)c2cc(C)ccc2-c2ccc(N3c4ccccc4Sc4ccccc43)cc21]
(186)
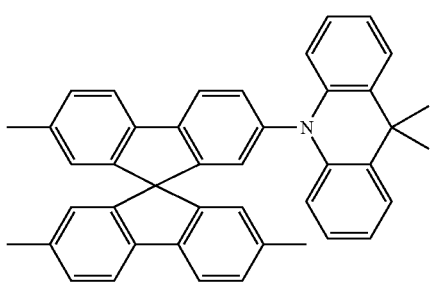

-continued
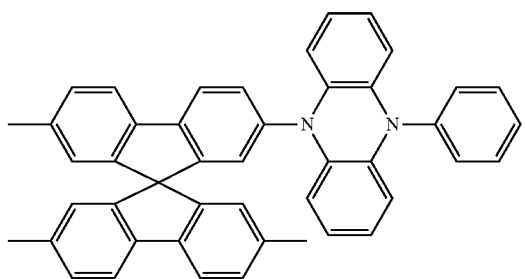 [SMILES: Cc1ccc2c(c1)C1(c3cc(C)ccc3-2)c2cc(C)ccc2-c2ccc(N3c4ccccc4N(c4ccccc4)c4ccccc43)cc21]
(187)
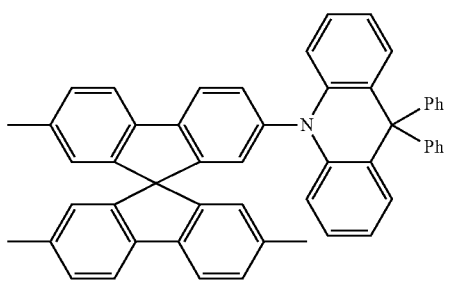 [SMILES: Cc1ccc2c(c1)C1(c3cc(C)ccc3-2)c2cc(C)ccc2-c2ccc(N3c4ccccc4C(c4ccccc4)(c4ccccc4)c4ccccc43)cc21]
(188)
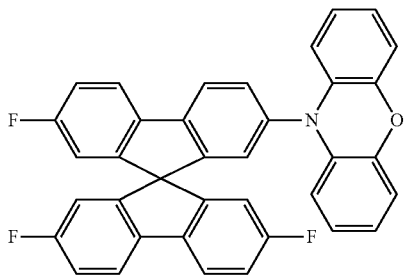 [SMILES: Fc1ccc2c(c1)C1(c3cc(F)ccc3-2)c2cc(F)ccc2-c2ccc(N3c4ccccc4Oc4ccccc43)cc21]
(189)
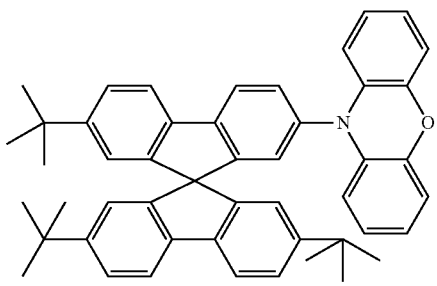 [SMILES: CC(C)(C)c1ccc2c(c1)C1(c3cc(N4c5ccccc5Oc5ccccc54)ccc3-2)c2cc(C(C)(C)C)ccc2-c2ccc(C(C)(C)C)cc21]
(190)
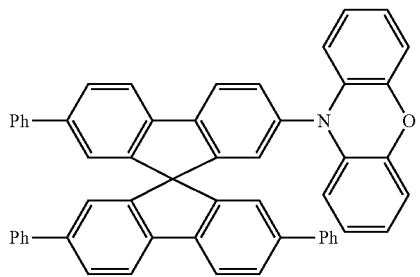 [SMILES: c1ccc(-c2ccc3c(c2)C2(c4cc(-c5ccccc5)ccc4-3)c3cc(-c4ccccc4)ccc3-c3ccc(N4c5ccccc5Oc5ccccc54)cc32)cc1]
(191)

(192)
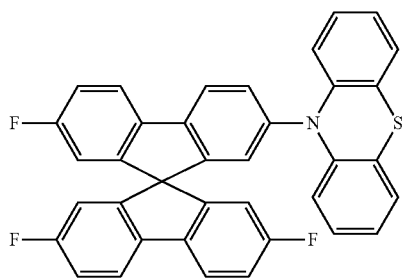 [SMILES: Fc1ccc2c(c1)C1(c3cc(F)ccc3-2)c2cc(F)ccc2-c2ccc(N3c4ccccc4Sc4ccccc43)cc21]
(193)
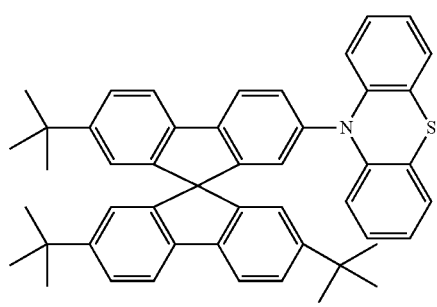 [SMILES: CC(C)(C)c1ccc2c(c1)C1(c3cc(N4c5ccccc5Sc5ccccc54)ccc3-2)c2cc(C(C)(C)C)ccc2-c2ccc(C(C)(C)C)cc21]
(194)
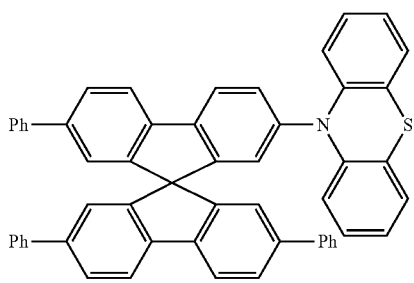 [SMILES: c1ccc(-c2ccc3c(c2)C2(c4cc(-c5ccccc5)ccc4-3)c3cc(-c4ccccc4)ccc3-c3ccc(N4c5ccccc5Sc5ccccc54)cc32)cc1]
(195)
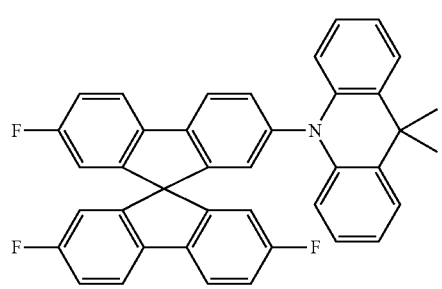 [SMILES: CC1(C)c2ccccc2N(c2ccc3c(c2)C2(c4cc(F)ccc4-c4ccc(F)cc42)c2cc(F)ccc2-3)c2ccccc21]
(196)
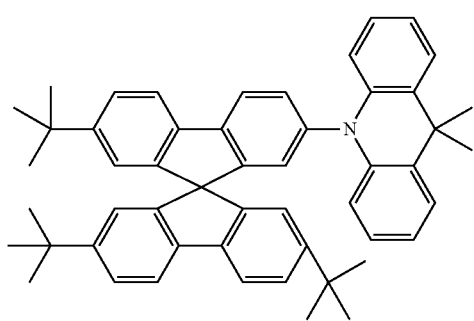 [SMILES: CC(C)(C)c1ccc2c(c1)C1(c3cc(N4c5ccccc5C(C)(C)c5ccccc54)ccc3-2)c2cc(C(C)(C)C)ccc2-c2ccc(C(C)(C)C)cc21]

-continued
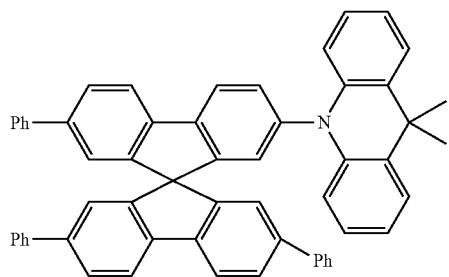 [SMILES: CC1(C)c2ccccc2N(c2ccc3c(c2)C2(c4cc(-c5ccccc5)ccc4-c4ccc(-c5ccccc5)cc42)c2cc(-c4ccccc4)ccc2-3)c2ccccc21]
(197)
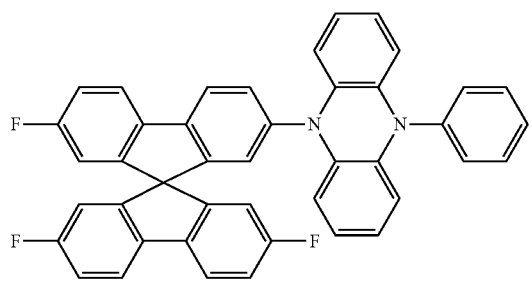 [SMILES: Fc1ccc2c(c1)C1(c3cc(F)ccc3-2)c2cc(F)ccc2-c2ccc(N3c4ccccc4N(c4ccccc4)c4ccccc43)cc21]
(198)
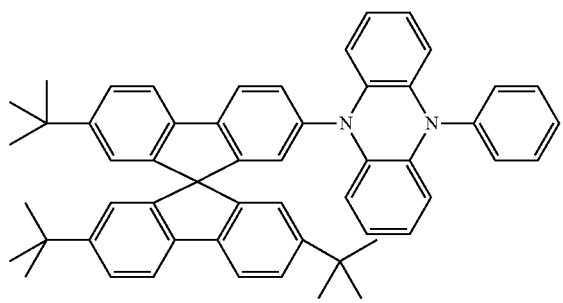 [SMILES: CC(C)(C)c1ccc2c(c1)C1(c3cc(N4c5ccccc5N(c5ccccc5)c5ccccc54)ccc3-2)c2cc(C(C)(C)C)ccc2-c2ccc(C(C)(C)C)cc21]
(199)
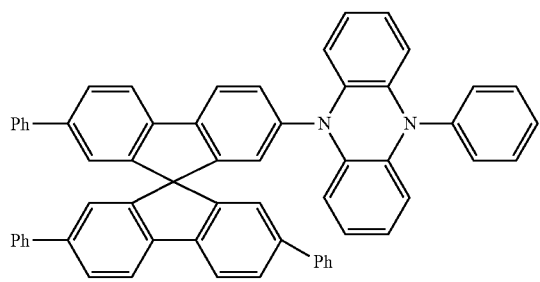 [SMILES: c1ccc(-c2ccc3c(c2)C2(c4cc(-c5ccccc5)ccc4-3)c3cc(-c4ccccc4)ccc3-c3ccc(N4c5ccccc5N(c5ccccc5)c5ccccc54)cc32)cc1]
(200)
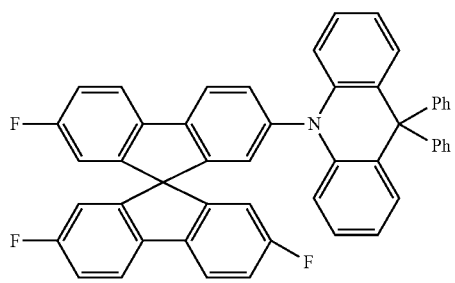 [SMILES: Fc1ccc2c(c1)C1(c3cc(F)ccc3-2)c2cc(F)ccc2-c2ccc(N3c4ccccc4C(c4ccccc4)(c4ccccc4)c4ccccc43)cc21]
(201)

-continued (202)

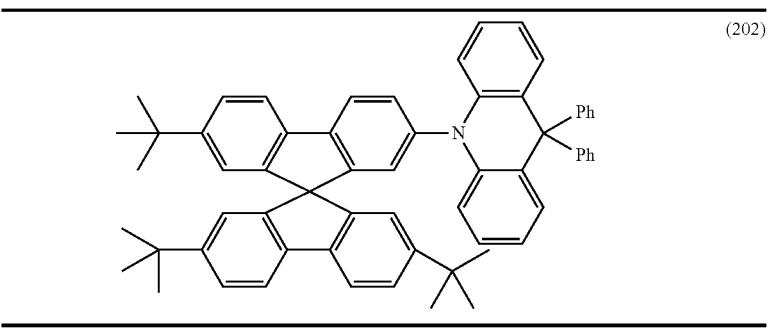

The compounds according to the invention can be prepared by synthetic steps known to the person skilled in the art, such as, for example, bromination, Ullmann arylation, Hartwig-Buchwald coupling, etc. In particular, the compounds can be synthesised from a corresponding halogen-substituted spirobifluorene by introduction of the amino group, as shown in Scheme 1. It is either possible here firstly to introduce a primary amine having a substituent $Ar^1$ and to introduce the group $Ar^2$ in a further coupling reaction, as shown in Scheme 1a). It is likewise possible to introduce the secondary amine $Ar^1Ar^2NH$ directly in one step, as shown in Scheme 1b). Suitable as group X on the spirobifluorene are reactive leaving groups, such as, for example, Cl, Br, I, triflate or tosylate. Suitable coupling reactions are, for example, Hartwig-Buchwald or Ullmann coupling reactions. The reaction conditions which can be used for these coupling reactions are known to the person skilled in the art of organic synthesis.

Scheme 1 a)

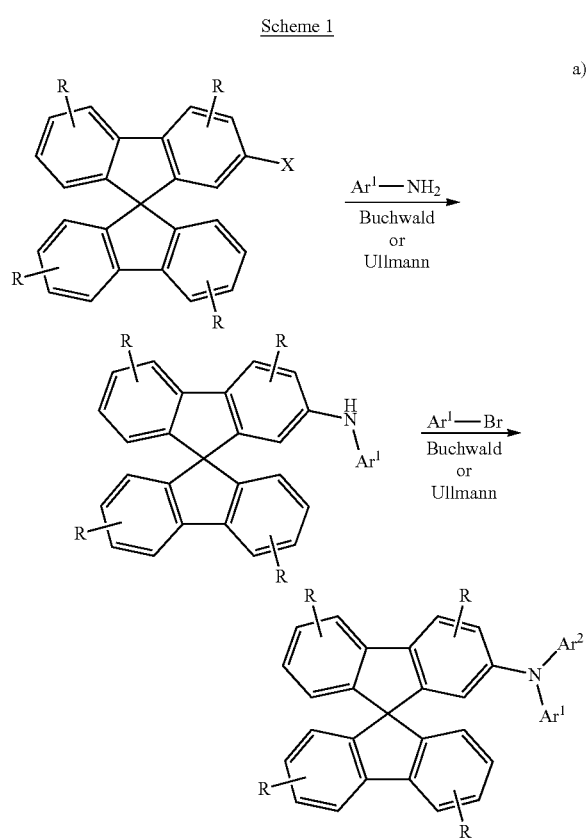

-continued b)

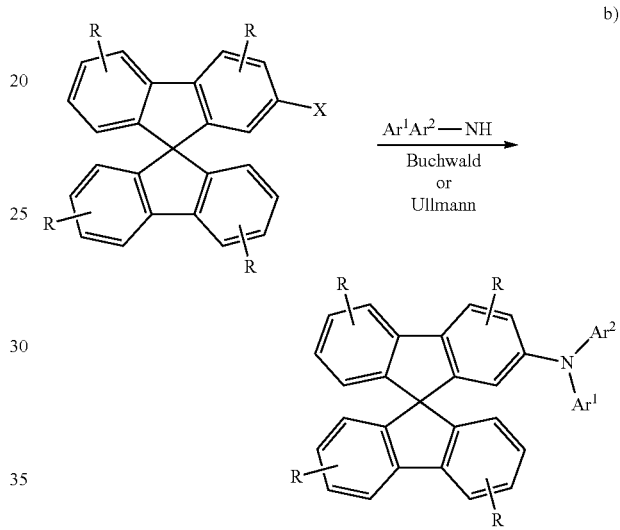

For compounds where p=1 or 2, the group Ar—$NAr^1Ar^2$ can likewise be introduced via a metal-catalysed coupling reaction, for example via a Suzuki coupling or a Stille coupling.

The present invention therefore furthermore relates to a process for the preparation of a compound of the formula (1) by coupling a spirobifluorene derivative which is substituted in the 2-position by a reactive leaving group to
a) a primary amine, followed by coupling to a further aromatic group which is substituted by a reactive leaving group, or
b) to a secondary amine, or
c) to a triarylamine derivative.

The reactive leaving group here is preferably selected from Cl, Br, I, triflate or tosylate or, for a Suzuki coupling, also a boronic acid or boronic acid derivative, in particular a boronic acid ester.

The coupling reaction is preferably selected from Hartwig-Buchwald couplings, Ullmann couplings and Suzuki couplings.

The compounds according to the invention are suitable for use in an electronic device. An electronic device here is taken to mean a device which comprises at least one layer which comprises at least one organic compound. However, the component here may also comprise inorganic materials or also layers built up entirely from inorganic materials.

The present invention therefore furthermore relates to the use of the compounds according to the invention in an electronic device, in particular in an organic electroluminescent device.

The present invention again furthermore relates to an electronic device comprising at least one compound according to the invention. The preferences stated above likewise apply to the electronic devices.

The electronic device is preferably selected from the group consisting of organic electroluminescent devices (organic light-emitting diodes, OLEDs), organic integrated circuits (O-ICs), organic field-effect transistors (O-FETs), organic thin-film transistors (O-TFTs), organic light-emitting transistors (O-LETs), organic solar cells (O-SCs), organic dye-sensitised solar cells (ODSSCs), organic optical detectors, organic photoreceptors, organic field-quench devices (O-FQDs), light-emitting electrochemical cells (LECs), organic laser diodes (O-lasers) and organic plasmon emitting devices (D. M. Koller et al., Nature Photonics 2008, 1-4), but preferably organic electroluminescent devices (OLEDs), particularly preferably phosphorescent OLEDs.

The organic electroluminescent devices and the light-emitting electrochemical cells can be employed for various applications, for example for monochromatic or polychromatic displays, for lighting applications or for medical and/or cosmetic applications, for example in phototherapy.

The organic electroluminescent device comprises a cathode, an anode and at least one emitting layer. Apart from these layers, it may also comprise further layers, for example in each case one or more hole-injection layers, hole-transport layers, hole-blocking layers, electron-transport layers, electron-injection layers, exciton-blocking layers, electron-blocking layers and/or charge-generation layers. Interlayers, which have, for example, an exciton-blocking function, may likewise be introduced between two emitting layers. However, it should be pointed out that each of these layers does not necessarily have to be present.

The organic electroluminescent device here may comprise one emitting layer or a plurality of emitting layers. If a plurality of emission layers is present, these preferably have in total a plurality of emission maxima between 380 nm and 750 nm, resulting overall in white emission, i.e. various emitting compounds which are able to fluoresce or phosphoresce are used in the emitting layers. Particular preference is given to systems having three emitting layers, where the three layers exhibit blue, green and orange or red emission (for the basic structure see, for example, WO 2005/011013). It is possible here for all emitting layers to be fluorescent or for all emitting layers to be phosphorescent or for one or more emitting layers to be fluorescent and one or more other layers to be phosphorescent.

The compound according to the invention in accordance with the embodiments indicated above can be employed here in different layers, depending on the precise structure. Preference is given to an organic electroluminescent device comprising a compound of the formula (1) or the preferred embodiments as hole-transport material in a hole-transport or hole-injection or exciton-blocking layer or as matrix material for fluorescent or phosphorescent emitters, in particular for phosphorescent emitters. The preferred embodiments indicated above also apply to the use of the materials in organic electronic devices.

In a preferred embodiment of the invention, the compound of the formula (1) or the preferred embodiments is employed as hole-transport or hole-injection material in a hole-transport or hole-injection layer. The emitting layer here can be fluorescent or phosphorescent. A hole-injection layer in the sense of the present invention is a layer which is directly adjacent to the anode. A hole-transport layer in the sense of the present invention is a layer which is located between a hole-injection layer and an emitting layer.

In still a further preferred embodiment of the invention, the compound of the formula (1) or the preferred embodiments is employed in an exciton-blocking layer. An exciton-blocking layer is taken to mean a layer which is directly adjacent to an emitting layer on the anode side.

The compound of the formula (1) or the preferred embodiments is particularly preferably employed in a hole-transport or exciton-blocking layer.

In a further preferred embodiment of the invention, the compound of the formula (1) or the preferred embodiments is employed as matrix material for a fluorescent or phosphorescent compound, in particular for a phosphorescent compound, in an emitting layer. The organic electroluminescent device here may comprise one emitting layer or a plurality of emitting layers, where at least one emitting layer comprises at least one compound according to the invention as matrix material.

If the compound of the formula (1) or the preferred embodiments is employed as matrix material for an emitting compound in an emitting layer, it is preferably employed in combination with one or more phosphorescent materials (triplet emitters). Phosphorescence in the sense of this invention is taken to mean the luminescence from an excited state having a spin multiplicity >1, in particular from an excited triplet state. For the purposes of this application, all luminescent complexes containing transition metals or lanthanoids, in particular all luminescent iridium, platinum and copper complexes, are to be regarded as phosphorescent compounds.

The mixture comprising the compound of the formula (1) or the preferred embodiments and the emitting compound comprises between 99.9 and 1% by weight, preferably between 99 and 10% by weight, particularly preferably between 97 and 60% by weight, in particular between 95 and 80% by weight, of the compound of the formula (1) or the preferred embodiments, based on the entire mixture comprising emitter and matrix material. Correspondingly, the mixture comprises between 0.1 and 99% by weight, preferably between 1 and 90% by weight, particularly preferably between 3 and 40% by weight, in particular between 5 and 20% by weight, of the emitter, based on the entire mixture comprising emitter and matrix material. The limits indicated above apply, in particular, if the layer is applied from solution. If the layer is applied by vacuum evaporation, the same numerical values apply, with the percentage in this case being indicated in % by vol. in each case.

A particularly preferred embodiment of the present invention is the use of the compound of the formula (1) or the preferred embodiments as matrix material for a phosphorescent emitter in combination with a further matrix material. Particularly suitable matrix materials which can be employed in combination with the compounds of the formula (1) or the preferred embodiments are aromatic ketones, aromatic phosphine oxides or aromatic sulfoxides or sulfones, for example in accordance with WO 2004/013080, WO 2004/093207, WO 2006/005627 or WO 2010/006680, triarylamines, carbazole derivatives, for example CBP (N,N-biscarbazolylbiphenyl), m-CBP or the carbazole derivatives disclosed in WO 2005/039246, US 2005/0069729, JP 2004/288381, EP 1205527 or WO 2008/086851, indolocarbazole derivatives, for example in accordance with WO 2007/063754 or WO 2008/056746, indenocarbazole derivatives, for example in accordance with WO 2010/136109 or WO 2011/000455, azacarbazole derivatives, for example in accordance with EP 1617710, EP 1617711, EP 1731584, JP 2005/347160, bipolar matrix materials, for example in accordance with WO 2007/137725, silanes, for example in accordance with WO 2005/111172, azaboroles or boronic esters, for example in accordance with WO 2006/117052, triazine derivatives, for example in accordance with WO 2010/015306, WO 2007/063754 or WO 08/056,746, zinc complexes, for example in accordance with EP 652273 or WO 2009/062578, fluorene derivatives, for example in accordance with WO 2009/124627, diazasilole or tetraazasilole derivatives, for example in accordance with WO 2010/054729, diazaphosphole derivatives, for example in accordance with WO 2010/054730, or bridged carbazole derivatives, for example in accordance with US 2009/0136779, WO 2010/050778, WO 2011/042107 or in accordance with the unpublished application DE 102010005697.9. It is furthermore possible to use an electronically neutral co-host which has neither hole-transporting nor electron-transporting properties, as described, for example, in WO 2010/108579.

It is likewise possible to use two or more phosphorescent emitters in the mixture. In this case, the emitter which emits at shorter wavelength acts as co-host in the mixture.

Suitable phosphorescent compounds (=triplet emitters) are, in particular, compounds which emit light, preferably in the visible region, on suitable excitation and in addition contain at least one atom having an atomic number greater than 20, preferably greater than 38 and less than 84, particularly preferably greater than 56 and less than 80, in particular a metal having this atomic number. The phosphorescent emitters used are preferably compounds which contain copper, molybdenum, tungsten, rhenium, ruthenium, osmium, rhodium, iridium, palladium, platinum, silver, gold or europium, in particular compounds which contain iridium, platinum or copper.

Examples of the emitters described above are revealed by the applications WO 2000/70655, WO 2001/41512, WO 2002/02714, WO 2002/15645, EP 1191613, EP 1191612, EP 1191614, WO 2005/033244, WO 2005/019373, US 2005/0258742, WO 2009/146770, WO 2010/015307, WO 2010/031485, WO 2010/054731, WO 2010/054728, WO 2010/086089, WO 2010/099852 and WO 2010/102709. Also suitable are, for example, the complexes in accordance with the unpublished applications EP 10006208.2 and DE 102010027317.1. In general, all phosphorescent complexes as used in accordance with the prior art for phosphorescent OLEDs and as are known to the person skilled in the art in the area of organic electroluminescence are suitable, and the person skilled in the art will be able to use further phosphorescent complexes without inventive step.

In a further embodiment of the invention, the organic electroluminescent device according to the invention does not comprise a separate hole-injection layer and/or hole-transport layer and/or hole-blocking layer and/or electron-transport layer, i.e. the emitting layer is directly adjacent to the hole-injection layer or the anode, and/or the emitting layer is directly adjacent to the electron-transport layer or the electron-injection layer or the cathode, as described, for example, in WO 2005/053051. It is furthermore possible to use a metal complex which is identical or similar to the metal complex in the emitting layer as hole-transport or hole-injection material directly adjacent to the emitting layer, as described, for example, in WO 2009/030981.

It is furthermore possible to use the compound of the formula (1) or the preferred embodiments both in a hole-transport layer or exciton-blocking layer and as matrix in an emitting layer.

In the further layers of the organic electroluminescent device according to the invention, it is possible to use all materials as usually employed in accordance with the prior art. The person skilled in the art will therefore be able, without inventive step, to employ all materials known for organic electroluminescent devices in combination with the compounds of the formula (1) according to the invention or the preferred embodiments.

Preference is furthermore given to an organic electroluminescent device, characterised in that one or more layers are applied by means of a sublimation process, in which the materials are vapour-deposited in vacuum sublimation units at an initial pressure of usually less than $10^{-5}$ mbar, preferably less than $10^{-6}$ mbar. However, it is also possible for the initial pressure to be even lower, for example less than $10^{-7}$ mbar.

Preference is likewise given to an organic electroluminescent device, characterised in that one or more layers are applied by means of the OVPD (organic vapour phase deposition) process or with the aid of carrier-gas sublimation, in which the materials are applied at a pressure between $10^{-5}$ mbar and 1 bar. A special case of this process is the OVJP (organic vapour jet printing) process, in which the materials are applied directly through a nozzle and thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, LITI (light induced thermal imaging, thermal transfer printing), ink-jet printing, screen printing, flexographic printing, offset printing or nozzle printing. Soluble compounds, which are obtained, for example, by suitable substitution, are necessary for this purpose. These processes are also particularly suitable for the compounds according to the invention, since these generally have very good solubility in organic solvents.

Also possible are hybrid processes, in which, for example, one or more layers are applied from solution and one or more further layers are applied by vapour deposition. Thus, for example, the emitting layer can be applied from solution and the electron-transport layer by vapour deposition.

These processes are generally known to the person skilled in the art and can be applied by him without inventive step to organic electroluminescent devices comprising the compounds according to the invention.

The processing of the compounds according to the invention from the liquid phase, for example by spin coating or by printing processes, requires formulations of the compounds according to the invention. These formulations can be, for example, solutions, dispersions or mini-emulsions. It may be preferred to use mixtures of two or more solvents for this purpose. Suitable and preferred solvents are, for example, toluene, anisole, o-, m- or p-xylene, methyl benzoate, dimethylanisole, mesitylene, tetralin, veratrol, THF, methyl-THF, THP, chlorobenzene, dioxane or mixtures of these solvents.

The present invention therefore furthermore relates to a formulation, in particular a solution, dispersion or mini-emulsion, comprising at least one compound of the formula (1) or the preferred embodiments indicated above and at least one solvent, in particular an organic solvent. The way in which solutions of this type can be prepared is known to the person skilled in the art and is described, for example, in WO 2002/072714, WO 2003/019694 and the literature cited therein.

The present invention furthermore relates to mixtures comprising at least one compound of the formula (1) or the preferred embodiments indicated above and at least one further compound. The further compound can be, for example, a fluorescent or phosphorescent dopant if the compound according to the invention is used as matrix material. The mixture may then also additionally comprise a further material as additional matrix material.

The compounds according to the invention and the organic electroluminescent devices according to the invention are distinguished by the following surprising advantages over the prior art:

1. The compounds according to the invention are very highly suitable for use in a hole-transport or hole-injection layer in an organic electroluminescent device. They are also suitable, in particular, for use in a layer which is directly adjacent to a phosphorescent emitting layer, since the compounds according to the invention do not extinguish the luminescence.
2. The compounds according to the invention, employed as matrix material for fluorescent or phosphorescent emitters, result in very high efficiencies and long lifetimes. This applies, in particular, if the compounds are employed as matrix material together with a further matrix material and a phosphorescent emitter.
3. The compounds according to the invention, employed in organic electroluminescent devices, result in high efficiencies and in steep current/voltage curves with low use and operating voltages.
4. The compounds according to the invention have high thermal stability and can be sublimed without decomposition and without a residue.
5. The compounds according to the invention have high oxidation stability, which has, in particular, a positive effect on the handling of these compounds and on the storage stability for solutions.

These above-mentioned advantages are not accompanied by an impairment in the other electronic properties.

The invention is explained in greater detail by the following examples, without wishing to restrict it thereby. On the basis of the descriptions, the person skilled in the art will be able to carry out the invention throughout the range disclosed and prepare further compounds according to the invention without inventive step and use them in electronic devices or use the process according to the invention.

EXAMPLES

The following syntheses are carried out under a protective-gas atmosphere, unless indicated otherwise. The starting materials can be purchased from ALDRICH or ABCR. The numbers in square brackets in the case of the starting materials known from the literature are the corresponding CAS numbers.

A1) Biphenyl-2-yl-(9,9'-spirobi-9H-fluoren-2-yl) amine

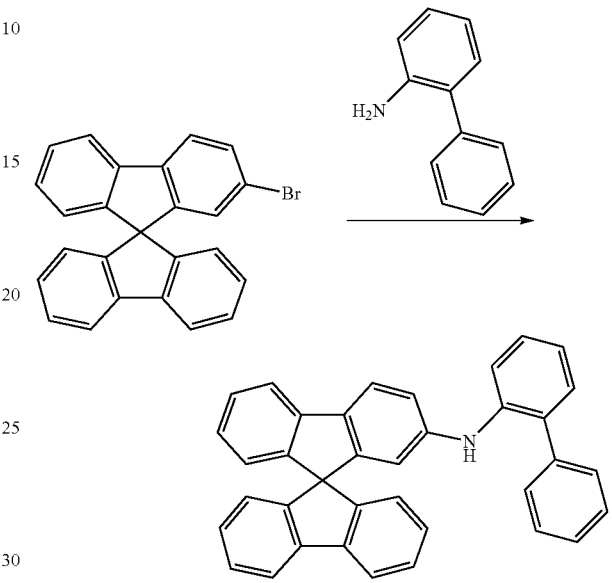

1,1'-Bis(diphenylphosphino)ferrocene (5.89 g, 10.6 mmol), palladium acetate (2.38 g, 10.6 mmol) and sodium tert-butoxide (88.6 g, 921 mmol) are added to a solution of biphenyl-2-ylamine (119.9 g, 709 mmol) and 2-bromo-9,9-spirobifluorene (280.3 g, 709 mmol) in degassed toluene (400 ml), and the mixture is heated under reflux for 20 h. The reaction mixture is cooled to room temperature, diluted with toluene and filtered through Celite. The filtrate is diluted with water and re-extracted with toluene, and the combined organic phases are dried and evaporated in vacuo. The residue is filtered through silica gel (heptane/dichloromethane) and crystallised from isopropanol. The product is obtained in the form of a pale-yellow solid. The yield is 298 g (87%).

The following compounds are obtained analogously:

| Ex. | Starting material 1 | Starting material 2 | Product | Yield |
|---|---|---|---|---|
| A2 | | [92-67-1] | | 90% |

-continued
| Ex. | Starting material 1 | Starting material 2 | Product | Yield |
|---|---|---|---|---|
| A3 | 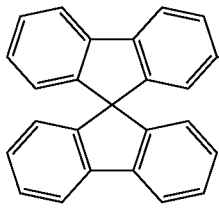 | 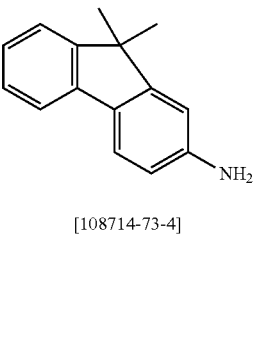 [108714-73-4] | 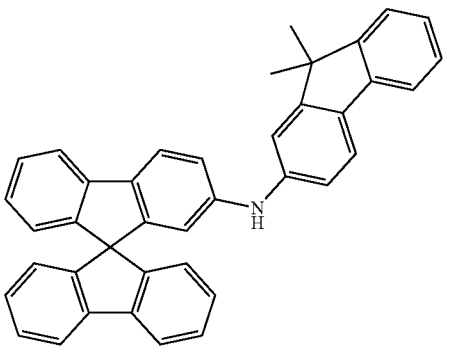 [SMILES: CC1(C)c2ccccc2-c2ccc(Nc3ccc4c(c3)C3(c5ccccc5-c5ccccc53)c3ccccc3-4)cc21] | 87% |
| A4 | 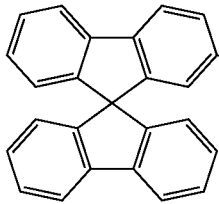 | 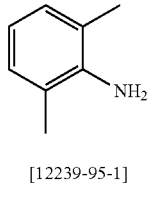 [12239-95-1] | 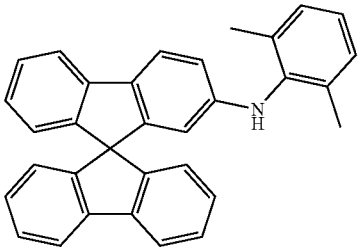 [SMILES: Cc1cccc(C)c1Nc1ccc2c(c1)C1(c3ccccc3-c3ccccc31)c1ccccc1-2] | 68% |
| A5 | 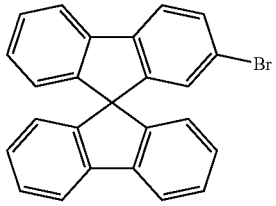 [SMILES: Brc1ccc2c(c1)C1(c3ccccc3-c3ccccc31)c1ccccc1-2] | 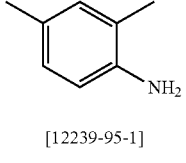 [12239-95-1] | 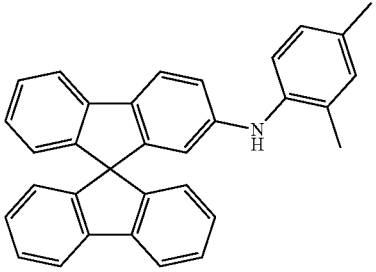 [SMILES: Cc1ccc(Nc2ccc3c(c2)C2(c4ccccc4-c4ccccc42)c2ccccc2-3)c(C)c1] | 69% |
| A6 | 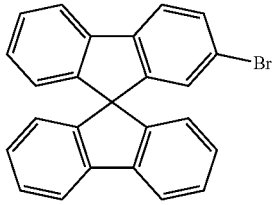 [SMILES: Brc1ccc2c(c1)C1(c3ccccc3-c3ccccc31)c1ccccc1-2] | 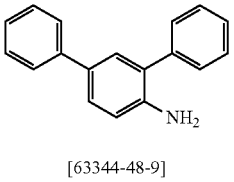 [63344-48-9] | 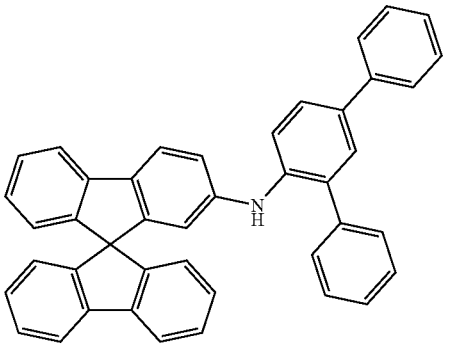 [SMILES: c1ccc(-c2ccc(Nc3ccc4c(c3)C3(c5ccccc5-c5ccccc53)c3ccccc3-4)c(-c3ccccc3)c2)cc1] | 83% |

-continued
| Ex. | Starting material 1 | Starting material 2 | Product | Yield |
|---|---|---|---|---|
| A7 | 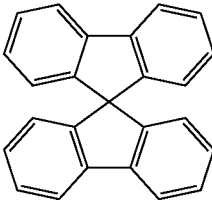 | 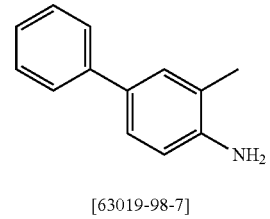[63019-98-7] | 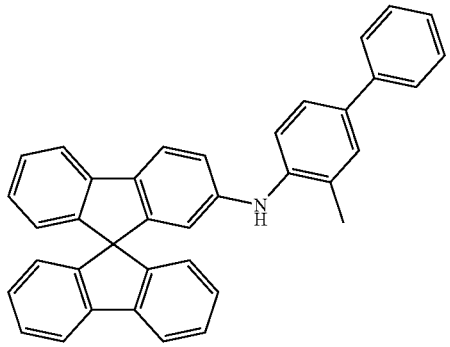 [SMILES: Cc1cc(-c2ccccc2)ccc1Nc1ccc2c(c1)C1(c3ccccc3-c3ccccc31)c1ccccc1-2] | 89% |
| A8 | 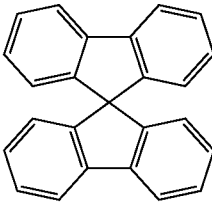 | 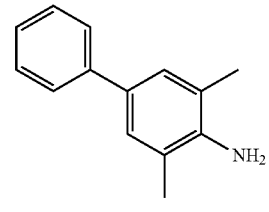[54810-82-1] | 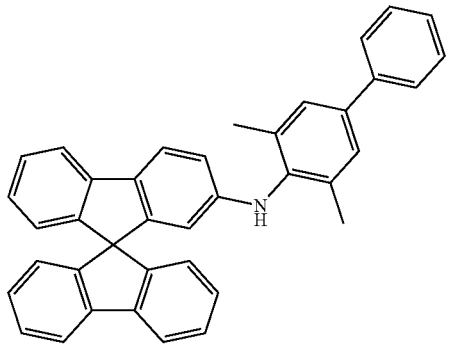 [SMILES: Cc1cc(-c2ccccc2)cc(C)c1Nc1ccc2c(c1)C1(c3ccccc3-c3ccccc31)c1ccccc1-2] | 65% |
| A9 | 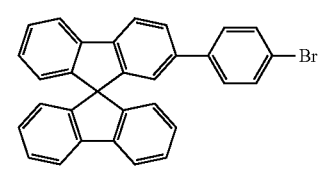 [SMILES: Brc1ccc(-c2ccc3c(c2)C2(c4ccccc4-c4ccccc42)c2ccccc2-3)cc1] | 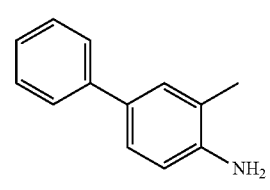[63019-98-7] | 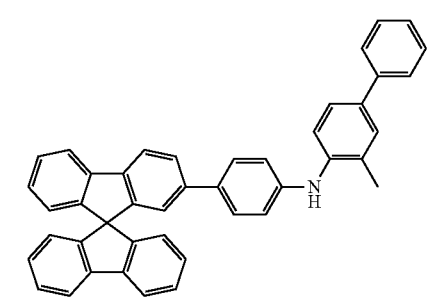 [SMILES: Cc1cc(-c2ccccc2)ccc1Nc1ccc(-c2ccc3c(c2)C2(c4ccccc4-c4ccccc42)c2ccccc2-3)cc1] | 87% |
| A10 | 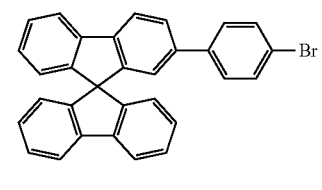 [SMILES: Brc1ccc(-c2ccc3c(c2)C2(c4ccccc4-c4ccccc42)c2ccccc2-3)cc1] | 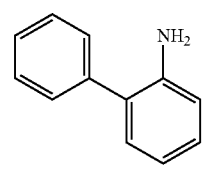 [SMILES: Nc1ccccc1-c1ccccc1][90-41-5] | 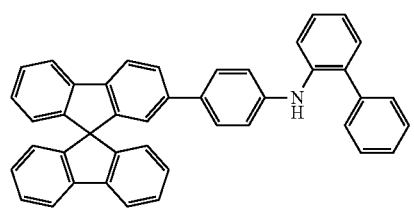 [SMILES: c1ccc(-c2ccccc2Nc2ccc(-c3ccc4c(c3)C3(c5ccccc5-c5ccccc53)c3ccccc3-4)cc2)cc1] | 74% |

| Ex. | Starting material 1 | Starting material 2 | Product | Yield |
|---|---|---|---|---|
| A11 | [118951-68-1] | [171408-76-7] | | 77% |

B1) Biphenyl-4-ylbiphenyl-2-yl-(9,9'-spirobi-9H-fluoren-2-yl)amine

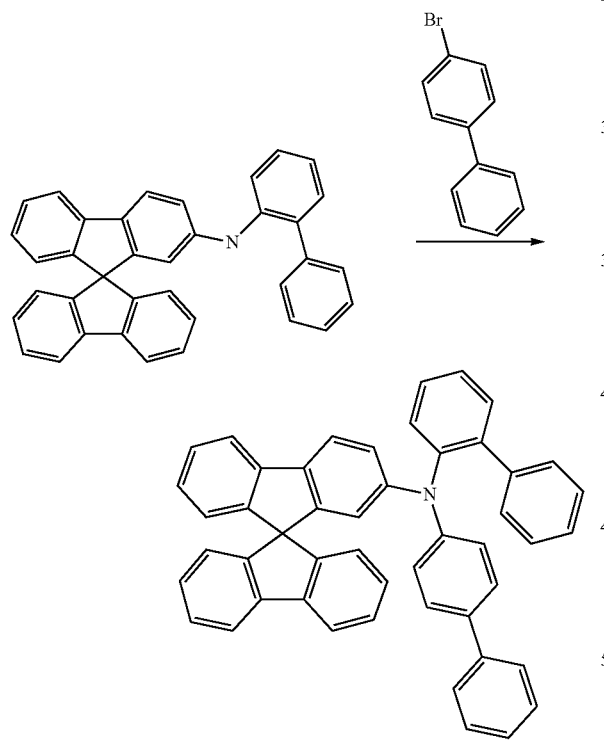

Tri-tert-butylphosphine (4.4 ml of a 1.0 M solution in toluene, 4.4 mmol), palladium acetate (248 mg, 1.1 mmol) and sodium tert-butoxide (16.0 g, 166 mmol) are added to a solution of biphenyl-2-yl-(9,9'-spirobi-9H-fluoren-2-yl)amine (53.0 g, 110 mmol) and 4-bromobiphenyl (32 g, 140 mmol) in degassed toluene (500 ml), and the mixture is heated under reflux for 2 h. The reaction mixture is cooled to room temperature, diluted with toluene and filtered through Celite. The filtrate is evaporated in vacuo, and the residue is crystallised from ethyl acetate/heptane. The crude product is extracted in a Soxhlet extractor (toluene) and purified by zone sublimation in vacuo twice (p=3×10$^{-4}$ mbar, T=298° C.). The product is isolated in the form of a pale-yellow solid (60 g, 87% of theory, purity >99.99% according to HPLC).

The following compounds are obtained analogously:

| Ex. | Starting material 1 | Starting material 2 | Product | Yield |
|---|---|---|---|---|
| B2 | 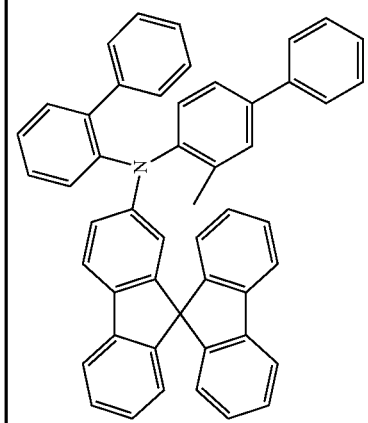 | 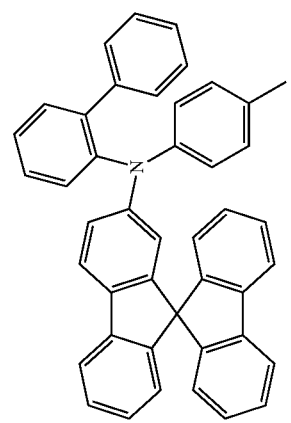 [92022-07-6] | 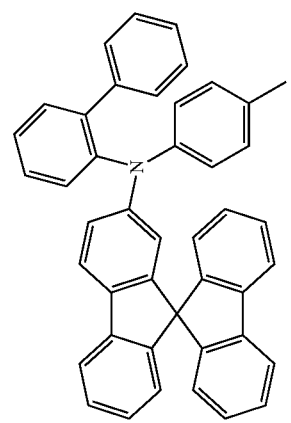 | 70% |
| B3 | 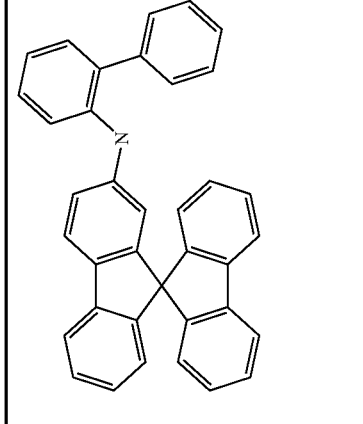 | 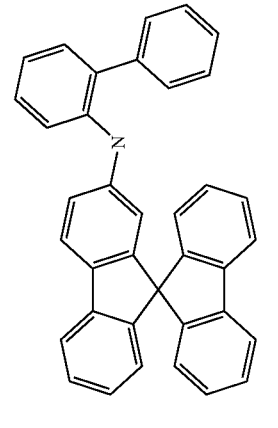 | 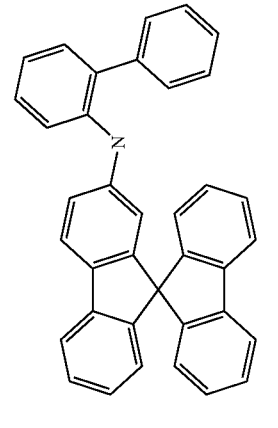 | 72% |

| Ex. | Starting material 1 | Starting material 2 | Product | Yield |
|---|---|---|---|---|
| B4 |  | 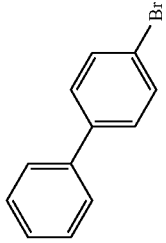 | 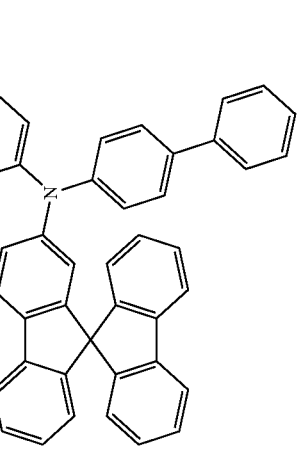 | 79% |
| B5 |  | 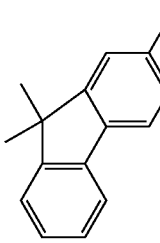 [28320-31-2] | 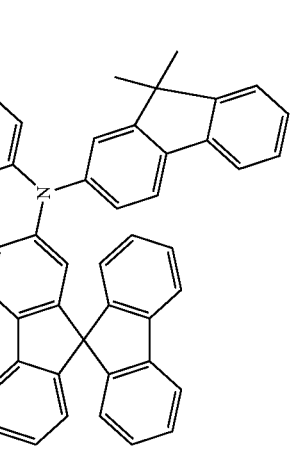 | 77% |

-continued

| Ex. | Starting material 1 | Starting material 2 | Product | Yield |
|---|---|---|---|---|
| B6 | (9,9-dimethylfluoren-2-yl)(9,9'-spirobifluoren-2-yl)amine | 2-bromo-9,9-dimethylfluorene | N,N-bis(9,9-dimethylfluoren-2-yl)(9,9'-spirobifluoren-2-yl)amine | 68% |
| B7 | (9,9-dimethylfluoren-2-yl)(9,9'-spirobifluoren-2-yl)amine | 3-bromobiphenyl [2113-57-7] | N-(biphenyl-3-yl)-N-(9,9-dimethylfluoren-2-yl)(9,9'-spirobifluoren-2-yl)amine | 68% |

-continued
| Ex. | Starting material 1 | Starting material 2 | Product | Yield |
|---|---|---|---|---|
| B8 | 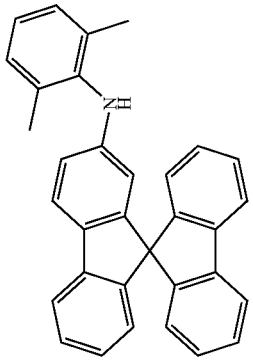 | 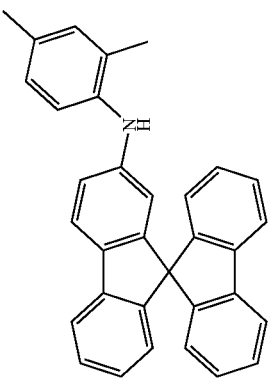 | 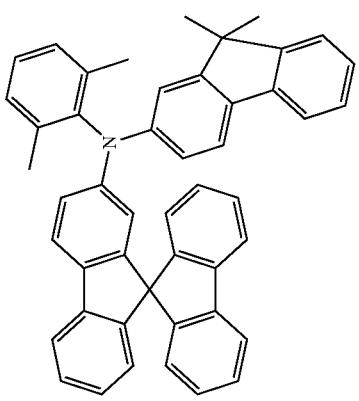 | 68% |
| B9 | 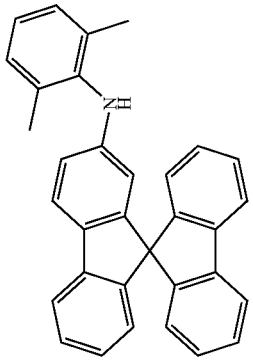 | [583-70-0] | 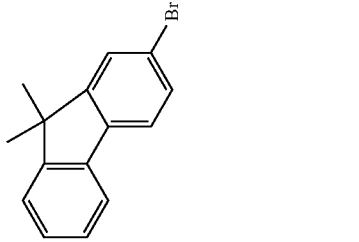 | 63% |

-continued
| Ex. | Starting material 1 | Starting material 2 | Product | Yield |
|---|---|---|---|---|
| B10 | 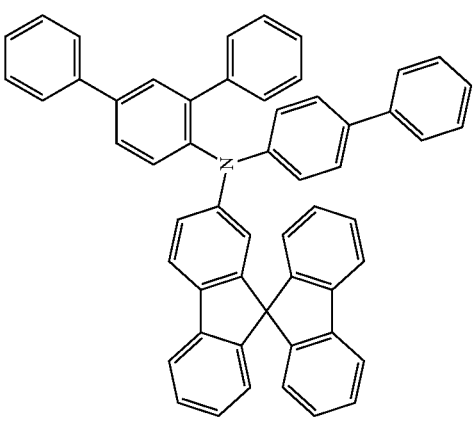 | 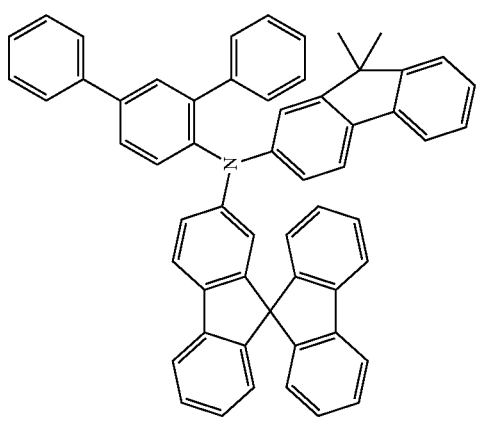 | 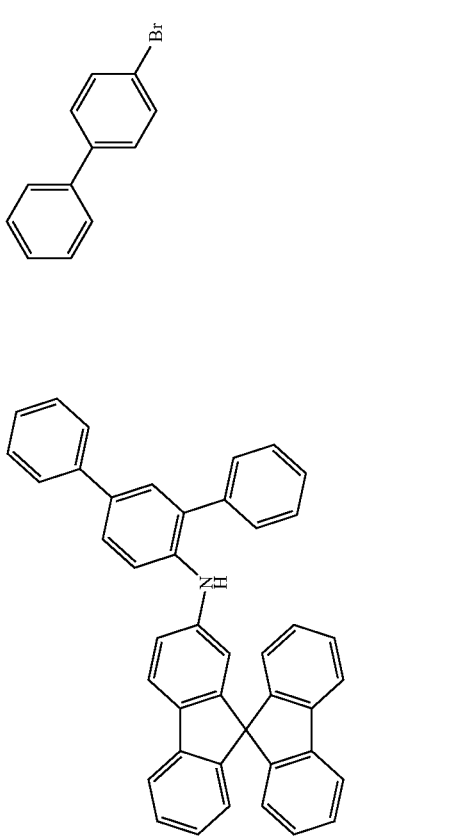 | 64% |
| B11 | 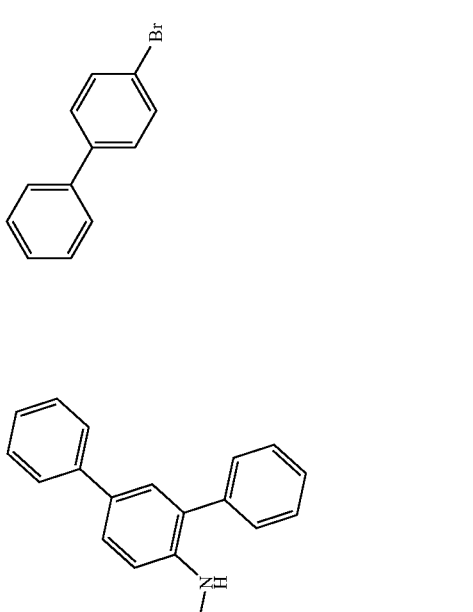 | 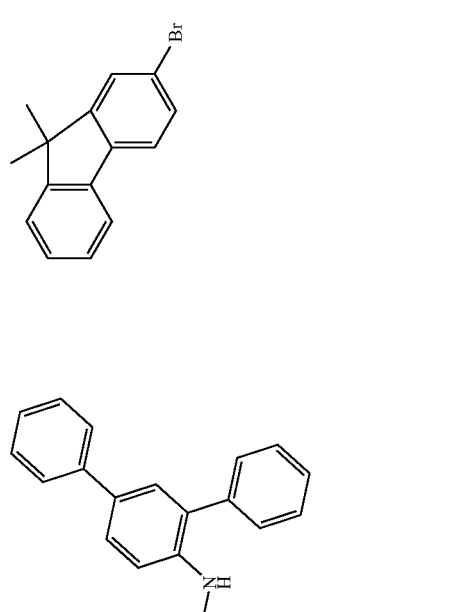 |  | 65% |

-continued

| Ex. | Starting material 1 | Starting material 2 | Product | Yield |
|---|---|---|---|---|
| B12 | | | | 89% |
| B13 | | | | 65% |

-continued

| Ex. | Starting material 1 | Starting material 2 | Product | Yield |
|---|---|---|---|---|
| B14 | | | | 69% |
| B15 | | | | 65% |

| Ex. | Starting material 1 | Starting material 2 | Product | Yield |
|---|---|---|---|---|
| B16 | | | | 77% |
| B17 comp. | | [474918-32-6] | | 77% |

| Ex. | Starting material 1 | Starting material 2 | Product | Yield |
|---|---|---|---|---|
| B18 | | | | 65% |
| B19 | | | | 65% |
| B20 | | | | 59% |

| Ex. | Starting material 1 | Starting material 2 | Product | Yield |
|---|---|---|---|---|
| B21 | phenoxazine [6267-02-3] | 2-bromo-9,9'-spirobifluorene | N-(9,9'-spirobifluoren-2-yl)phenoxazine | 61% |
| B22 | N-(biphenyl-4-yl)-9,9'-spirobifluoren-2-amine | 2-bromo-9,9-dimethylfluorene [1190360-23-6] | N-(biphenyl-4-yl)-N-(9,9-dimethylfluoren-2-yl)-9,9'-spirobifluoren-2-amine | 78% |

-continued

| Ex. | Starting material 1 | Starting material 2 | Product | Yield |
|---|---|---|---|---|
| B23 | N-(9,9-dimethylfluoren-2-yl)-9,9'-spirobifluoren-2-amine | 2-bromo-9,9-dimethylfluorene [1190360-23-6] | N,N-bis(9,9-dimethylfluoren-2-yl)-9,9'-spirobifluoren-2-amine | 77% |
| B24 | N-(9,9-dimethylfluoren-2-yl)-9,9'-spirobifluoren-2-amine | 1-bromo-9,9-dimethylfluorene [942615-32-9] | N-(9,9-dimethylfluoren-1-yl)-N-(9,9-dimethylfluoren-2-yl)-9,9'-spirobifluoren-2-amine | 64% |

-continued

| Ex. | Starting material 1 | Starting material 2 | Product | Yield |
|---|---|---|---|---|
| B25 | (9,9-dimethylfluoren-2-yl)(9,9'-spirobifluoren-2-yl)amine | 1-bromo-9,9-dimethylfluorene [1225053-54-2] | | 69% |
| B26 | (9,9-dimethylfluoren-2-yl)(9,9'-spirobifluoren-2-yl)amine | 2-bromodibenzothiophene [22439-61-8] | | 66% |

| Ex. | Starting material 1 | Starting material 2 | Product | Yield |
|---|---|---|---|---|
| B27 | 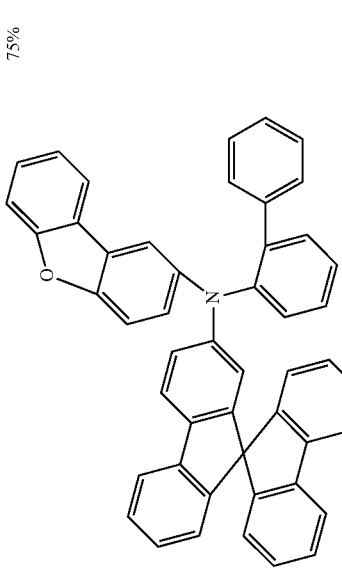 | 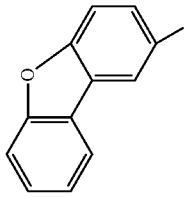  [86-76-0] | 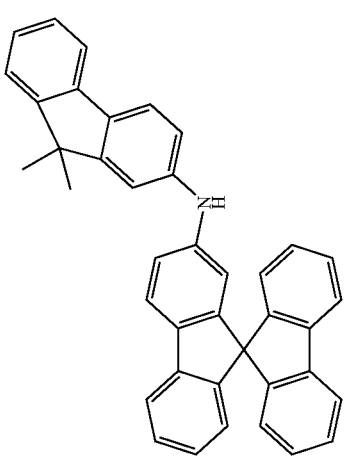 | 75% |

Example C

Synthesis of biphenyl-2-yl-(9,9-dimethyl-9H-fluoren-2-yl)-(9,9'-spirobifluoren-2-yl)amine

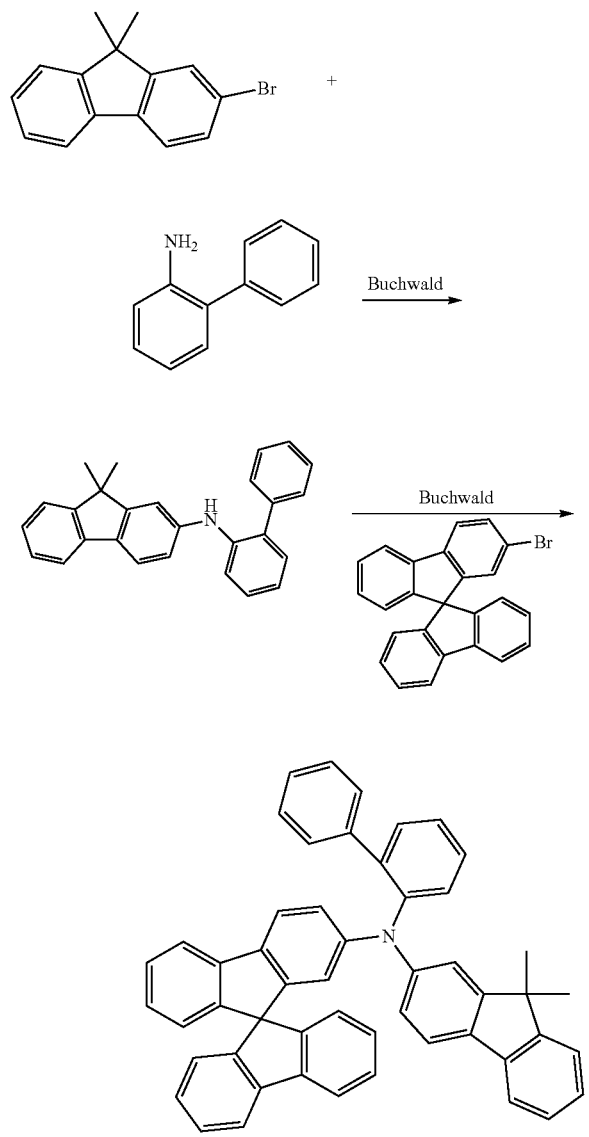

a) Biphenyl-2-yl-(9,9-dimethyl-9H-fluoren-2-yl)amine 1,1'-Bis(diphenylphosphino)ferrocene (1.5 g, 2.7 mmol), palladium acetate (616 mg, 2.7 mmol) and sodium tert-butoxide (22.9 g, 238 mmol) are added to a solution of biphenyl-2-ylamine (31.0 g, 183 mmol) and 2-bromo-9,9-dimethyl-9H-fluorene (50.0 g, 183 mmol) in degassed toluene (400 ml), and the mixture is heated under reflux for 20 h. The reaction mixture is cooled to room temperature, diluted with toluene and filtered through Celite. The filtrate is diluted with water and re-extracted with toluene, and the combined organic phases are dried and evaporated in vacuo. The residue is filtered through silica gel (heptane/dichloromethane) and crystallised from isopropanol, giving biphenyl-2-yl-(9,9-dimethyl-9H-fluoren-2-yl)amine in the form of a pale-yellow solid (63.0 g, 95% of theory).

b) Biphenyl-2-yl-(9,9-dimethyl-9H-fluoren-2-yl)-(9,9'-spirobifluoren-2-yl)amine Tri-tert-butylphosphine (4.4 ml of a 1.0 M solution in toluene, 4.4 mmol), palladium acetate (248 mg, 1.1 mmol) and sodium tert-butoxide (16.0 g, 166 mmol) are added to a solution of biphenyl-2-yl-(9,9-dimethyl-9H-fluoren-2-yl)amine (40.0 g, 111 mmol) and 2-bromo-9,9'-spirobifluorene (56.9 g, 144 mmol) in degassed toluene (500 ml), and the mixture is heated under reflux for 2 h. The reaction mixture is cooled to room temperature, diluted with toluene and filtered through Celite. The filtrate is evaporated in vacuo, and the residue is crystallised from ethyl acetate/heptane. The crude product is extracted in a Soxhlet extractor (toluene) and purified by zone sublimation in vacuo twice ($p=3\times10^{-4}$ mbar, T=298° C.). Biphenyl-2-yl-(9,9-dimethyl-9H-fluoren-2-yl)-(9,9'-spirobifluoren-2-yl)amine is isolated in the form of a pale-yellow solid (20.4 g, 27% of theory, purity >99.99% according to HPLC).

The following compounds can be obtained analogously:

| Ex. | Starting material 1 | Starting material 2 | Product | Yield |
|---|---|---|---|---|
| C1 | [1190360-23-6] | [90-41-5] | | 73% |

-continued
| Ex. | Starting material 1 | Starting material 2 | | Product | Yield |
|---|---|---|---|---|---|
| C2 | 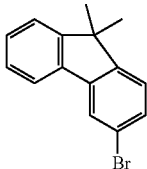 [SMILES: CC1(C)c2ccccc2-c2cc(Br)ccc21] [1190360-23-6] | 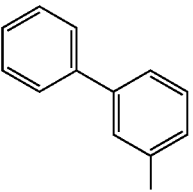 [2243-47-2] | 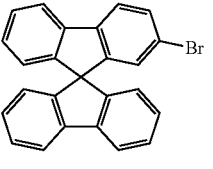 [SMILES: Brc1ccc2c(c1)C1(c3ccccc3-c3ccccc31)c1ccccc1-2] | 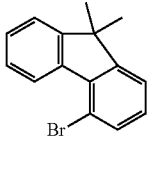 [SMILES: CC1(C)c2ccccc2-c2c(Br)cccc21] | 75% |
| C3 | 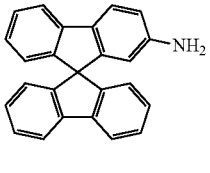 [SMILES: Nc1ccc2c(c1)C1(c3ccccc3-c3ccccc31)c1ccccc1-2] [942615-32-9] | 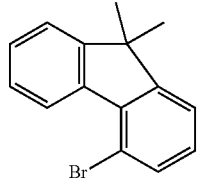 [SMILES: CC1(C)c2ccccc2-c2c(Br)cccc21] [118951-68-1] | 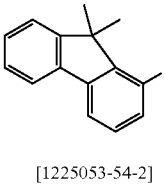 [942615-32-9] | 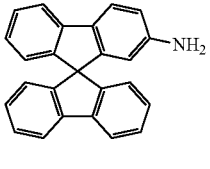 [SMILES: Nc1ccc2c(c1)C1(c3ccccc3-c3ccccc31)c1ccccc1-2] | 79% |
| C4 | 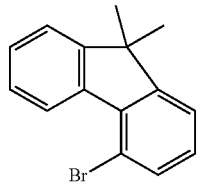 [SMILES: CC1(C)c2ccccc2-c2c(Br)cccc21] [1225053-54-2] | 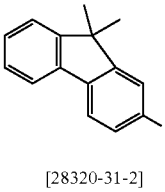 [118951-68-1] | 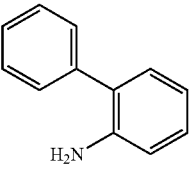 [SMILES: Nc1ccccc1-c1ccccc1] [942615-32-9] | 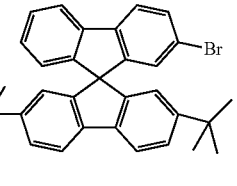 | 78% |
| C5 | 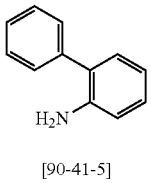 [28320-31-2] | 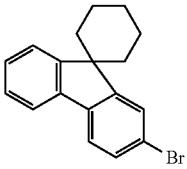 [SMILES: Brc1ccc2c(c1)C1(CCCCC1)c1ccccc1-2] [90-41-5] | 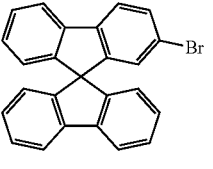 [393841-81-1] | | 65% |
| C6 | [90-41-5] | [797056-48-5] | | | 70% |

| Ex. | Starting material 1 | Starting material 2 | Product | Yield |
|---|---|---|---|---|
| C7 | 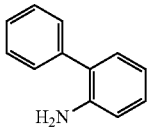 [90-41-5] | 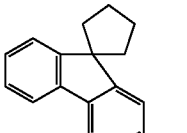 [797056-47-4] |  | 80% |

Example D 2-(9,9'-Spirobi(9H-fluorene))-9,9-dimethyl-10-phenyl-9,10-dihydroacridine

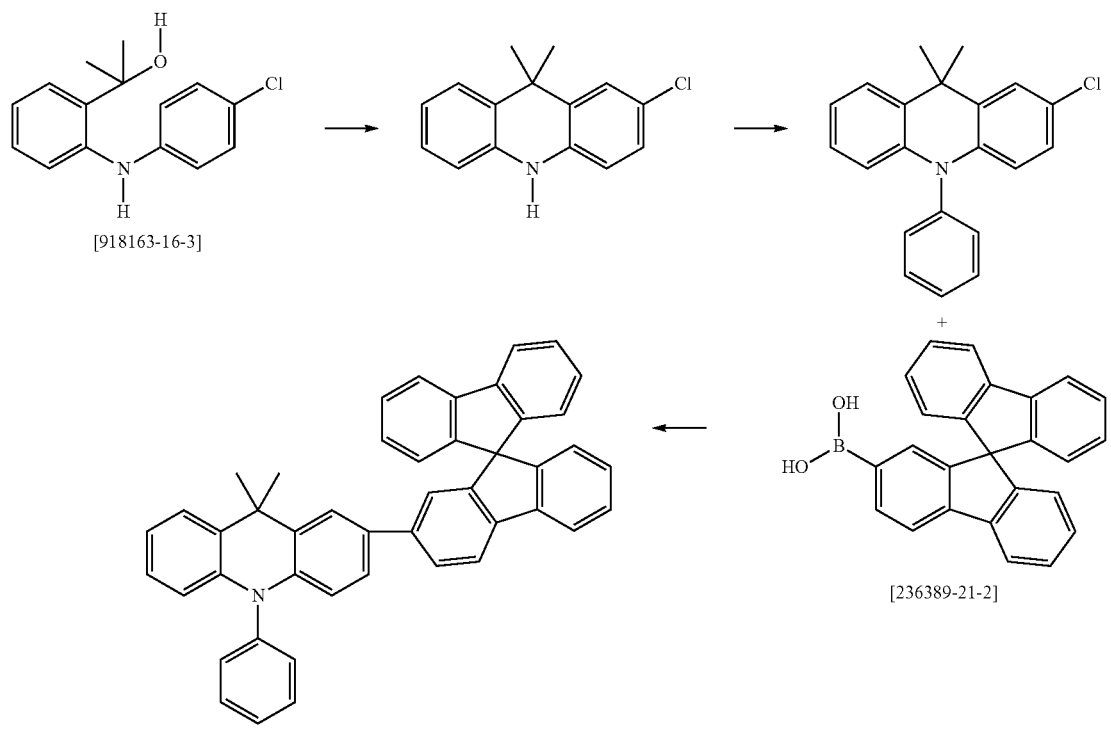

a) Synthesis of 2-chloro-9,9-dimethyl-9,10-dihydroacridine 30.3 g (116 mmol) of 2-[2-(4-chlorophenylamino)phenyl]propan-2-ol are dissolved in 700 ml of degassed toluene, a suspension of 93 g of polyphosphoric acid and 61.7 g of methanesulfonic acid is added, and the mixture is stirred at room temperature for 1 h and heated at 50° C. for 1 h. The batch is cooled, added to ice and extracted three times with ethyl acetate. The combined organic phases are washed with saturated sodium chloride solution, dried over magnesium sulfate and evaporated. Filtration of the crude product through silica gel with heptane/ethyl acetate (20:1) gives 25.1 g (89%) of 2-chloro-9,9-dimethyl-9,10-dihydroacridine as pale-yellow crystals.

b) Synthesis of 2-chloro-9,9-dimethyl-10-phenyl-9,10-dihydroacridine

A degassed solution of 16.6 ml (147 mmol) of 4-iodobenzene and 30 g (123 mmol) of 2-chloro-9,9-dimethyl-9,10-dihydroacridine in 600 ml of toluene is saturated with $N_2$ for 1 h. Then, firstly 2.09 ml (8.6 mmol) of P(tBu)$_3$, then 1.38 g (6.1 mmol) of palladium(II) acetate are added, and subsequently 17.7 g (185 mmol) of NaOtBu in the solid state are added to the solution. the reaction mixture is heated under reflux for 1 h. After the mixture has been cooled to room temperature, 500 ml of water are carefully added. The aqueous phase is washed with 3×50 ml of toluene and dried over MgSO$_4$, and the solvent is removed in vacuo. Filtration of the crude product through silica gel with heptane/ethyl acetate (20:1) gives 32.2 g (81%) of 2-chloro-9,9-dimethyl-10-phenyl-9,10-dihydroacridine as pale-yellow crystals.

c) Synthesis of 2-(9,9'-spirobi(9H-fluorene))-9,9-dimethyl-10-phenyl-9,10-dihydroacridine 39.6 g (110 mmol) of 9,9'-spirobi[9H-fluoren]-2-ylboronic acid, 35.2 g (110 mmol) of 2-chloro-9,9-dimethyl-10-phenyl-9,10-dihydroacridine and 9.7 g (92 mmol) of sodium carbonate are suspended in 350 ml of toluene, 350 ml of dioxane and 500 ml of water. 913 mg (3.0 mmol) of tri-o-tolylphosphine and 112 mg (0.5 mmol) of palladium(II) acetate are added to this suspension, and the reaction mixture is heated under reflux for 16 h. After cooling, the organic phase is separated off, filtered through silica gel, washed three times with 200 ml of water and subsequently evaporated to dryness. The residue is recrystallised from toluene and from CH$_2$Cl$_2$/isopropanol and finally sublimed in a high vacuum.

Yield: 52 g (100 mmol), 79% of theory, purity according to HPLC 99.9%.

Example E

Production of OLEDs

OLEDs according to the invention and OLEDs in accordance with the prior art are produced by a general process in accordance with WO 2004/058911, which is adapted to the circumstances described here (layer-thickness variation, materials).

The data for various OLEDs are presented in Examples C1-I68, So11-3 below (see Tables 1 and 2). Glass plates coated with structured ITO (indium tin oxide) in a thickness of 150 nm are coated with 20 nm of PEDOT (poly(3,4-ethylenedioxy-2,5-thiophene), applied by spin coating from water; purchased from H.C. Starck, Goslar, Germany) for improved processing. These coated glass plates form the substrates to which the OLEDs are applied. The OLEDs basically have the following layer structure: substrate/optional hole-injection layer (HIL)/hole-transport layer (HTL)/optional interlayer 1 (IL1)/optional interlayer 2 (IL2)/electron-blocking layer (EBL)/emission layer (EML)/optional hole-blocking layer (HBL)/electron-transport layer (ETL)/optional electron-injection layer (EIL) and finally a cathode. The cathode is formed by an aluminium layer with a thickness of 100 nm. The precise structure of the OLEDs is shown in Table 1. The materials required for the production of the OLEDs are shown in Table 3.

All materials are applied by thermal vapour deposition in a vacuum chamber. The emission layer here always consists of at least one matrix material (host material) and an emitting dopant (emitter), with which the matrix material or matrix materials is (are) mixed by co-evaporation in a certain proportion by volume. An expression such as Ket1:FTPh:TEG1 (60%:30%:10%) here means that material Ket1 is present in the layer in a proportion by volume of 60%, FTPh is present in the layer in a proportion of 30% and TEG1 is present in the layer in a proportion of 10%. Analogously, the electron-transport layer may also consist of a mixture of two materials.

The OLEDs are characterised by standard methods. For this purpose, the electroluminescence spectra, the current efficiency (measured in cd/A), the power efficiency (measured in lm/W) and the external quantum efficiency (EQE, measured in percent) as a function of the luminous density, calculated from current/voltage/luminous density characteristic lines (IUL characteristic lines), and the lifetime are determined. The electroluminescence spectra are determined at a luminous density of 1000 cd/m$^2$, and the CIE 1931 x and y colour coordinates are calculated therefrom. The expression U1000 in Table 2 denotes the voltage required for a luminous density of 1000 cd/m$^2$. CE1000 and PE1000 denote the current and power efficiency respectively achieved at 1000 cd/m$^2$. Finally, EQE1000 is the external quantum efficiency at an operating luminous density of 1000 cd/m$^2$. The lifetime LT is defined as the time after which the luminous density has dropped from the initial luminous density L0 to a certain proportion L1 on operation at constant current. The expressions L0=4000 cd/m$^2$ and L1=80% in Table 2 mean that the lifetime indicated in column LT corresponds to the time after which the initial luminous density of the corresponding OLED has dropped from 4000 cd/m$^2$ to 3200 cd/m$^2$. The values for the lifetime can be converted into a figure for other initial luminous densities with the aid of conversion formulae known to the person skilled in the art. The lifetime for an initial luminous density of 1000 cd/m$^2$ is the usual specification here.

The data for the various OLEDs are summarised in Table 2. Examples C1-C20 are comparative examples in accordance with the prior art, while Examples I1-I68 and So11-3 show data for OLEDs comprising materials according to the invention.

Some of the examples are explained in greater detail below in order to illustrate the advantages of the compounds according to the invention. However, it should be pointed out that this only represents a selection of the data shown in Table 2. As can be seen from the table, significant improvements over the prior art are also achieved on use of the compounds according to the invention that are not mentioned in greater detail, in some cases in all parameters, but in some cases only an improvement in efficiency or voltage or lifetime can be observed. However, even the improvement of one of the said parameters represents a significant advance since different applications require optimisation with respect to different parameters.

Use of Compounds According to the Invention as Hole-Transport Materials

OLEDs C1-C5 and C13-C20 are comparative examples which comprise hole-transport materials BPA1, NPB, CbzA1 and SpA-tb in accordance with the prior art. The materials according to the invention employed are compounds B1-B8, B10-B21, B23-B25, C, C1-C2, C4-C7 and D (Examples I1, I3, I6-I12, I15-I20, I22, I24-I31, I33-I68).

The use of materials according to the invention gives, in particular, significant improvements in the current efficiency and lifetime. The operating voltage remains approximately the same compared with the prior art, which, owing to the improved current efficiency, results in an improvement in the power efficiency. Thus, for example, the use of compound B11 in an OLED comprising the blue-fluorescent dopant D1 gives an increase in the power efficiency of about 35% compared with NPB (Examples I17, C1). The lifetime can be increased by almost 70% compared with NPB if compound C is used (Examples I30, C2).

In the case of the use of thicker layers, which can be employed, for example, for optimisation of the optical coupling-out efficiency and for improving the product yield, the materials according to the invention likewise exhibit advantages: whereas an increase in the layer thickness from 20 to 70 nm results in an increase in voltage of 0.6 V with compound SpA-tb, which contains a tert-butyl-substituted spirobifluorene, the voltage remains virtually unchanged in the case of the use of compound C (Examples C19, C20, I61, I62). Only a moderate increase in the voltage of 0.2 V is also obtained in the case of the use of compound C5, which contains only a substituted spirobifluorene. The same applies to compound B16, which contains two unsubstituted spirobifluorene units (Examples I63-I66).

Use of Compounds According to the Invention as Matrix Materials in Phosphorescent OLEDs The materials according to the invention can also be employed as a component in mixed-matrix systems. In a mixed matrix, a first matrix component is mixed with a second matrix component and a dopant, which offers, in particular, an improvement in the lifetime compared with the single-matrix materials. In this case, however, an increase in the operating voltage and a reduction in the efficiency compared with single-matrix materials frequently arise in accordance with the prior art. The use of the compounds according to the invention enables improvements to be achieved here.

Compared with CBP, an improvement in the voltage by 0.7 V, for example, is obtained through the use of B13 in combination with ST1, which is evident from a significant increase in the power efficiency by about 20% (Examples I23, C7). An improvement in the lifetime by about 50% arises through the replacement of CBP by compound B2 in a mixed matrix with Ket1 as the second component (Examples I5, C9). In combination with DAP1, the use of compound B9 likewise gives a significant improvement in the power efficiency (Examples I14, C12). This shows that the materials according to the invention can profitably be combined with very different classes of material in a mixed matrix.

In combination with the red dopant TER1, good performance data (Example C6) are already obtained with material TSpA1. If materials B1 and B18 in accordance with the prior art are used, a further improvement can be achieved (Examples I2, I32). In particular, material B1, which contains only one spiro unit, exhibits an improvement of about 30% in the lifetime and 20% in the power efficiency compared with TSpA1 (Examples I2, C6).

Use of Compounds According to the Invention as Solution-Processed HTM

Films with a thickness of 40 nm are produced on various substrates by spin coating from a formulation of 10 mg/ml of substance C in toluene. The sample is subsequently dried by heating at a temperature of 180° C. on a hotplate for 10 min. The sample is subsequently introduced into a vacuum evaporation unit, and an emission layer with a thickness of 30 nm consisting of M2:D4 (95%:5%) is applied by vapour deposition. An electron-transport layer having a thickness of 20 nm comprising ST2:LiQ (50%:50%) is subsequently applied by vapour deposition, and finally a cathode with a thickness of 100 nm comprising aluminium is applied by vapour deposition.

Example Sol1

The layer sequence described is applied to the following substrate: ITO with a thickness of 50 nm on glass, to which a PEDOT layer with a thickness of 20 nm has been applied. The PEDOT layer is applied by spin coating from water as described above.

Example Sol2

The layer sequence described is applied to the following substrate: ITO with a thickness of 50 nm on glass, to which an HAT-CN layer with a thickness of 20 nm has been applied. The HAT-CN layer is applied by evaporation in a vacuum unit.

Example Sol3

The production is carried out as in the case of Sol2, with the exception that ST2:LiQ is replaced by material ETM2 as electron-transport layer and an LiF layer with a thickness of 1.5 nm as electron-injection layer.

As revealed by Table 2, good to very good data are obtained with substance C processed from solution, in particular if the material is applied to an HAT-CN layer.

TABLE 1

Structure of the OLEDs

| Ex. | HIL thickness | HTL thickness | IL1 thickness | IL2 thickness | EBL thickness | EML thickness | HBL thickness | ETL thickness | EIL thickness |
|---|---|---|---|---|---|---|---|---|---|
| C1 | HATCN 5 nm | SpA1 140 nm | — | — | NPB 20 nm | M1:D1 (95%:5%) 30 nm | — | Alq3 20 nm | LiF 1 nm |
| C2 | HATCN 5 nm | SpA1 140 nm | — | — | NPB 20 nm | M1:D1 (95%:5%) 30 nm | — | ETM1:LiQ (50%:50%) 20 nm | — |
| C3 | HATCN 5 nm | SpA1 110 nm | — | — | NPB 20 nm | M2:D2 (90%:10%) 30 nm | — | Alq$_3$ 20 nm | LiF 1 nm |
| C4 | HATCN 5 nm | SpNPB 40 nm | — | — | NPB 20 nm | M2:D3 (98.5%:1.5%) 30 nm | — | ST2:LiQ (50%:50%) 20 nm | — |
| C5 | — | SpA1 70 nm | HATCN 5 nm | — | BPA1 90 nm | Ket1:TEG1 (90%:10%) 30 nm | — | ST1:LiQ (50%:50%) 40 nm | — |
| C6 | — | SpA1 20 nm | — | — | NPB 20 nm | Ket1:TSpA1:TER1 (65%:25%:10%) 30 nm | Ket1 10 nm | Alq$_3$ 20 nm | LiF 1 nm |
| C7 | — | SpA1 70 nm | HATCN 5 nm | — | BPA1 90 nm | ST1:CBP:TEG1 (30%:60%:10%) 30 nm | ST1 10 nm | ST1:LiQ (50%:50%) 30 nm | — |
| C8 | — | SpA1 70 nm | HATCN 5 nm | — | BPA1 90 nm | ST1:TCTA:TEG1 (30%:60%:10%) 30 nm | — | ST1:LiQ (50%:50%) 30 nm | — |

TABLE 1-continued

| | | | | | Structure of the OLEDs | | | | |
|---|---|---|---|---|---|---|---|---|---|
| Ex. | HIL thickness | HTL thickness | IL1 thickness | IL2 thickness | EBL thickness | EML thickness | HBL thickness | ETL thickness | EIL thickness |
| C9 | HATCN 20 nm | — | — | — | BPA1 20 nm | Ket1:FTPh:TEG1 (60%:30%:10%) 30 nm | Ket1 10 nm | ETM2 20 nm | LiF 1 nm |
| C10 | HATCN 20 nm | — | — | — | BPA1 20 nm | Ket1:TCTA:TEG1 (60%:30%:10%) 30 nm | Ket1 10 nm | ETM2 20 nm | LiF 1 nm |
| C11 | HATCN 20 nm | — | — | — | BPA1 20 nm | Ket1:CBP:TEG1 (60%:30%:10%) 30 nm | Ket1 10 nm | ETM2 20 nm | LiF 1 nm |
| C12 | — | SpA1 70 nm | HATCN 5 nm | — | BPA1 90 nm | DAP1:CBP:TEG1 (30%:60%:10%) 30 nm | — | ST1:LiQ (50%:50%) 30 nm | — |
| C13 | — | SpA1 70 nm | HATCN 5 nm | — | BPA1 90 nm | IC1:TEG1 (90%:10%) 30 nm | ST1 10 nm | ST1:LiQ (50%:50%) 30 nm | — |
| C14 | HATCN 5 nm | SpA1 140 nm | HATCN 5 nm | — | BPA1 20 nm | M2:D4 (95%:5%) 20 nm | — | ST1:LiQ (50%:50%) 30 nm | LiQ 1 nm |
| C15 | HATCN 5 nm | SpA1 140 nm | HATCN 5 nm | — | NPB 20 nm | M2:D4 (95%:5%) 20 nm | — | ST1:LiQ (50%:50%) 30 nm | LiQ 1 nm |
| C16 | HATCN 5 nm | TIFA1 140 nm | HATCN 5 nm | — | CbzA1 20 nm | M2:D4 (95%:5%) 20 nm | — | ST2:LiQ (50%:50%) 30 nm | LiQ 1 nm |
| C17 | HATCN 5 nm | SpA1 140 nm | HATCN 5 nm | — | CbzA1 20 nm | IC1:TEG1 (90%:10%) 30 nm | — | ST2:LiQ (50%:50%) 40 nm | LiQ 1 nm |
| C18 | HATCN 5 nm | SpA1 140 nm | HATCN 5 nm | CbzA1 10 nm | CbzA1 20 nm | M2:D4 (95%:5%) 20 nm | — | ST2:LiQ (50%:50%) 30 nm | LiQ 1 nm |
| C19 | HATCN 5 nm | SpA1 130 nm | HATCN 5 nm | — | SpA-tb 20 nm | IC1:TEG1 (90%:10%) 30 nm | — | ST2:LiQ (50%:50%) 40 nm | LiQ 1 nm |
| C20 | HATCN 5 nm | SpA1 80 nm | HATCN 5 nm | — | SpA-tb 70 nm | IC1:TEG1 (90%:10%) 30 nm | — | ST2:LiQ (50%:50%) 40 nm | LiQ 1 nm |
| I1 | — | SpA1 70 nm | HATCN 5 nm | — | B1 90 nm | IC1:TEG1 (90%:10%) 30 nm | ST1 10 nm | ST1:LiQ (50%:50%) 30 nm | — |
| I2 | — | SpA1 20 nm | — | — | NPB 20 nm | Ket1:B1:TER1 (65%:25%:10%) 30 nm | Ket1 10 nm | Alq$_3$ 20 nm | LiF 1 nm |
| I3 | HATCN 5 nm | SpNPB 40 nm | — | — | B2 20 nm | M2:D3 (98.5%:1.5%) 30 nm | — | ST2:LiQ (50%:50%) 30 nm | — |
| I4 | — | SpA1 70 nm | HATCN 5 nm | — | BPA1 90 nm | ST1:B2:TEG1 (30%:60%:10%) 30 nm | ST1 10 nm | ST1:LiQ (50%:50%) 30 nm | — |
| I5 | HATCN 20 nm | — | — | — | BPA1 20 nm | Ket1:B2:TEG1 (60%:30%:10%) 30 nm | Ket1 10 nm | ETM2 20 nm | LiF 1 nm |
| I6 | HATCN 5 nm | SpA1 140 nm | — | — | B3 20 nm | M1:D1 (95%:5%) 30 nm | — | ETM1:LiQ (50%:50%) 20 nm | — |
| I7 | HATCN 5 nm | SpA1 110 nm | — | — | B4 20 nm | M2:D2 (90%:10%) 30 nm | — | Alq$_3$ 20 nm | LiF 1 nm |
| I8 | HATCN 5 nm | SpA1 110 nm | — | — | B5 20 nm | M2:D2 (90%:10%) 30 nm | — | Alq$_3$ 20 nm | LiF 1 nm |
| I9 | HATCN 5 nm | SpA1 110 nm | — | — | B6 20 nm | M2:D2 (90%:10%) 30 nm | — | Alq$_3$ 20 nm | LiF 1 nm |
| I10 | HATCN 5 nm | SpA1 110 nm | — | — | B7 20 nm | M2:D2 (90%:10%) 30 nm | — | Alq$_3$ 20 nm | LiF 1 nm |
| I11 | HATCN 5 nm | SpA1 140 nm | — | — | B8 20 nm | M1:D1 (95%:5%) 30 nm | — | ETM1:LiQ (50%:50%) 20 nm | — |
| I12 | — | SpA1 70 nm | HATCN 5 nm | — | B8 90 nm | IC1:TEG1 (90%:10%) 30 nm | ST1 10 nm | ST1:LiQ (50%:50%) 30 nm | — |

TABLE 1-continued

Structure of the OLEDs

| Ex. | HIL thickness | HTL thickness | IL1 thickness | IL2 thickness | EBL thickness | EML thickness | HBL thickness | ETL thickness | EIL thickness |
|---|---|---|---|---|---|---|---|---|---|
| I13 | — | SpA1 70 nm | HATCN 5 nm | — | BPA1 90 nm | ST1:B9:TEG1 (30%:60%:10%) 30 nm | ST1 10 nm | ST1:LiQ (50%:50%) 30 nm | — |
| I14 | — | SpA1 70 nm | HATCN 5 nm | — | BPA1 90 nm | DAP1:B9:TEG1 (30%:60%:10%) 30 nm | — | ST1:LiQ (50%:50%) 30 nm | — |
| I15 | HATCN 5 nm | SpA1 140 nm | — | — | B10 20 nm | M1:D1 (95%:5%) 30 nm | — | ETM1:LiQ (50%:50%) 20 nm | — |
| I16 | — | SpA1 70 nm | HATCN 5 nm | — | B10 90 nm | Ket1:TEG1 (90%:10%) 30 nm | — | ST1:LiQ (50%:50%) 40 nm | — |
| I17 | HATCN 5 nm | SpA1 140 nm | — | — | B11 20 nm | M1:D1 (95%:5%) 30 nm | — | Alq3 20 nm | LiF 1 nm |
| I18 | HATCN 5 nm | SpA1 110 nm | — | — | B11 20 nm | M2:D2 (90%:10%) 30 nm | — | Alq$_3$ 20 nm | LiF 1 nm |
| I19 | — | SpA1 70 nm | HATCN 5 nm | — | B11 90 nm | IC1:TEG1 (90%:10%) 30 nm | ST1 10 nm | ST1:LiQ (50%:50%) 30 nm | — |
| I20 | HATCN 5 nm | SpNPB 40 nm | — | — | B12 20 nm | M2:D3 (98.5%:1.5%) 30 nm | — | ST2:LiQ (50%:50%) 20 nm | — |
| I21 | — | SpA1 70 nm | HATCN 5 nm | — | BPA1 90 nm | ST1:B12:TEG1 (30%:60%:10%) 30 nm | ST1 10 nm | ST1:LiQ (50%:50%) 30 nm | — |
| I22 | HATCN 5 nm | SpNPB 40 nm | — | — | B13 20 nm | M2:D3 (98.5%:1.5%) 30 nm | — | ST2:LiQ (50%:50%) 20 nm | — |
| I23 | — | SpA1 70 nm | HATCN 5 nm | — | BPA1 90 nm | ST1:B13:TEG1 (30%:60%:10%) 30 nm | ST1 10 nm | ST1:LiQ (50%:50%) 30 nm | — |
| I24 | HATCN 5 nm | SpA1 140 nm | — | — | B14 20 nm | M1:D1 (95%:5%) 30 nm | — | Alq3 20 nm | LiF 1 nm |
| I25 | HATCN 5 nm | SpA1 110 nm | — | — | B14 20 nm | M2:D2 (90%:10%) 30 nm | — | Alq$_3$ 20 nm | LiF 1 nm |
| I26 | HATCN 5 nm | SpA1 140 nm | — | — | B15 20 nm | M1:D1 (95%:5%) 30 nm | — | Alq3 20 nm | LiF 1 nm |
| I27 | HATCN 5 nm | SpA1 140 nm | — | — | B15 20 nm | M1:D1 (95%:5%) 30 nm | — | ETM1:LiQ (50%:50%) 20 nm | — |
| I28 | HATCN 5 nm | SpA1 140 nm | — | — | B16 20 nm | M1:D1 (95%:5%) 30 nm | — | ETM1:LiQ (50%:50%) 20 nm | — |
| I29 | HATCN 5 nm | SpA1 140 nm | — | — | B17 20 nm | M1:D1 (95%:5%) 30 nm | — | ETM1:LiQ (50%:50%) 20 nm | — |
| I30 | HATCN 5 nm | SpA1 140 nm | — | — | B18 20 nm | M1:D1 (95%:5%) 30 nm | — | ETM1:LiQ (50%:50%) 20 nm | — |
| I31 | HATCN 5 nm | SpNPB 40 nm | — | — | B18 20 nm | M2:D3 (98.5%:1.5%) 30 nm | — | ST2:LiQ (50%:50%) 20 nm | — |
| I32 | — | SpA1 20 nm | — | — | NPB 20 nm | Ket1:B18:TER1 (65%:25%:10%) 30 nm | Ket1 10 nm | Alq3 20 nm | LiF 1 nm |
| I33 | — | SpA1 70 nm | HATCN 5 nm | — | B19 90 nm | IC1:TEG1 (90%:10%) 30 nm | ST1 10 nm | ST1:LiQ (50%:50%) 30 nm | — |
| I34 | — | SpA1 70 nm | HATCN 5 nm | — | B20 90 nm | IC1:TEG1 (90%:10%) 30 nm | ST1 10 nm | ST1:LiQ (50%:50%) 30 nm | — |
| I35 | — | SpA1 70 nm | HATCN 5 nm | — | B21 90 nm | IC1:TEG1 (90%:10%) 30 nm | ST1 10 nm | ST1:LiQ (50%:50%) 30 nm | — |
| I36 | HATCN 5 nm | SpA1 140 nm | — | — | C 20 nm | M1:D1 (95%:5%) 30 nm | — | Alq3 20 nm | LiF 1 nm |

TABLE 1-continued

Structure of the OLEDs

| Ex. | HIL thickness | HTL thickness | IL1 thickness | IL2 thickness | EBL thickness | EML thickness | HBL thickness | ETL thickness | EIL thickness |
|---|---|---|---|---|---|---|---|---|---|
| I37 | HATCN 5 nm | SpA1 140 nm | — | — | C 20 nm | M1:D1 (95%:5%) 30 nm | — | ETM1:LiQ (50%:50%) 20 nm | — |
| I38 | HATCN 5 nm | SpA1 110 nm | — | — | C 20 nm | M2:D2 (90%:10%) 30 nm | — | Alq$_3$ 20 nm | LiF 1 nm |
| I39 | — | SpA1 70 nm | HATCN 5 nm | — | C 90 nm | IC1:TEG1 (90%:10%) 30 nm | ST1 10 nm | ST1:LiQ (50%:50%) 30 nm | — |
| I40 | HATCN 5 nm | SpA1 140 nm | HATCN 5 nm | — | C 20 nm | M2:D4 (95%:5%) 20 nm | — | ST2:LiQ (50%:50%) 30 nm | LiQ 1 nm |
| I41 | HATCN 5 nm | SpA1 140 nm | HATCN 5 nm | — | C 20 nm | M2:D4 (95%:5%) 20 nm | — | ST1:LiQ (50%:50%) 30 nm | LiQ 1 nm |
| I42 | HATCN 5 nm | TIFA1 140 nm | HATCN 5 nm | — | B1 20 nm | M2:D4 (95%:5%) 20 nm | — | ST2:LiQ (50%:50%) 30 nm | LiQ 1 nm |
| I43 | HATCN 5 nm | TIFA1 140 nm | HATCN 5 nm | — | C 20 nm | M2:D4 (95%:5%) 20 nm | — | ST2:LiQ (50%:50%) 30 nm | LiQ 1 nm |
| I44 | HATCN 5 nm | SpA1 125 nm | HATCN 5 nm | C 10 nm | B18 20 nm | M2:D4 (95%:5%) 20 nm | — | ST2:LiQ (50%:50%) 30 nm | LiQ 1 nm |
| I45 | HATCN 5 nm | SpA1 125 nm | HATCN 5 nm | C 10 nm | D 20 nm | M2:D4 (95%:5%) 20 nm | — | ST2:LiQ (50%:50%) 30 nm | LiQ 1 nm |
| I46 | HATCN 5 nm | SpA1 125 nm | HATCN 5 nm | C 10 nm | B19 20 nm | M2:D4 (95%:5%) 20 nm | — | ST2:LiQ (50%:50%) 30 nm | LiQ 1 nm |
| I47 | HATCN 5 nm | SpA1 140 nm | HATCN 5 nm | — | C5 20 nm | M2:D4 (95%:5%) 20 nm | — | ST2:LiQ (50%:50%) 30 nm | LiQ 1 nm |
| I48 | HATCN 5 nm | SpA1 140 nm | HATCN 5 nm | CbzA1 10 nm | C6 20 nm | M2:D4 (95%:5%) 20 nm | — | ST2:LiQ (50%:50%) 30 nm | LiQ 1 nm |
| I49 | HATCN 5 nm | SpA1 140 nm | HATCN 5 nm | — | C6 20 nm | IC1:TEG1 (90%:10%) 30 nm | — | ST2:LiQ (50%:50%) 40 nm | LiQ 1 nm |
| I50 | HATCN 5 nm | SpA1 140 nm | HATCN 5 nm | — | C7 20 nm | IC1:TEG1 (90%:10%) 30 nm | — | ST2:LiQ (50%:50%) 40 nm | LiQ 1 nm |
| I51 | HATCN 5 nm | SpA1 140 nm | HATCN 5 nm | — | B22 20 nm | IC1:TEG1 (90%:10%) 30 nm | — | ST2:LiQ (50%:50%) 40 nm | LiQ 1 nm |
| I52 | HATCN 5 nm | TIFA1 140 nm | HATCN 5 nm | — | C1 20 nm | M2:D4 (95%:5%) 20 nm | — | ST2:LiQ (50%:50%) 30 nm | LiQ 1 nm |
| I53 | HATCN 5 nm | SpA1 140 nm | HATCN 5 nm | — | B23 20 nm | IC1:TEG1 (90%:10%) 30 nm | — | ST2:LiQ (50%:50%) 40 nm | LiQ 1 nm |
| I54 | — | SpA1 70 nm | HATCN 5 nm | — | B24 90 nm | IC1:TEG1 (90%:10%) 30 nm | ST1 10 nm | ST1:LiQ (50%:50%) 30 nm | — |
| I55 | HATCN 5 nm | SpA1 140 nm | HATCN 5 nm | — | B24 20 nm | M2:D4 (95%:5%) 20 nm | — | ST2:LiQ (50%:50%) 30 nm | LiQ 1 nm |
| I56 | HATCN 5 nm | SpA1 140 nm | HATCN 5 nm | — | B25 20 nm | M2:D4 (95%:5%) 20 nm | — | ST2:LiQ (50%:50%) 30 nm | LiQ 1 nm |
| I57 | — | SpA1 70 nm | HATCN 5 nm | — | C2 90 nm | IC1:TEG1 (90%:10%) 30 nm | ST1 10 nm | ST1:LiQ (50%:50%) 30 nm | — |
| I58 | — | SpA1 70 nm | HATCN 5 nm | — | C4 90 nm | IC1:TEG1 (90%:10%) 30 nm | ST1 10 nm | ST1:LiQ (50%:50%) 30 nm | — |
| I59 | HATCN 5 nm | SpA1 140 nm | HATCN 5 nm | CbzA1 10 nm | B26 20 nm | M2:D4 (95%:5%) 20 nm | — | ST2:LiQ (50%:50%) 30 nm | LiQ 1 nm |
| I60 | HATCN 5 nm | SpA1 140 nm | HATCN 5 nm | CbzA1 10 nm | B27 20 nm | M2:D4 (95%:5%) 20 nm | — | ST2:LiQ (50%:50%) 30 nm | LiQ 1 nm |

TABLE 1-continued

Structure of the OLEDs

| Ex. | HIL thickness | HTL thickness | IL1 thickness | IL2 thickness | EBL thickness | EML thickness | HBL thickness | ETL thickness | EIL thickness |
|---|---|---|---|---|---|---|---|---|---|
| I61 | HATCN 5 nm | SpA1 130 nm | HATCN 5 nm | — | C 20 nm | IC1:TEG1 (90%:10%) 30 nm | — | ST2:LiQ (50%:50%) 40 nm | LiQ 1 nm |
| I62 | HATCN 5 nm | SpA1 80 nm | HATCN 5 nm | — | C 70 nm | IC1:TEG1 (90%:10%) 30 nm | — | ST2:LiQ (50%:50%) 40 nm | LiQ 1 nm |
| I63 | HATCN 5 nm | SpA1 130 nm | HATCN 5 nm | — | C5 20 nm | IC1:TEG1 (90%:10%) 30 nm | — | ST2:LiQ (50%:50%) 40 nm | LiQ 1 nm |
| I64 | HATCN 5 nm | SpA1 80 nm | HATCN 5 nm | — | C5 70 nm | IC1:TEG1 (90%:10%) 30 nm | — | ST2:LiQ (50%:50%) 40 nm | LiQ 1 nm |
| I65 | HATCN 5 nm | SpA1 130 nm | HATCN 5 nm | — | B16 20 nm | IC1:TEG1 (90%:10%) 30 nm | — | ST2:LiQ (50%:50%) 40 nm | LiQ 1 nm |
| I66 | HATCN 5 nm | SpA1 80 nm | HATCN 5 nm | — | B16 70 nm | IC1:TEG1 (90%:10%) 30 nm | — | ST2:LiQ (50%:50%) 40 nm | LiQ 1 nm |
| I67 | HATCN 5 nm | SpA1 140 nm | HATCN 5 nm | — | B18 20 nm | M2:D4 (95%:5%) 20 nm | — | ST2:LiQ (50%:50%) 30 nm | LiQ 1 nm |
| I68 | — | B6 70 nm | HATCN 5 nm | — | BPA1 90 nm | IC1:TEG1 (90%:10%) 30 nm | ST1 10 nm | ST1:LiQ (50%:50%) 30 nm | — |

TABLE 2

Data for the OLEDs

| Ex. | U1000 (V) | CE1000 (cd/A) | PE1000 (lm/W) | EQE 1000 | CIE x/y at 1000 cd/m² | L0 (cd/m²) | L1 % | Lifetime (h) |
|---|---|---|---|---|---|---|---|---|
| C1 | 6.4 | 5.1 | 2.5 | 4.2% | 0.14/0.15 | 6000 | 50 | 150 |
| C2 | 4.7 | 8.1 | 5.4 | 6.3% | 0.14/0.16 | 6000 | 50 | 145 |
| C3 | 5.0 | 17 | 11 | 5.0% | 0.28/0.61 | 25000 | 50 | 480 |
| C4 | 4.3 | 9.8 | 7.1 | 7.6% | 0.141/0.160 | 6000 | 50 | 210 |
| C5 | 3.9 | 41 | 33 | 11.0% | 0.36/0.61 | 4000 | 80 | 315 |
| C6 | 4.3 | 7.7 | 5.6 | 10.8% | 0.68/0.32 | 4000 | 80 | 360 |
| C7 | 4.4 | 48 | 34 | 13.3% | 0.37/0.60 | 4000 | 80 | 450 |
| C8 | 4.2 | 43 | 32 | 12.0% | 0.35/0.60 | 4000 | 80 | 195 |
| C9 | 4.0 | 46 | 36 | 12.8% | 0.36/0.61 | 4000 | 80 | 370 |
| C10 | 3.9 | 42 | 34 | 11.6% | 0.35/0.60 | 4000 | 80 | 175 |
| C11 | 4.1 | 44 | 34 | 12.3% | 0.36/0.61 | 4000 | 80 | 280 |
| C12 | 4.6 | 47 | 32 | 13.2% | 0.36/0.60 | 4000 | 80 | 490 |
| C13 | 3.5 | 53 | 48 | 14.8% | 0.36/0.60 | 4000 | 80 | 430 |
| C14 | 4.2 | 7.0 | 9.5 | 7.4% | 0.14/0.16 | 6000 | 50 | 250 |
| C15 | 4.2 | 8.2 | 6.3 | 6.5% | 0.14/0.16 | 6000 | 50 | 315 |
| C16 | 4.4 | 7.6 | 5.4 | 5.4% | 0.14/0.18 | 6000 | 65 | 240 |
| C17 | 3.5 | 59 | 53 | 16.4% | 0.37/0.60 | 10000 | 70 | 235 |
| C18 | 4.3 | 8.4 | 6.1 | 6.5% | 0.14/0.16 | 6000 | 50 | 320 |
| C19 | 3.5 | 59 | 53 | 16.3% | 0.37/0.60 | 10000 | 65 | 310 |
| C20 | 4.1 | 57 | 43 | 15.9% | 0.37/0.60 | 10000 | 65 | 210 |
| I1 | 3.7 | 59 | 50 | 16.4% | 0.36/0.60 | 4000 | 80 | 490 |
| I2 | 4.2 | 9.0 | 6.7 | 12.8% | 0.68/0.32 | 4000 | 80 | 460 |
| I3 | 4.4 | 10.4 | 7.4 | 8.1% | 0.14/0.16 | 6000 | 50 | 260 |
| I4 | 4.0 | 51 | 40 | 14.2% | 0.37/0.61 | 4000 | 80 | 620 |
| I5 | 3.7 | 50 | 43 | 14.0% | 0.37/0.61 | 4000 | 80 | 550 |
| I6 | 4.6 | 9.1 | 6.3 | 7.1% | 0.14/0.16 | 6000 | 50 | 130 |
| I7 | 5.1 | 19 | 12 | 5.4% | 0.28/0.61 | 25000 | 50 | 460 |
| I8 | 5.1 | 18 | 11 | 5.2% | 0.28/0.61 | 25000 | 50 | 520 |
| I9 | 4.8 | 20 | 13 | 5.8% | 0.28/0.61 | 25000 | 50 | 530 |
| I10 | 5.0 | 18 | 11 | 5.3% | 0.28/0.61 | 25000 | 50 | 430 |
| I11 | 4.7 | 8.7 | 5.8 | 6.8% | 0.14/0.15 | 6000 | 50 | 160 |
| I12 | 3.4 | 58 | 54 | 16.1% | 0.36/0.60 | 4000 | 80 | 420 |
| I13 | 4.1 | 50 | 38 | 13.9% | 0.37/0.61 | 4000 | 80 | 470 |
| I14 | 3.9 | 52 | 41 | 14.4% | 0.37/0.61 | 4000 | 80 | 460 |
| I15 | 4.8 | 9.2 | 6.1 | 7.2% | 0.14/0.15 | 6000 | 50 | 230 |
| I16 | 4.0 | 46 | 36 | 12.8% | 0.37/0.60 | 4000 | 80 | 470 |
| I17 | 6.1 | 6.7 | 3.4 | 5.5% | 0.14/0.15 | 6000 | 50 | 230 |
| I18 | 5.2 | 20 | 12 | 5.7% | 0.28/0.61 | 25000 | 50 | 620 |
| I19 | 3.5 | 56 | 50 | 15.6% | 0.36/0.60 | 4000 | 80 | 550 |

TABLE 2-continued

Data for the OLEDs

| Ex. | U1000 (V) | CE1000 (cd/A) | PE1000 (lm/W) | EQE 1000 | CIE x/y at 1000 cd/m$^2$ | L0 (cd/m$^2$) | L1 % | Lifetime (h) |
|---|---|---|---|---|---|---|---|---|
| I20 | 4.5 | 11 | 7.6 | 8.4% | 0.14/0.16 | 6000 | 50 | 290 |
| I21 | 3.8 | 47 | 40 | 13.1% | 0.36/0.62 | 4000 | 80 | 440 |
| I22 | 4.5 | 11 | 7.3 | 8.2% | 0.14/0.16 | 6000 | 50 | 270 |
| I23 | 3.7 | 49 | 41 | 13.6% | 0.36/0.62 | 4000 | 80 | 470 |
| I24 | 6.2 | 6.2 | 3.1 | 5.1% | 0.14/0.15 | 6000 | 50 | 175 |
| I25 | 5.0 | 19 | 12 | 5.7% | 0.28/0.61 | 25000 | 50 | 510 |
| I26 | 6.3 | 6.4 | 3.2 | 5.3% | 0.14/0.15 | 6000 | 50 | 190 |
| I27 | 4.8 | 9.5 | 6.2 | 7.4% | 0.14/0.15 | 6000 | 50 | 175 |
| I28 | 4.5 | 8.7 | 6.1 | 6.8% | 0.14/0.15 | 6000 | 50 | 180 |
| I29 | 4.6 | 7.9 | 5.4 | 6.2% | 0.14/0.16 | 6000 | 50 | 165 |
| I30 | 4.8 | 9.5 | 6.3 | 7.4% | 0.14/0.16 | 6000 | 50 | 245 |
| I31 | 4.4 | 11 | 7.5 | 8.2% | 0.14/0.160 | 6000 | 50 | 280 |
| I32 | 4.4 | 8.2 | 5.9 | 11.6% | 0.68/0.32 | 4000 | 80 | 420 |
| I33 | 3.6 | 57 | 50 | 15.9% | 0.36/0.60 | 4000 | 80 | 410 |
| I34 | 3.8 | 58 | 49 | 16.1% | 0.36/0.60 | 4000 | 80 | 380 |
| I35 | 3.4 | 59 | 54 | 16.4% | 0.37/0.60 | 4000 | 80 | 360 |
| I36 | 6.2 | 6.6 | 3.3 | 5.4% | 0.14/0.15 | 6000 | 50 | 215 |
| I37 | 4.7 | 9.5 | 6.3 | 7.4% | 0.14/0.16 | 6000 | 50 | 240 |
| I38 | 5.2 | 19 | 12 | 5.7% | 0.28/0.61 | 25000 | 50 | 610 |
| I39 | 3.6 | 57 | 50 | 15.8% | 0.36/0.60 | 4000 | 80 | 530 |
| I40 | 4.2 | 10 | 7.4 | 7.7% | 0.14/0.16 | 6000 | 50 | 390 |
| I41 | 3.9 | 10.3 | 8.3 | 8.3% | 0.14/0.16 | 6000 | 50 | 360 |
| I42 | 4.5 | 8.3 | 5.7 | 5.9% | 0.14/0.18 | 6000 | 65 | 280 |
| I43 | 4.3 | 9.0 | 6.6 | 6.4% | 0.14/0.18 | 6000 | 65 | 295 |
| I44 | 4.3 | 9.0 | 6.3 | 7.3% | 0.14/0.15 | 6000 | 65 | 185 |
| I45 | 4.5 | 9.5 | 6.7 | 7.5% | 0.14/0.16 | 6000 | 65 | 190 |
| I46 | 4.7 | 10.5 | 6.9 | 8.5% | 0.14/0.16 | 6000 | 65 | 165 |
| I47 | 4.2 | 9.7 | 7.2 | 7.5% | 0.14/0.16 | 6000 | 50 | 395 |
| I48 | 4.3 | 10.1 | 7.7 | 8.4% | 0.14/0.16 | 6000 | 50 | 300 |
| I49 | 3.3 | 62 | 58 | 17.1% | 0.37/0.60 | 10000 | 70 | 230 |
| I50 | 3.4 | 61 | 57 | 17.3% | 0.37/0.60 | 10000 | 70 | 240 |
| I51 | 3.5 | 64 | 58 | 17.7% | 0.37/0.60 | 10000 | 70 | 225 |
| I52 | 4.2 | 9.9 | 7.4 | 7.8% | 0.14/0.16 | 6000 | 50 | 340 |
| I53 | 3.6 | 60 | 53 | 16.5% | 0.37/0.60 | 10000 | 70 | 215 |
| I54 | 3.5 | 56 | 49 | 15.4% | 0.36/0.60 | 4000 | 80 | 495 |
| I55 | 4.3 | 8.7 | 6.5 | 6.8% | 0.14/0.16 | 6000 | 50 | 350 |
| I56 | 4.2 | 9.5 | 7.0 | 7.3% | 0.14/0.16 | 6000 | 50 | 355 |
| I57 | 3.5 | 56 | 50 | 15.4% | 0.36/0.60 | 4000 | 80 | 460 |
| I58 | 3.6 | 59 | 52 | 16.3% | 0.36/0.60 | 4000 | 80 | 490 |
| I59 | 4.2 | 9.9 | 7.4 | 7.7% | 0.14/0.60 | 6000 | 50 | 240 |
| I60 | 4.2 | 9.5 | 7.1 | 7.4% | 0.14/0.60 | 6000 | 50 | 290 |
| I61 | 3.4 | 61 | 56 | 16.8% | 0.37/0.60 | 10000 | 65 | 380 |
| I62 | 3.5 | 60 | 54 | 16.5% | 0.37/0.60 | 10000 | 65 | 370 |
| I63 | 3.5 | 61 | 55 | 16.9% | 0.37/0.60 | 10000 | 65 | 305 |
| I64 | 3.7 | 59 | 50 | 16.3% | 0.37/0.60 | 10000 | 65 | 270 |
| I65 | 3.4 | 56 | 51 | 15.4% | 0.37/0.60 | 10000 | 65 | 340 |
| I66 | 3.6 | 55 | 47 | 15.3% | 0.37/0.60 | 10000 | 65 | 345 |
| I67 | 4.2 | 8.8 | 6.6 | 7.1% | 0.14/0.16 | 6000 | 50 | 315 |
| I68 | 3.4 | 55 | 50 | 15.1% | 0.36/0.60 | 4000 | 80 | 465 |
| Sol1 | 4.8 | 8.4 | 5.5 | 6.9% | 0.14/0.15 | 6000 | 50 | 155 |
| Sol2 | 4.7 | 6.8 | 4.6 | 5.5% | 0.14/0.15 | 6000 | 50 | 260 |
| Sol3 | 4.7 | 6.4 | 4.3 | 5.4% | 0.14/0.14 | 6000 | 65 | 190 |

TABLE 3
Structural formulae of the materials for the OLEDs
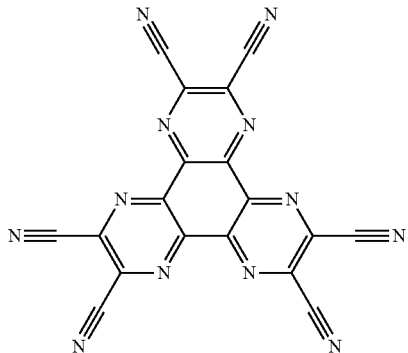 [SMILES: N#Cc1nc2c3nc(C#N)c(C#N)nc3c3nc(C#N)c(C#N)nc3c2nc1C#N]
HATCN
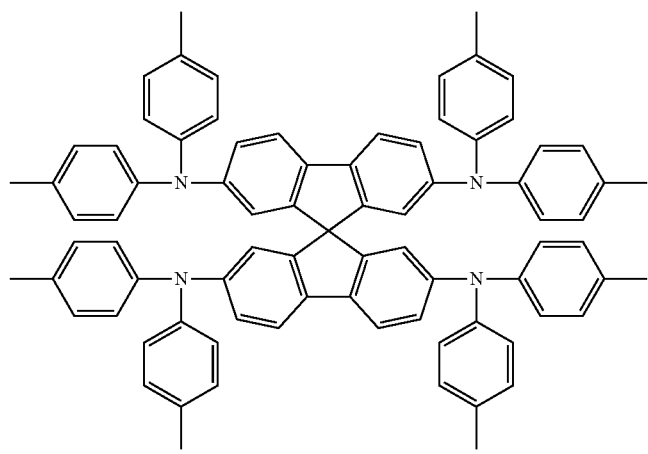
SpA1
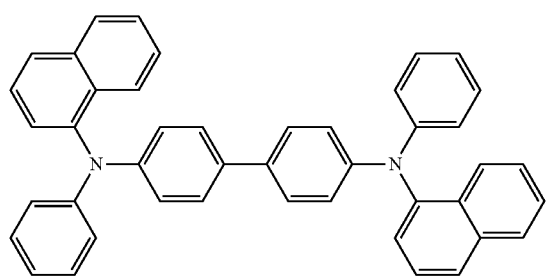 [SMILES: c1ccc(N(c2ccc(-c3ccc(N(c4ccccc4)c4cccc5ccccc45)cc3)cc2)c2cccc3ccccc23)cc1]
NPB (prior art)
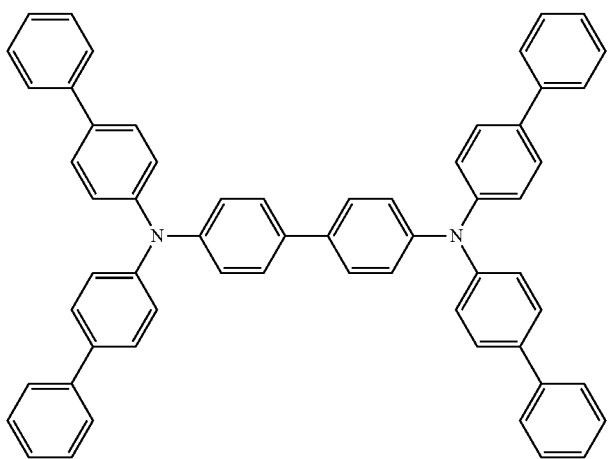 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1]
BPA1 (prior art)

TABLE 3-continued
Structural formulae of the materials for the OLEDs
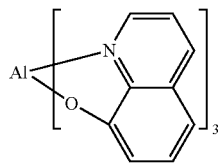  Alq3
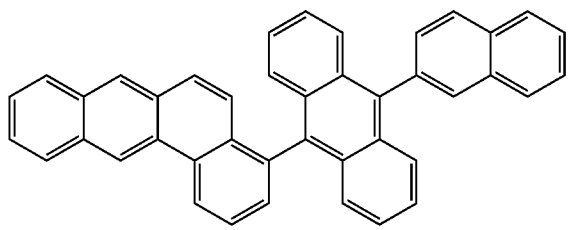 [SMILES: c1ccc2cc(-c3c4ccccc4c(-c4cccc5c4ccc4cc6ccccc6cc45)c4ccccc34)ccc2c1]  M1
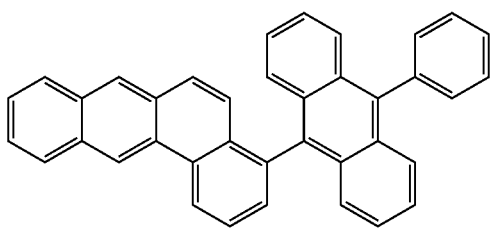 [SMILES: c1ccc(-c2c3ccccc3c(-c3cccc4c3ccc3cc5ccccc5cc34)c3ccccc23)cc1]  M2
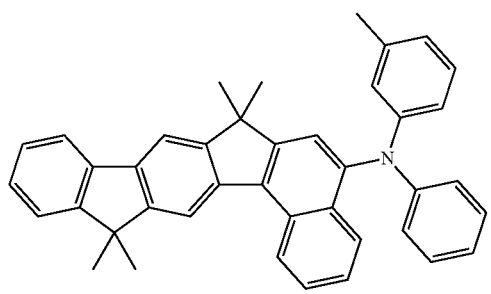 [SMILES: Cc1cccc(N(c2ccccc2)c2cc3c(c4ccccc24)-c2cc4c(cc2C3(C)C)-c2ccccc2C4(C)C)c1]  D1
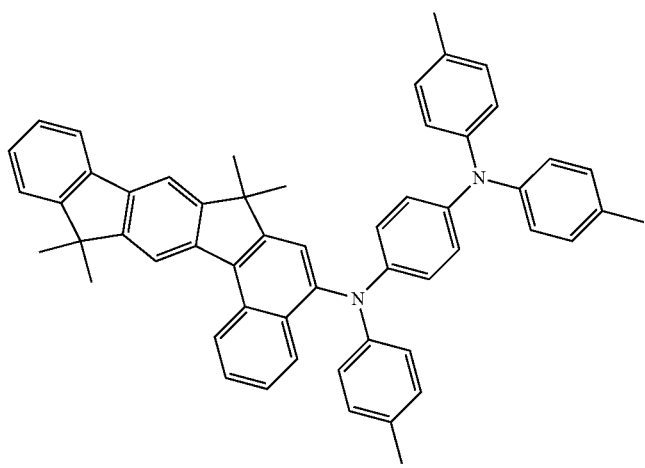 [SMILES: Cc1ccc(N(c2ccc(C)cc2)c2ccc(N(c3ccc(C)cc3)c3cc4c(c5ccccc35)-c3cc5c(cc3C4(C)C)-c3ccccc3C5(C)C)cc2)cc1]  D2

TABLE 3-continued
Structural formulae of the materials for the OLEDs
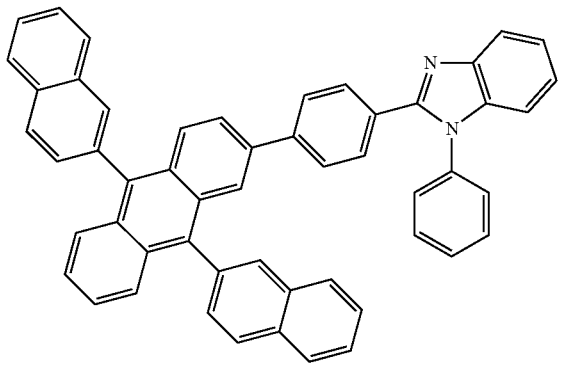 [SMILES: c1ccc(-n2c(-c3ccc(-c4ccc5c(-c6ccc7ccccc7c6)c6ccccc6c(-c6ccc7ccccc7c6)c5c4)cc3)nc3ccccc32)cc1] ETM1
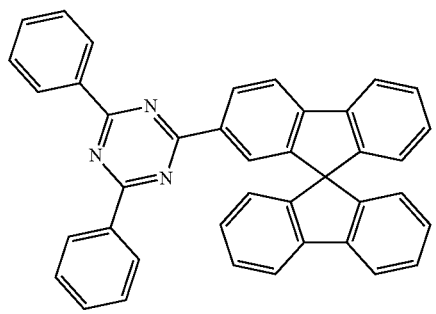 [SMILES: c1ccc(-c2nc(-c3ccccc3)nc(-c3ccc4c(c3)C3(c5ccccc5-c5ccccc53)c3ccccc3-4)n2)cc1] ST1
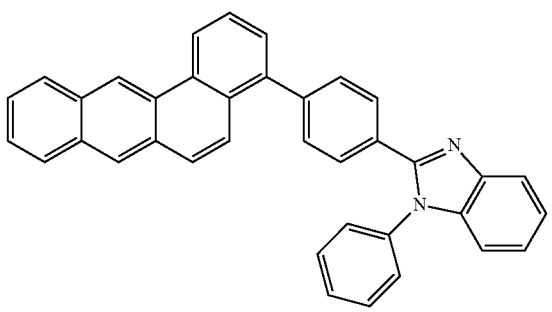 [SMILES: c1ccc(-n2c(-c3ccc(-c4cccc5c4ccc4cc6ccccc6cc45)cc3)nc3ccccc32)cc1] ETM2
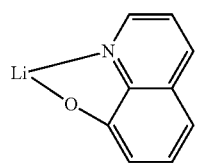 LiQ
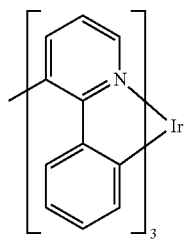 TEG1

TABLE 3-continued
Structural formulae of the materials for the OLEDs
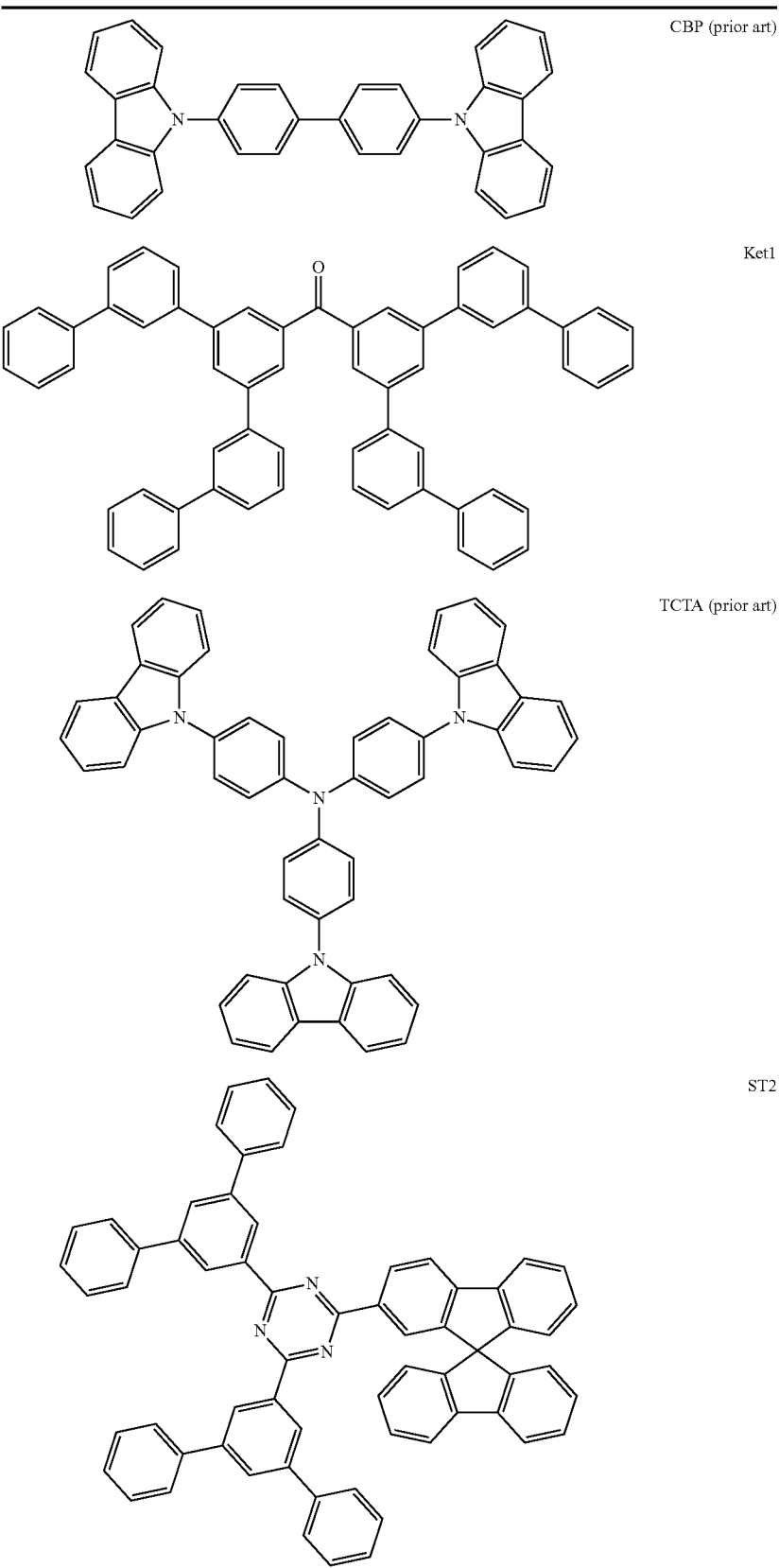
CBP (prior art)
Ket1
TCTA (prior art)
ST2

TABLE 3-continued
Structural formulae of the materials for the OLEDs
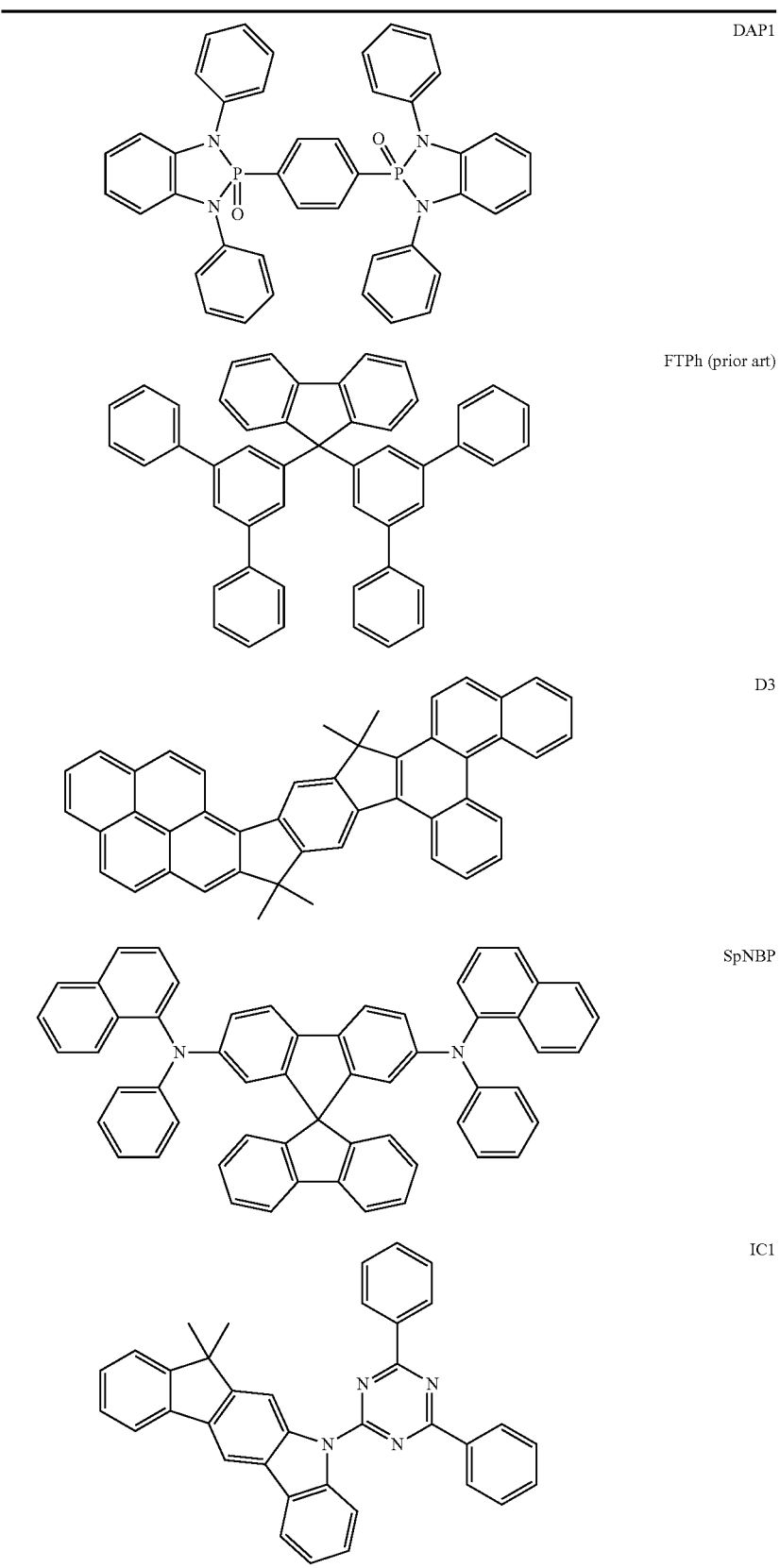
DAP1
FTPh (prior art)
D3
SpNBP
IC1

TABLE 3-continued
Structural formulae of the materials for the OLEDs
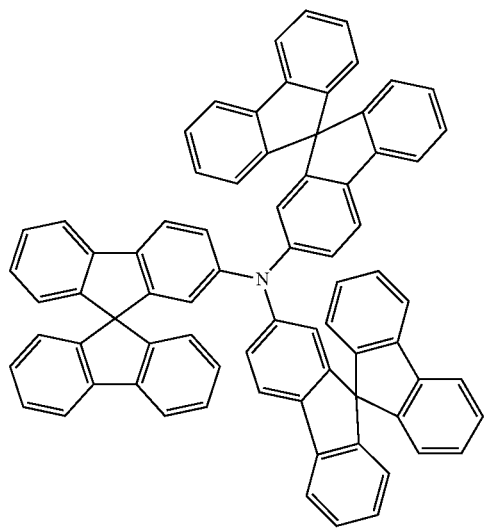 [SMILES: c1ccc2c(c1)-c1ccccc1C21c2ccccc2-c2ccc(N(c3ccc4c(c3)C3(c5ccccc5-c5ccccc53)c3ccccc3-4)c3ccc4c(c3)C3(c5ccccc5-c5ccccc53)c3ccccc3-4)cc21]
TSpA1 (prior art)
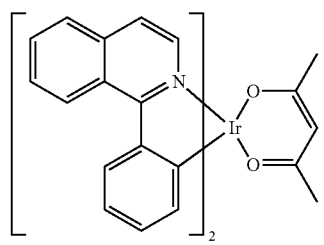
TER1
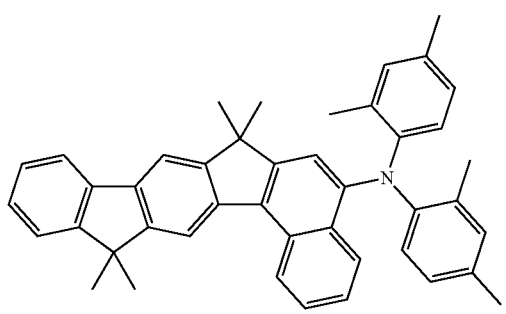 [SMILES: Cc1ccc(N(c2ccc(C)cc2C)c2cc3c(c4ccccc24)-c2cc4c(cc2C3(C)C)-c2ccccc2C4(C)C)c(C)c1]
D4
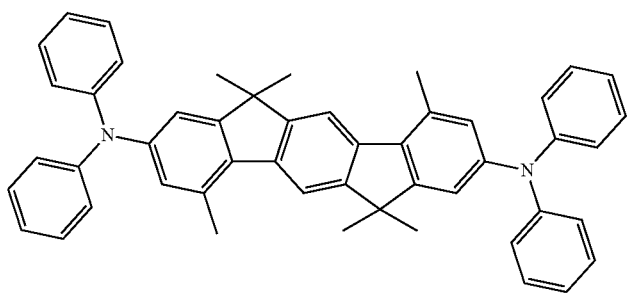 [SMILES: Cc1cc(N(c2ccccc2)c2ccccc2)cc2c1-c1cc3c(cc1C2(C)C)-c1c(C)cc(N(c2ccccc2)c2ccccc2)cc1C3(C)C]
TIFA1

TABLE 3-continued

Structural formulae of the materials for the OLEDs

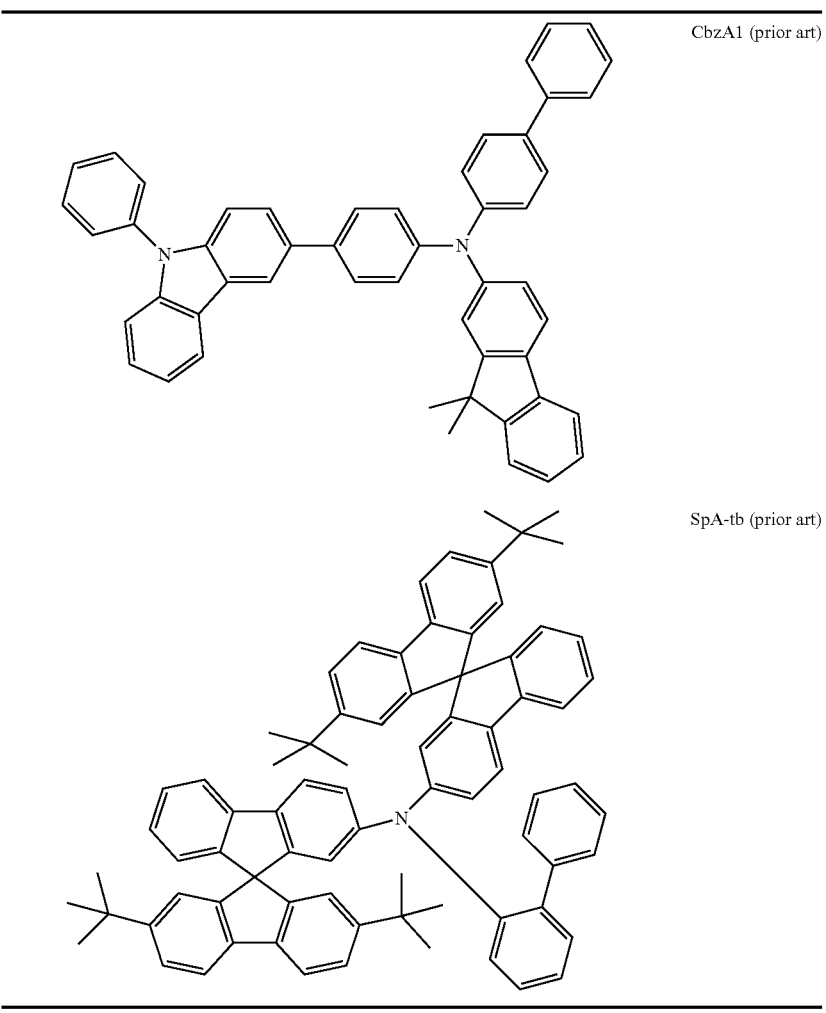

CbzA1 (prior art)

SpA-tb (prior art)

The invention claimed is:

1. A compound of the formula (1),

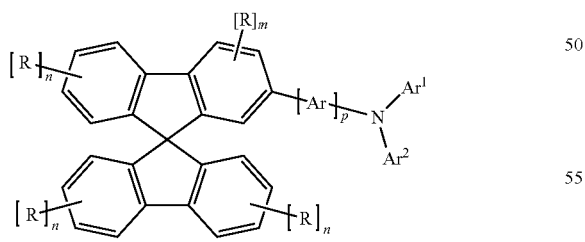

formula (1)

where the following applies to the symbols and indices used:

Ar is, identically or differently on each occurrence, an aromatic ring system selected from the group consisting of benzene, naphthalene, phenanthrene, fluorene, spiro-bifluorene, dibenzofuran and dibenzothiophene, each of which is optionally substituted by one or more radicals $R^1$;

$Ar^1$ and $Ar^2$ are, identically or differently on each occurrence, selected from the groups of the formulae (5) to (28),

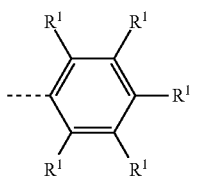

formula (5)

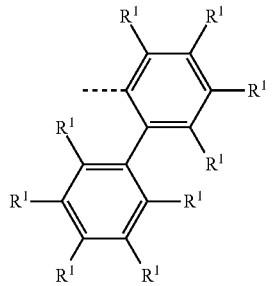

formula (6)

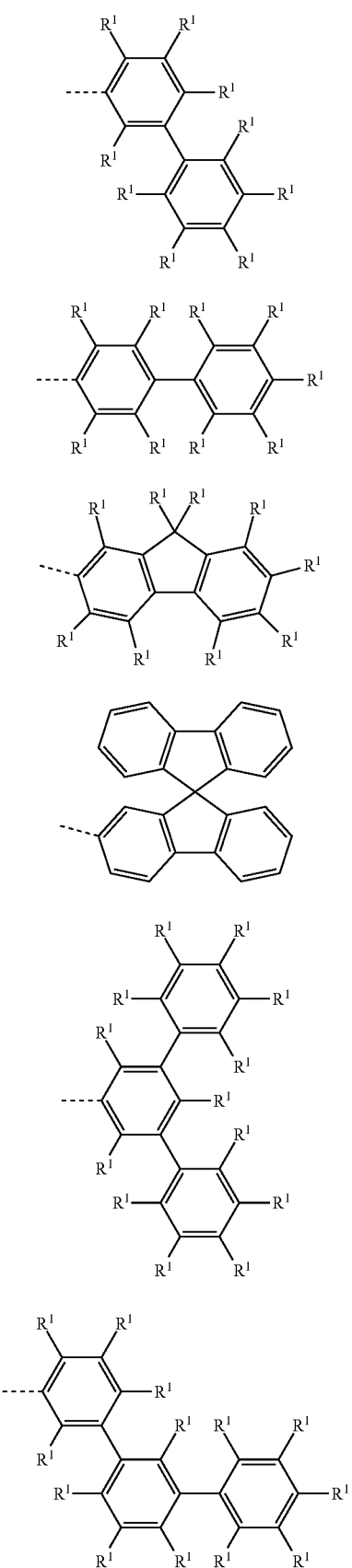
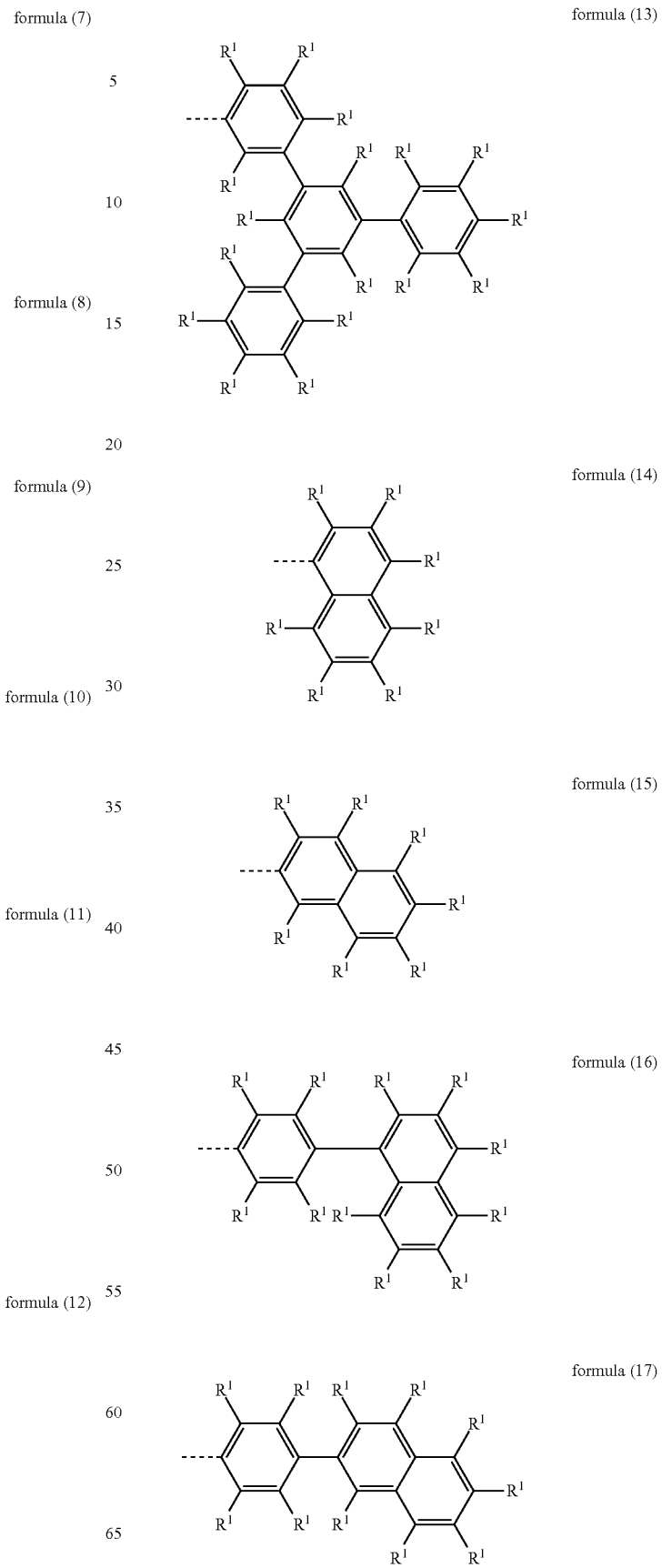

-continued

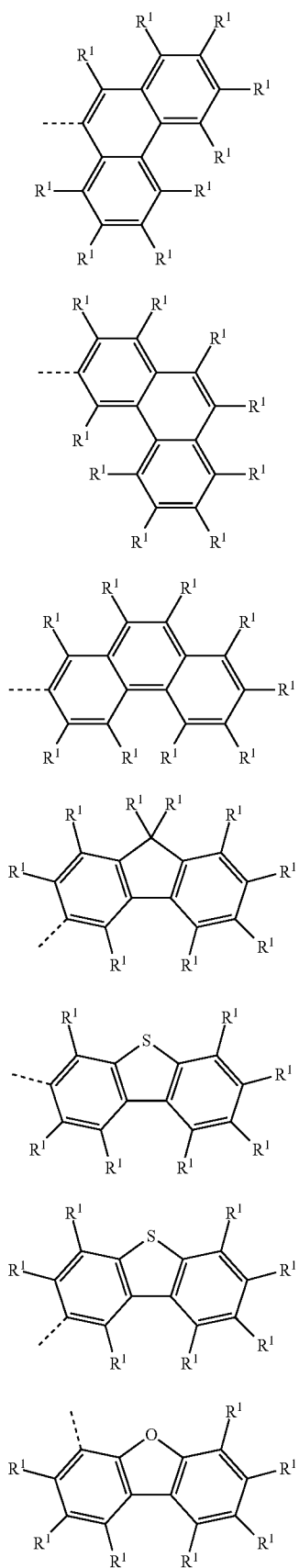

formula (18)

formula (19)

formula (20)

formula (21)

formula (22)

formula (23)

formula (24)

-continued

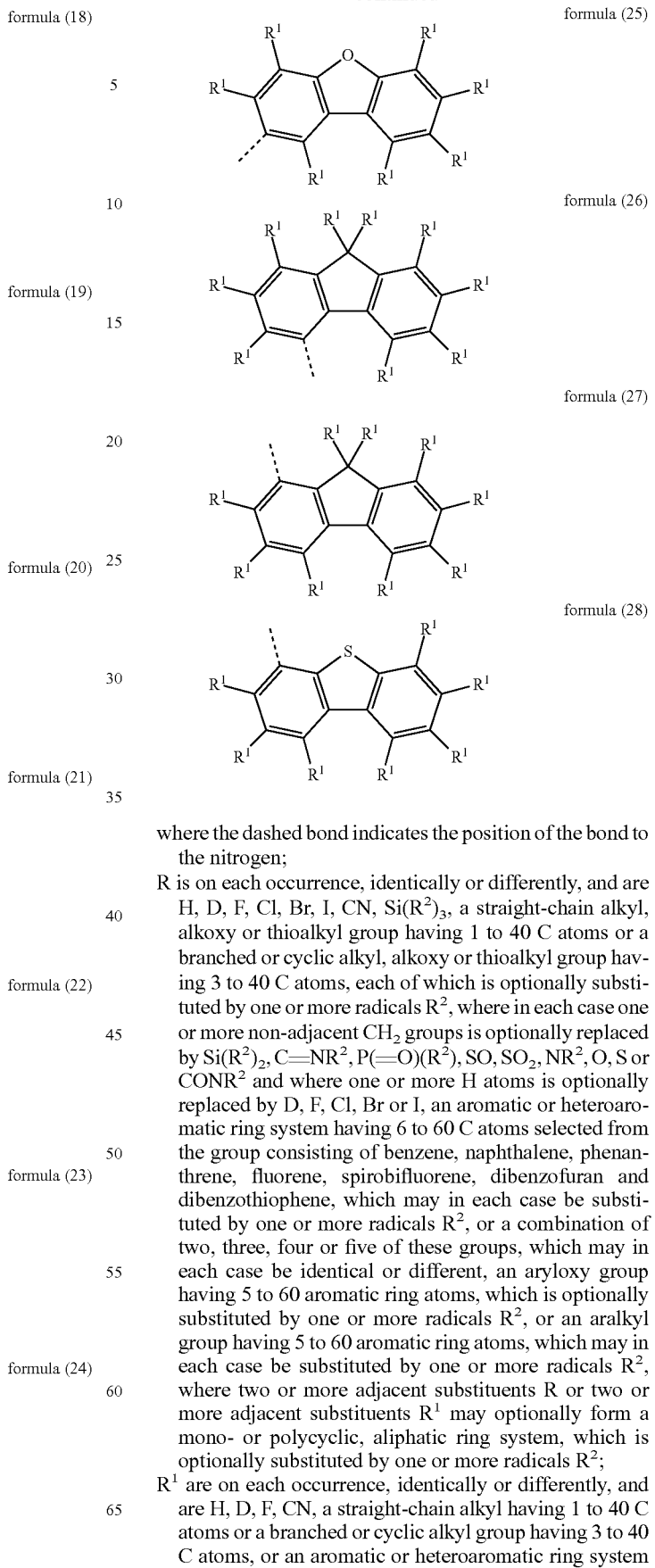

formula (25)

formula (26)

formula (27)

formula (28)

where the dashed bond indicates the position of the bond to the nitrogen;

R is on each occurrence, identically or differently, and are H, D, F, Cl, Br, I, CN, $Si(R^2)_3$, a straight-chain alkyl, alkoxy or thioalkyl group having 1 to 40 C atoms or a branched or cyclic alkyl, alkoxy or thioalkyl group having 3 to 40 C atoms, each of which is optionally substituted by one or more radicals $R^2$, where in each case one or more non-adjacent $CH_2$ groups is optionally replaced by $Si(R^2)_2$, C=$NR^2$, P(=O)($R^2$), SO, $SO_2$, $NR^2$, O, S or $CONR^2$ and where one or more H atoms is optionally replaced by D, F, Cl, Br or I, an aromatic or heteroaromatic ring system having 6 to 60 C atoms selected from the group consisting of benzene, naphthalene, phenanthrene, fluorene, spirobifluorene, dibenzofuran and dibenzothiophene, which may in each case be substituted by one or more radicals $R^2$, or a combination of two, three, four or five of these groups, which may in each case be identical or different, an aryloxy group having 5 to 60 aromatic ring atoms, which is optionally substituted by one or more radicals $R^2$, or an aralkyl group having 5 to 60 aromatic ring atoms, which may in each case be substituted by one or more radicals $R^2$, where two or more adjacent substituents R or two or more adjacent substituents $R^1$ may optionally form a mono- or polycyclic, aliphatic ring system, which is optionally substituted by one or more radicals $R^2$;

$R^1$ are on each occurrence, identically or differently, and are H, D, F, CN, a straight-chain alkyl having 1 to 40 C atoms or a branched or cyclic alkyl group having 3 to 40 C atoms, or an aromatic or heteroaromatic ring system having 6 to 60 C atoms selected from the group consisting of benzene, naphthalene, phenanthrene, dibenzofuran and dibenzothiophene, or a combination of two, three, four or five of these groups, which may in each case be identical or different;

$R^2$ is on each occurrence, identically or differently, is H, D, F, Cl, Br, I, $Si(R^3)_3$, a straight-chain alkyl, alkoxy or thioalkyl group having 1 to 40 C atoms or a branched or cyclic alkyl, alkoxy or thioalkyl group having 3 to 40 C atoms, each of which is optionally substituted by one or more radicals $R^3$, where one or more non-adjacent $CH_2$ groups is optionally replaced by $Si(R^3)_2$, C=$NR^3$, P(=O)($R^3$), SO, $SO_2$, $NR^3$, O, S or $CONR^3$ and where one or more H atoms is optionally replaced by D, F, Cl, Br or I, an aromatic ring system having 6 to 60 C atoms selected from the group consisting of benzene, naphthalene, phenanthrene, fluorene, spirobifluorene or a combination of two, three, four or five of these groups, which may in each case be identical or different, which may in each case be substituted by one or more radicals $R^3$, an aryloxy group having 5 to 60 aromatic ring atoms, which is optionally substituted by one or more radicals $R^3$, or an aralkyl group having 5 to 60 aromatic ring atoms, which is optionally substituted by one or more radicals $R^3$, where two or more adjacent substituents $R^2$ may optionally form a mono- or polycyclic, aliphatic ring system, which is optionally substituted by one or more radicals $R^3$;

$R^3$ is selected from the group consisting of H, D, F, an aliphatic hydrocarbon radical having 1 to 20 C atoms, an aromatic ring system having 6 to 30 C atoms, in which one or more H atoms is optionally replaced by D or F, where two or more adjacent substituents $R^3$ may form a mono- or polycyclic, aliphatic ring system with one another;

m is 0, 1, 2 or 3;

n is on each occurrence, identically or differently, 0, 1, 2, 3 or 4;

p is 0, 1 or 2;

the following compounds are excluded from the invention:

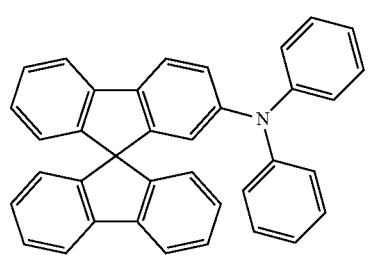

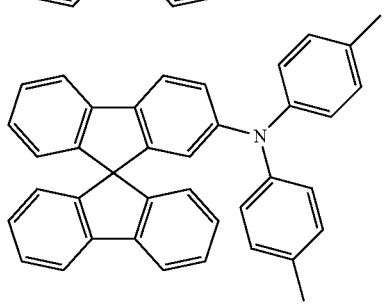

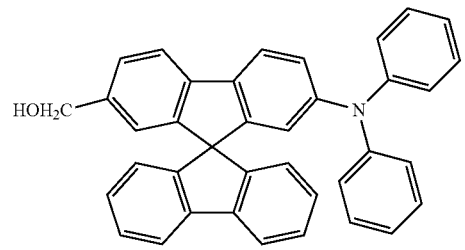

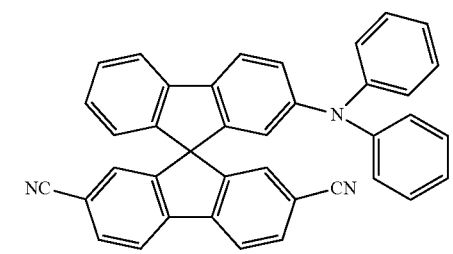

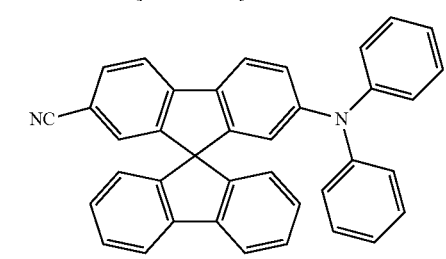

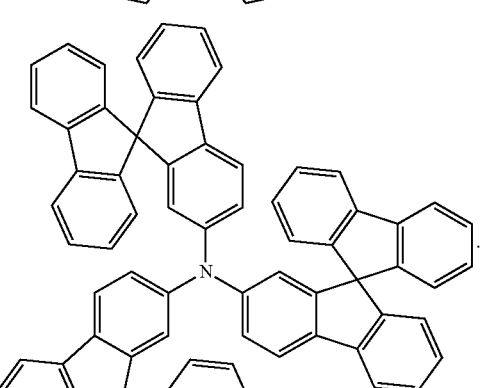

2. The compound according to claim 1 of the formula (2), formula (3a), (3b), (4a) or formula (4b),

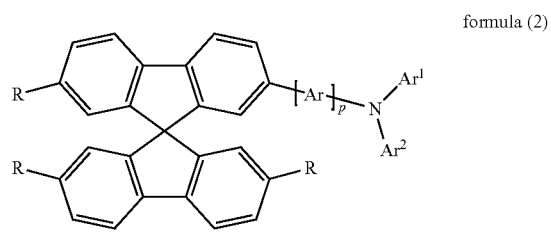

formula (2)

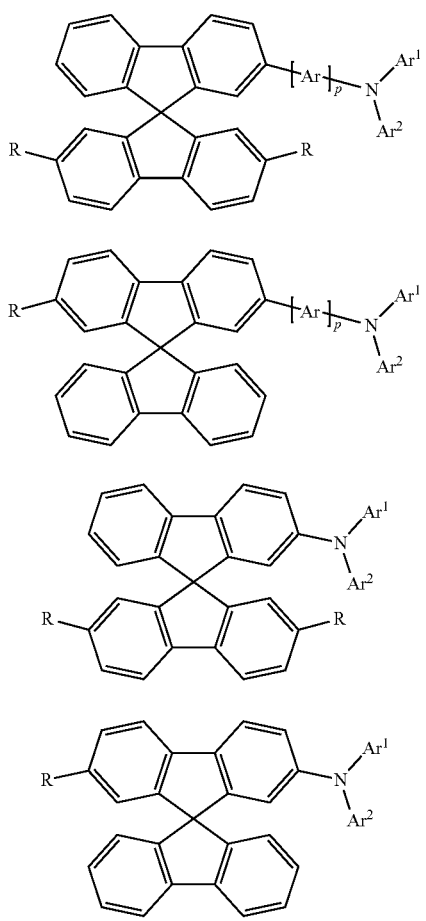

formula (3a)

formula (3b)

formula (4a)

formula (4b)

where the symbols and indices used have the meanings given in claim 1.

3. The compound according to claim 1, wherein the groups Ar¹ and Ar² are selected, identically or differently on each occurrence, from the groups of the formulae (5a) to (28a),

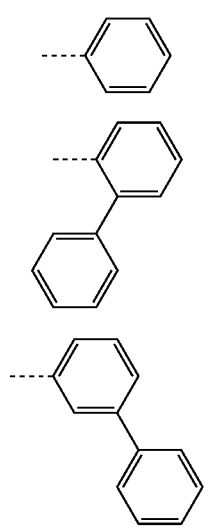

formula (5a)

formula (6a)

formula (7a)

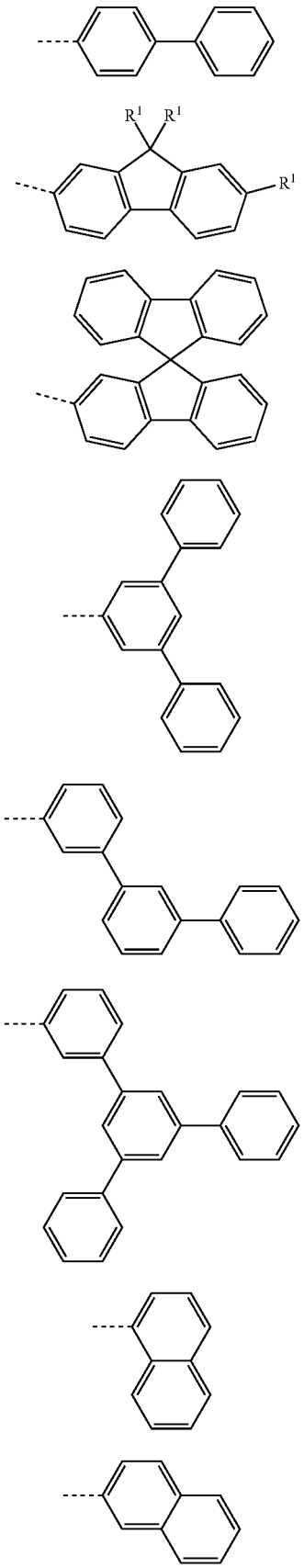

formula (8a)

formula (9a)

formula (10a)

formula (11a)

formula (12a)

formula (13a)

formula (14a)

formula (15a)

-continued formula (16a)
formula (17a)
formula (18a)
formula (19a)
formula (20a)
formula (21a)
formula (22a)
formula (23a)
formula (24a)
formula (25a)

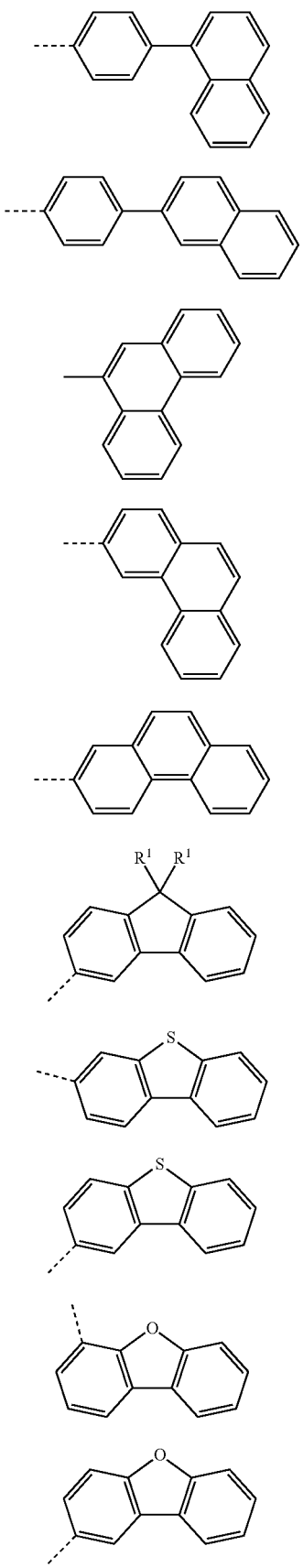

-continued formula (26a)
formula (27a)
formula (28a)

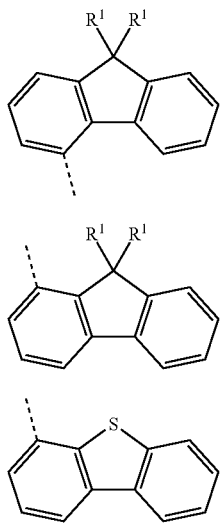

where the symbols used have the meanings given in claim 1, and the dashed bond indicates the position of the bond from the group to the nitrogen.

4. The compound according to claim 1, wherein $Ar^1$ is a group of the formula (6), (7), (8), (9) or (21).

5. The compound according to claim 3, wherein $Ar^1$ is a group of the formula (6a), (7a), (8a), (9a) or (21a).

6. The compound according to claim 1, wherein the groups $Ar^1$ and $Ar^2$ are different from one another.

7. A compound of the formula (1), formula (1)

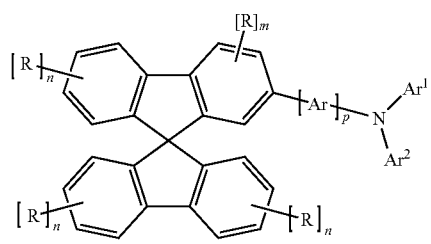

where the following applies to the symbols and indices used:

Ar is, identically or differently on each occurrence, an aromatic ring system selected from the group consisting of benzene, naphthalene, phenanthrene, fluorene, spirobifluorene, dibenzofuran and dibenzothiophene, each of which is optionally substituted by one or more radicals $R^1$;

the group —$NAr^1Ar^2$ has the structure of one of the formulae (29), (30), (31) or (32) or in that the group —Ar—$NAr^1Ar^2$ has the structure of one of the formulae (33), (34), (35) or (36),

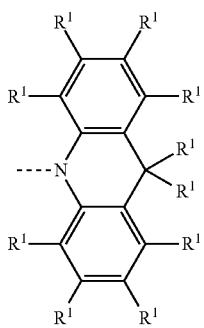
formula (29)
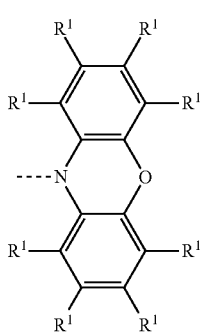
formula (30)
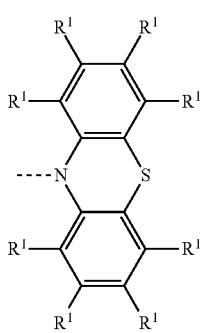
formula (31)
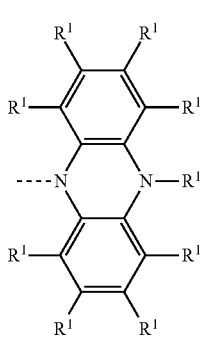
formula (32)
and the dashed bond indicates the bond to the spirobifluorene or to Ar;
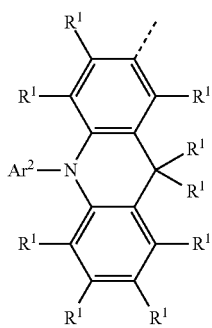
formula (33)
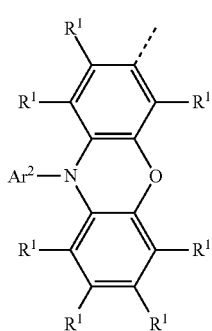
formula (34)
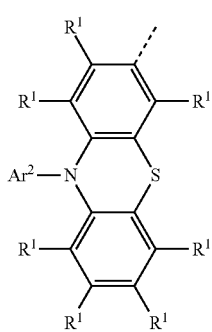
formula (35)
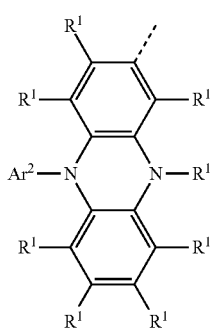
formula (36)
and the dashed bond indicates the bond to the spirobifluorene;
where
R is on each occurrence, identically or differently, and are H, D, F, Cl, Br, I, CN, $Si(R^2)_3$, a straight-chain alkyl, alkoxy or thioalkyl group having 1 to 40 C atoms or a branched or cyclic alkyl, alkoxy or thioalkyl group having 3 to 40 C atoms, each of which is optionally substituted by one or more radicals $R^2$, where in each case one or more non-adjacent $CH_2$ groups is optionally replaced by $Si(R^2)_2$, $C=NR^2$, $P(=O)(R^2)$, SO, $SO_2$, $NR^2$, O, S or $CONR^2$ and where one or more H atoms is optionally replaced by D, F, Cl, Br or I, an aromatic or heteroaromatic ring system having 6 to 60 C atoms selected from the group consisting of benzene, naphthalene, phenanthrene, fluorene, spirobifluorene, dibenzofuran and dibenzothiophene, which may in each case be substituted by one or more radicals $R^2$, or a combination of two, three, four or five of these groups, which may in each case be identical or different, an aryloxy group having 5 to 60 aromatic ring atoms, which is optionally substituted by one or more radicals $R^2$, or an aralkyl group having 5 to 60 aromatic ring atoms, which may in each case be substituted by one or more radicals $R^2$, where two or more adjacent substituents R or two or more adjacent substituents $R^1$ may optionally form a mono- or polycyclic, aliphatic ring system, which is optionally substituted by one or more radicals $R^2$;

$R^1$ are on each occurrence, identically or differently, and are H, D, F, CN, a straight-chain alkyl having 1 to 40 C atoms or a branched or cyclic alkyl group having 3 to 40 C atoms, or an aromatic or heteroaromatic ring system having 6 to 60 C atoms selected from the group consisting of benzene, naphthalene, phenanthrene, dibenzofuran and dibenzothiophene, or a combination of two, three, four or five of these groups, which may in each case be identical or different;

$R^2$ is on each occurrence, identically or differently, is H, D, F, Cl, Br, I, $Si(R^3)_3$, a straight-chain alkyl, alkoxy or thioalkyl group having 1 to 40 C atoms or a branched or cyclic alkyl, alkoxy or thioalkyl group having 3 to 40 C atoms, each of which is optionally substituted by one or more radicals $R^3$, where one or more non-adjacent $CH_2$ groups is optionally replaced by $Si(R^3)_2$, $C=NR^3$, $P(=O)(R^3)$, SO, $SO_2$, $NR^3$, O, S or $CONR^3$ and where one or more H atoms is optionally replaced by D, F, Cl, Br or I, an aromatic ring system having 6 to 60 C atoms selected from the group consisting of benzene, naphthalene, phenanthrene, fluorene, spirobifluorene or a combination of two, three, four or five of these groups, which may in each case be identical or different, which may in each case be substituted by one or more radicals $R^3$, an aryloxy group having 5 to 60 aromatic ring atoms, which is optionally substituted by one or more radicals $R^3$, or an aralkyl group having 5 to 60 aromatic ring atoms, which is optionally substituted by one or more radicals $R^3$, where two or more adjacent substituents $R^2$ may optionally form a mono- or polycyclic, aliphatic ring system, which is optionally substituted by one or more radicals $R^3$;

$R^3$ is selected from the group consisting of H, D, F, an aliphatic hydrocarbon radical having 1 to 20 C atoms, an aromatic ring system having 6 to 30 C atoms, in which one or more H atoms is optionally replaced by D or F, where two or more adjacent substituents $R^3$ may form a mono- or polycyclic, aliphatic ring system with one another;

m is 0, 1, 2 or 3;

n is on each occurrence, identically or differently, 0, 1, 2, 3 or 4;

p is 0, 1 or 2; and the following compounds are excluded from the invention:

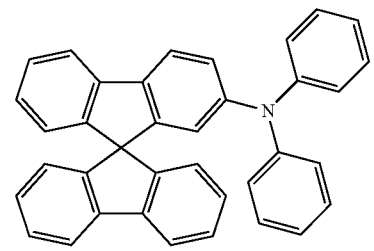

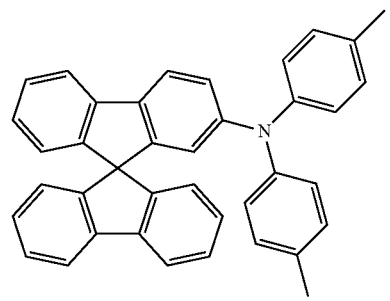

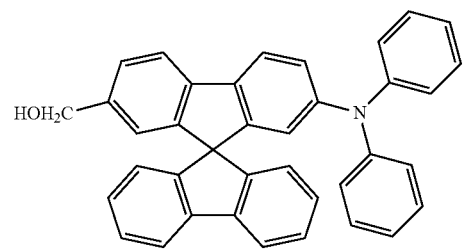

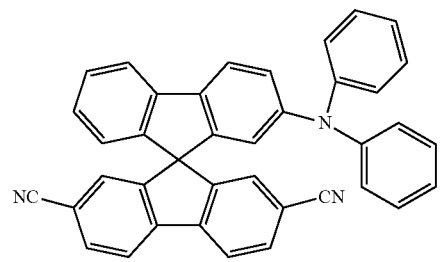

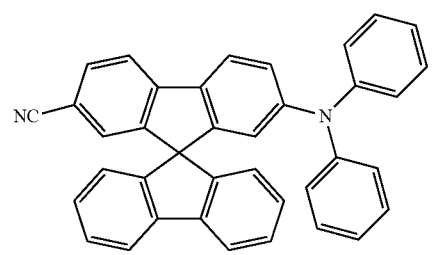

-continued
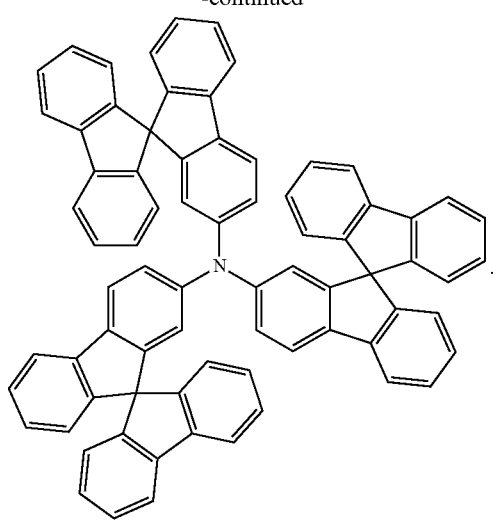
8. The compound according to claim 1, wherein the group —(Ar)$_p$— stands for a group of one of the formulae (37) to (50),
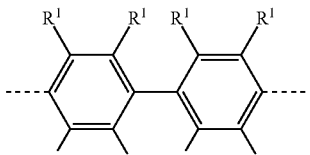
formula (37)
formula (38)
formula (39)
formula (40)
-continued
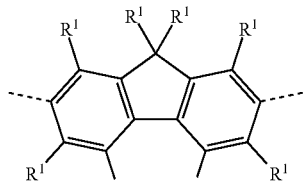
formula (41)
formula (42)
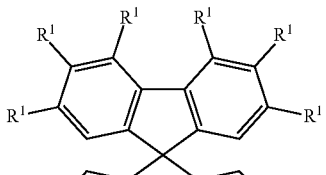
formula (43)
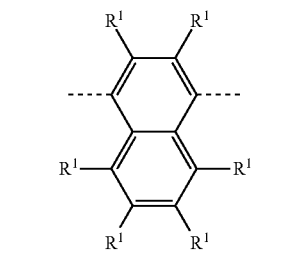
formula (44)
formula (45)
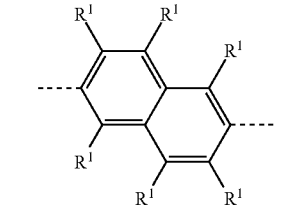
formula (46)
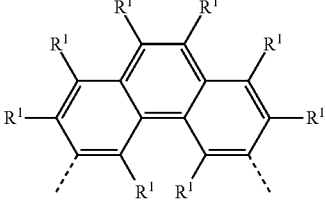
formula (47)
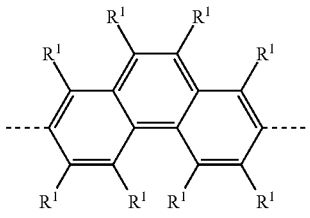

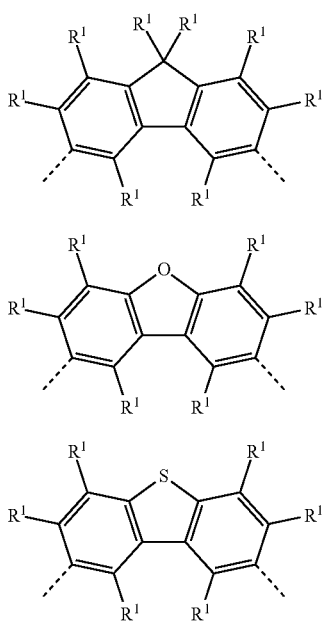

formula (48)

formula (49)

formula (50)

where the symbols used have the meanings given in claim 1, and one dashed bond indicates the bond to the spirobifluorene and the other dashed bond indicates the bond to the nitrogen atom.

9. A process for the preparation of the compound according to claim 1 which comprises coupling a spirobifluorene derivative which is substituted in the 2-position by a reactive leaving group to
   a) a primary amine, followed by coupling to a further aromatic group which is substituted by a reactive leaving group, or
   b) to a secondary amine, or
   c) to a triarylamine derivative.

10. A formulation, comprising at least one compound according to claim 1 and at least one solvent.

11. A solution, dispersion or mini-emulsion comprising at least one compound according to claim 1 and at least one organic solvent.

12. A mixture comprising at least one compound according to claim 1 and at least one further compound.

13. An electronic device comprising the compound according to claim 1.

14. An electronic device comprising the formulation according to claim 10.

15. The electronic device according to claim 13, wherein the electronic device is an organic electroluminescent device (organic light-emitting diode, OLED), an organic integrated circuit (O-IC), an organic field-effect transistor (O-FET), an organic thin-film transistor (O-TFT), an organic light-emitting transistor (O-LET), an organic solar cell (O-SC), an organic dye-sensitised solar cell (ODSSC), an organic optical detector, an organic photoreceptor, na organic field-quench device (O-FQD), a light-emitting electrochemical cell (LEC), an organic laser diode (O-laser) or an organic plasmon emitting device.

16. The electronic device according to claim 14, wherein the electronic device is an organic electroluminescent device (organic light-emitting diode, OLED), an organic integrated circuit (O-IC), an organic field-effect transistor (O-FET), an organic thin-film transistor (O-TFT), an organic light-emitting transistor (O-LET), an organic solar cell (O-SC), an organic dye-sensitised solar cell (ODSSC), an organic optical detector, an organic photoreceptor, na organic field-quench device (O-FQD), a light-emitting electrochemical cell (LEC), an organic laser diode (O-laser) or an organic plasmon emitting device.

17. An organic electroluminescent device comprising the compound according to claim 1 is employed as hole-transport material in a hole-transport or hole-injection or exciton-blocking layer or as matrix material for fluorescent or phosphorescent emitters.

18. An organic electroluminescent device comprising the mixture according to claim 12 is employed as hole-transport material in a hole-transport or hole-injection or exciton-blocking layer or as matrix material for fluorescent or phosphorescent emitters.

19. The compound according to claim 1, wherein
   $R^3$ is selected from the group consisting of H, D, F, an aliphatic hydrocarbon radical having 1 to 20 C atoms, an aromatic ring system having 6 to 30 C atoms, in which one or more H atoms is optionally replaced by D or F.

20. The compound according to claim 1, wherein
   $R^1$ is identically, or differently, on each occurrence selected from the group consisting of H or D, a straight-chain alkyl having 1 to 10 C atoms, and a branched or cyclic alkyl group having 3 to 10 C atoms.

21. The compound according to claim 7, wherein
   $R^1$ is identically, or differently, on each occurrence selected from the group consisting of H or D, a straight-chain alkyl having 1 to 10 C atoms, and a branched or cyclic alkyl group having 3 to 10 C atoms.

* * * * *